United States Patent [19]
Talley et al.

[11] Patent Number: 6,156,781
[45] Date of Patent: *Dec. 5, 2000

[54] SUBSTITUTED PYRAZOLYL BENZENESULFONAMIDES FOR THE TREATMENT OF INFLAMMATION

[75] Inventors: John J Talley, St. Louis, Mo.; Thomas D Penning, Elmhurst; Paul W Collins, Deerfield, both of Ill.; Donald J Rogier, Jr., St. Louis, Mo.; James W Malecha, Libertyville; Julie M Miyashiro, Chicago, both of Ill.; Stephen R Bertenshaw, Brentwood, Mo.; Ish K Khanna, Vernon Hills, Ill.; Matthew J Graneto, St. Louis, Mo.; Roland S Rogers, Richmond Heights, Mo.; Jeffery S Carter, Chesterfield, Mo.; Stephen H. Docter, Mt. Prospect; Stella S Yu, Morton Grove, both of Ill.

[73] Assignee: G. D. Searle & Co., Skokie, Ill.

[*] Notice: This patent is subject to a terminal disclaimer.

[21] Appl. No.: 09/449,076

[22] Filed: Nov. 24, 1999

Related U.S. Application Data

[63] Continuation of application No. 08/957,345, Oct. 24, 1997, abandoned, which is a continuation of application No. 08/648,113, Sep. 6, 1996, Pat. No. 5,760,068, which is a continuation of application No. PCT/US94/12720, Nov. 11, 1994, which is a continuation of application No. 08/223,629, Apr. 6, 1994, Pat. No. 5,521,207, which is a continuation-in-part of application No. 08/160,594, Nov. 30, 1993, Pat. No. 5,466,823.

[51] Int. Cl.⁷ .......................... A61K 31/415; A61P 17/07
[52] U.S. Cl. ........................ 514/406; 514/236.5
[58] Field of Search .............................. 514/406

[56] References Cited

U.S. PATENT DOCUMENTS

| | | |
|---|---|---|
| 3,940,418 | 2/1976 | Hamilton . |
| 4,146,721 | 3/1979 | Rainer . |
| 5,134,142 | 7/1992 | Matsuo et al. . |
| 5,315,012 | 5/1994 | Connolly et al. . |
| 5,387,693 | 2/1995 | Connolly et al. . |
| 5,466,823 | 11/1995 | Talley et al. .......................... 548/277.1 |
| 5,504,215 | 4/1996 | Talley et al. .......................... 548/277.1 |
| 5,510,496 | 4/1996 | Talley et al. .......................... 548/277.1 |
| 5,521,207 | 5/1996 | Talley et al. .......................... 548/277.1 |

FOREIGN PATENT DOCUMENTS

| | | |
|---|---|---|
| 94/75753 | 10/1993 | Australia . |
| 347773 | 12/1989 | European Pat. Off. . |
| 477049 | 3/1992 | European Pat. Off. . |
| 554829 | 8/1993 | European Pat. Off. . |
| 94/14777 | 7/1994 | WIPO . |

OTHER PUBLICATIONS

R. Soliman et al, *J. Pharm. Sci.*, 76, 626 (1987).
H. Mokhtar, *Pak. J. Sci. ind. Res.*, 31, 762 (1988).
H. Mokhtar et al, *Pak. J. Sci. Ind. Res.*, 34, 9 (1991).
M. Cocco et al, I1. *Farmaco–Ed. Sci.*, 40, 272 (1985).
R. Soliman et al, *J. Pharm. Sci.*, 72, 1004 (1983).
H. Feid–Allah, *Pharmazie*, 36, 754 (1981).
R. Soliman et al, *J. Pharm. Sci.*, 70, 602 (1981).
Maybridge Chemical Co./Ryan Scientific Catalog, Compound No. BTB 06812.
H. Mokhtar et al, *Pak. J. Sci. Ind. Res.*, 33:30–36 (1990).
H. Mokhtar et al, *J. Chem. Soc. Pak.*, 10:414–424 (1988).
R. Soliman et al, *J. Pharm. Sci.*, 72:999–1004 (1983).
M.S. I. Makki et al, *Chem. Abstracts*, 121:134017 (1994).
R. Hamilton, *J. Heterocyclic Chem.*, 13, 545 (1976).
M. Hashem et al, *J. Med. Chem.*, 19, 229 (1976).
H. Feid–Allah, *J. Heterocyclic Chem.*, 18, 1561 (1981).
H. Mokhtar et al, *Pharmazie*, 33, 649 (1978).
R. Soliman et al, *Pharmazie*, 33 (1978).

*Primary Examiner*—Robert W. Ramsuer
*Attorney, Agent, or Firm*—Joseph W. Bulock

[57] ABSTRACT

A class of pyrazolyl benzenesulfonamide compounds is described for use in treating inflammation and inflammation-related disorders. Compounds of particular interest are defined by Formula II:

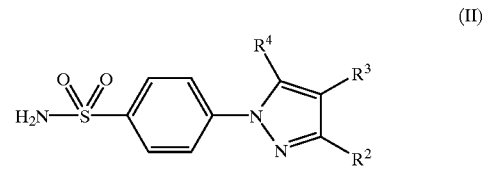

(II)

wherein $R^2$ is selected from hydrido, alkyl, haloalkyl, alkoxycarbonyl, cyano, cyanoalkyl, carboxyl, aminocarbonyl, alkylaminocarbonyl, cycloalkylaminocarbonyl, arylaminocarbonyl, carboxyalkylaminocarbonyl, carboxyalkyl, aralkoxycarbonylalkylaminocarbonyl, aminocarbonylalkyl, alkoxycarbonylcyanoalkenyl and hydroxyalkyl; wherein $R^3$ is selected from hydrido, alkyl, cyano, hydroxyalkyl, cycloalkyl, alkylsulfonyl and halo; and wherein $R^4$ is selected from aralkenyl, aryl, cycloalkyl, cycloalkenyl and heterocyclic; wherein $R^4$ is optionally substituted at a substitutable position with one or more radicals selected from halo, alkylthio, alkylsulfonyl, cyano, nitro, haloalkyl, alkyl, hydroxyl, alkenyl, hydroxyalkyl, carboxyl, cycloalkyl, alkylamino, dialkylamino, alkoxycarbonyl, aminocarbonyl, alkoxy, haloalkoxy, sulfamyl, heterocyclic and amino; provided $R^2$ and $R^3$ are not both hydrido; further provided that $R^2$ is not carboxyl or methyl when $R^3$ is hydrido and when $R^4$ is phenyl; further provided that $R^4$ is not triazolyl when $R^2$ is methyl; further provided that $R^4$ is not aralkenyl when $R^2$ is carboxyl, aminocarbonyl or ethoxycarbonyl; further provided that $R^4$ is not phenyl when $R^2$ is methyl and $R^3$ is carboxyl; and further provided that $R^4$ is not unsubstituted thienyl when $R^2$ is trifluoromethyl; or a pharmaceutically-acceptable salt thereof.

8 Claims, No Drawings

SUBSTITUTED PYRAZOLYL BENZENESULFONAMIDES FOR THE TREATMENT OF INFLAMMATION

This is a continuation of application Ser. No. 08/957,345, filed Oct. 24, 1997, now abandoned, which is a continuation of application Ser. No. 08/648,113, filed Sep. 6, 1996, now U.S. Pat. No. 5,760,068 which is a continuation of PCT/US94/12720, filed Nov. 11, 1994, which is a continuation of application Ser. No. 08/223,629, filed Apr. 6, 1994, issued as U.S. Pat. No. 5,521,207, which is a continuation-in-part of application Ser. No. 08/160,594, filed Nov. 30, 1993, issued as U.S. Pat. No. 5,466,823.

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIDs) that are active in reducing the prostaglandin-induced pain and swelling associated with the inflammation process are also active in affecting other prostagalandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostablandins by inhibiting enzymes in the human arachidonic acid/prostaglandin pathway, including the enzyme cyclooxygenase (COX). The recent discovery of an inducible enzyme associated with inflammation (named "cyclooxygenase II (COX II)" or "prostaglandin G/H synthase II") provides a viable target of inhibition which more effectively reduces inflammation and produces fewer and less drastic side effects.

Pyrazoles have been described for use in the treatment of inflammation. U.S. Pat. No. 5,134,142 to Matsuo et al describes 1,5-diaryl pyrazoles, and specifically, 1-(4-fluorophenyl)-5-[4-(methylsulfonyl)phenyl]-3-trifluoromethyl pyrazole, as having anti-inflammatory activity.

U.S. Pat. No. 3,940,418 to R. Hamilton describes tricyclic 4,5-dihydrobenz[g]indazoles as antiinflammatory agents. In addition, R. Hamilton [J. Heterocyclic Chem., 13, 545 (1976)] describes tricyclic 4,5-dihydrobenz[g]indazoles as antiflammatory agents. U.S. Pat. No. 5,134,155 describes fused tricyclic pyrazoles having a saturated ring bridging the pyrazole and a phenyl radical as HMG-CoA reductase inhibitors. European publication EP 477,049, published Mar. 25, 1992, describes [4,5-dihydro-1-phenyl-1H-benz[g] indazol-3-yl]amides as having antipsychotic activity. European publication EP 347,773, published Dec. 27, 1989, describes [4,5-dihydro-1-phenyl-1H-benz[g]indazol-3-yl] propanamides as immunostimulants. M. Hashem et al [J. Med. Chem., 19, 229 (1976)] describes fused tricyclic pyrazoles, having a saturated ring bridging the pyrazole and a phenyl radical, as antibodies.

Certain substituted pyrazolyl-benzenesulfonamides have been described in the literature as synthetic intermediates. Specifically, 4-[5-(4-chlorophenyl)-3-phenyl-1H-pyrazol-1-yl]benzenesulfonamide has been prepared from a pyrazoline compound as an intermediate for compounds having hypoglycemic activity [R. Soliman et al, J. Pharm. Sci., 76, 626 (1987)]. 4-[5-[2-(4-Bromophenyl)-2H-1,2,3-triazol-4-yl]-3-methyl-1H-pyrazol-1-yl]benzenesulfonamide has been prepared from a pyrazoline compound and described as potentially having hypoglycemic activity [H. Mokhtar, Pak. J. Sci Ind. Res., 31, 762 (1988)]. Similarly, 4-[4-bromo-5-[2-(4-chlorophenyl)-2H-1-1,2,3-triazol-4-yl]-3-methyl-1H-pyrazol-1-yl]benzenesulfonamide has been prepared [(H. Mokhtar et al, Pak. J. Sci. Ind. Res., 34, 9 (1991)].

The phytotoxicity of pyrazole derivatives is described [M. Cocco et al, Il. Farmaco-Ed. Sci., 40, 272 (1985)]. Specifically for 1-[4-(aminosulfonyl)phenyl]-5-phenyl-1H-pyrazole-3,4-dicarboxylic acid.

The use of styryl pyrazole esters for antidiabetes drugs is described [H. Mokhtar et al, Pharmazie, 33, 649–651 (1978)]. The use of styryl pyrazole carboxylic acids for antidiabetes drugs is described [R. Soliman et al, Pharmazie, 33, 184–5 (1978)]. The use of 4-[3,4,5-trisubstituted-pyrazol-1-yl]benzensulfonamides as intermediates for sulfonylurea anti-diabetes agents is described, and specifically, 1-[4-(aminosulfonyl)phenyl]-3-methyl-5-phenyl-1H-pyrazole-4-carboxylic acid [R. Soliman et al. J. Pharm. Sci., 72, 1004 (1983)]. A series of 4-[3-substituted methyl-5-phenyl-1H-pyrazol-1-yl]benzenesulfonamides has been prepared as intermediates for anti-diabetes agents, and more specifically, 4-[3-methyl-5-phenyl-1H-pyrazol-1yl] benzenesulfonamide [H. Feid-Allah, Pharmazie, 36, 754 (1981)]. In addition, 1-(4-[aminosulfonyl]phenyl)-5-phenylpyrazole-3-carboxylic acid has been prepared from the above described 4-[3-methyl-5-phenyl-1H-pyrazol-1-yl] benzenesulfonamide compound [R. Soliman et al, J. Pharm. Sci., 70, 602 (1981)].

DESCRIPTION OF THE INVENTION

A class of compounds useful in treating inflammation-related disorders is defined by Formula I:

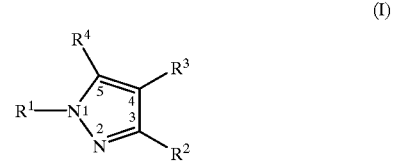

(I)

wherein $R^1$ is selected from aryl and heteroaryl wherein $R^1$ is substituted at a substitutable position with one or more radicals selected from sulfamyl, halo, alkyl, alkoxy, hydroxyl, haloalkyl and

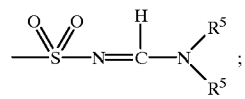

wherein $R^2$ is selected from hydrido, halo, alkyl, haloalkyl, cyano, nitro, formyl, carboxyl, alkoxy, aminocarbonyl, alkoxycarbonyl, carboxyalkyl, alkoxycarbonylalkyl, amidino, cyanoamidino, cyanoalkyl, alkoxycarbonylcyanoalkenyl, aminocarbonylalkyl, N-alkylaminocarbonyl, N-arylaminocarbonyl, N,N- dialkylaminocarbonyl, N-alkyl-N-acrylaminocarbonyl, cycloalkylaminocarbonyl, heterocyclicaminocarbonyl, carboxyalkylaminocarbonyl, aralkoxycarbonylalkylaminocarbonyl, alkylcarbonyl, alkylcarbonylalkyl, hydroxyalkyl, haloaralkyl, carboxyhaloalkyl, alkoxycarbonylhaloalkyl, aminocarbonylhaloalkyl, alkylaminocarbonylhaloalkyl, N-alkylamino, N,N-dialkylamino, N-arylamino, N-aralkylamino, N-alkyl-N-aralkylamino, N-alkyl-N-arylamino, aminoalkyl, N-alalkylaminoalkyl, N,N-dialkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylthio, alkylsulfinyl, alkylsulfonyl, N-alkylaminosulfonyl, N-arylaminosulfonyl, arylsulfonyl, N,N-dialkylaminosulfonyl, N-alkyl-N-arylaminosulfonyl, heterocyclic,

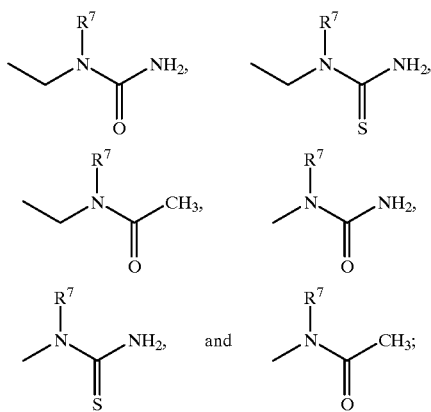

wherein $R^3$ is selected from hydrido, alkyl, halo, haloalkyl, cyano, nitro, formyl, carboxyl, alkloxycarbonyl, carboxyalkyl, alkoxycarbonylalkyl, amidino, cyanoamidino, aminocarbonyl, alkoxy, N-alkylamino, N,N-dialkylamino, aminocarbonylalkyl, N-alkylaminocarbonyl, N-arylaminocarbonyl, N,N-dialkylaminocarbonyl, N-alkyl-N-arylaminocarbonyl, alkylcarbonyl, alkylcarbonylalkyl, hydroxyalkyl, alkylthio, alkylsulfinyl, alkylsulfonyl, N-alkylaminosulfonyl, N-arylaminosulfonyl, arylsulfonyl, N,N-dialkylaminosulfonyl, N-alkyl-N-arylaminosulfonyl, cycloalkyl, heterocyclic, heterocyclicalkyl and aralkyl;
wherein $R^4$ is selected from aralkenyl, aryl, cycloalkyl, cycloalkenyl and heterocyclic; wherein $R^4$ is optionally substituted at a substitutable position with one or more radicals selected from halo, alkylthio, alkylsulfinyl, alkyl, alkenyl, alkylsulfonyl, cyano, carboxyl, alkoxycarbonyl, aminocarbonyl, N-alkylaminocarbonyl, N-arylaminocarbonyl, N,N-dialkylaminocarbonyl, N-alkyl-N-arylaminocarbonyl, haloalkyl, hydroxyl, alkoxy, hydroxyalkyl, haloalkoxy, sulfamyl, N-alkylaminosulfonyl, amino, N-alkylamino, N,N-dialkylamino, heterocyclic, cycloalkylalkyl, nitro, acylamino,

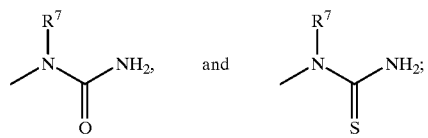

or wherein $R^3$ and $R^4$ together form

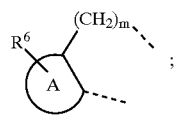

wherein m is 1 to 3, inclusive;
wherein A is selected from phenyl and five or six membered heteroaryl;
wherein $R^5$ is alkyl;
wherein $R^6$ is one or more radicals selected from halo, alkylthio, alkylsulfinyl, alkylsulfonyl, cyano, carboxyl, alkoxycarbonyl, aminocarbonyl, N-alkylaminocarbonyl, N-arylaminocarbonyl, alkyl, alkenyl, N,N-dialkylaminocarbonyl, N-alkyl-N-arylaminocarbonyl, haloalkyl, hydrido, hydroxyl, alkoxy, hydroxyalkyl, haloalkoxy, sulfamyl, N-alkylaminosulfonyl, amino, N-alkylamino, N,N-dialkylamino, heterocyclic, cycloalkylalkyl, nitro and acylamino; and
wherein $R^7$ is selected from hydrido, alkyl, aryl and aralkyl; provided $R^2$ and $R^3$ are not identical radicals selected from hydrido, carboxyl and ethoxycarbonyl; further provided that $R^2$ is not carboxyl or methyl when $R^3$ is hydrido and when $R^4$ is phenyl; further provided that $R^4$ is not triazolyl when $R^2$ is methyl; further provided that $R^4$ is not aralkenyl when $R^2$ is carboxyl, aminocarbonyl or ethoxycarbonyl; further provided that $R^4$ is not phenyl when $R^2$ is methyl and $R^3$ is carboxyl; further provided that $R^4$ is not unsubstituted thienyl when $R^2$ is trifluoromethyl; and further provided that $R^4$ is aryl substituted with sulfamyl or $R^6$ is sulfamyl, when $R^1$ is phenyl not substituted with sulfamyl;
or a pharmaceutically-acceptable salt thereof.

The phrase "further provided", as used in the above description, is intended to mean that the denoted proviso is not to be considered conjunctive with any of the other provisos.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthropathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as antiinflammatory agents, such as for the treatment of arthritis, with the additional benefit of having significantly less harmful side effects.

The present invention preferably includes compounds which selectively inhibit cyclooxygenase II over cyclooxygenase I. Preferably, the compounds have a cyclooxygenase II $IC_{50}$ of less than about 0.2 µM, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 1 µM, and more preferably of greater than 10 µM. Such preferred selectivity may indicate an ability to reduce the incidence of common NSAID-induced side effects.

A preferred class of compounds consists of those compounds of Formula I wherein $R^1$ is selected from aryl selected from phenyl, naphthyl and biphenyl, and five- or six-membered heteroaryl, wherein $R^1$ is substituted at a substitutable position with one or more radicals selected from sulfamyl, halo, lower alkyl, lower alkoxy, hydroxyl, lower haloalkyl and

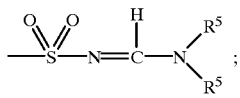

wherein $R^2$ is selected from Hydrido, halo, lower alkyl, lower haloalkyl, cyano, nitro, formyl, carboxyl, lower alkoxycarbonyl, lower carboxyalkyl, lower alkoxycarbonylalkyl, amidino, cyanoamidino, lower cyanoalkyl, lower alkoxycarbonylcyanoalkenyl, aminocarbonyl, lower alkoxy, lower aryloxy, lower aralkoxy, lower aminocarbonylalkyl, lower N-alkylaminocarbonyl, N-arylaminocarbonyl, lower N,N-dialkylaminocarbonyl, lower N-alkyl-N-arylaminocarbonyl, lower cycloalkylaminocarbonyl, lower heterocyclicaminocarbonyl, lower carboxyalkylaminocarbonyl, lower aralkoxycarbonylalkylaminocarbonyl, lower haloaralkyl, lower carboxyhaloalkyl, lower alkoxycarbonylhaloalkyl, lower aminocarbonylhaloalkyl, lower alkylaminocarbonylhaloalkyl, lower alkylcarbonyl, lower alkylcarbonylalkyl, lower alkylamino, lower N,N-dialkylamino, N-arylamino, lower N-aralkylamino, lower N-alkyl-N-aralkylamino, lower N-alkyl-N-arylamino, lower aminoalkyl, lower N-alkylaminoalkyl, lower N,N-dialkylaminoalkyl, lower N-arylaminoalkyl, lower N-aralkylaminoalkyl, lower N-alkyl-N-aralkylaminoalkyl, lower N-alkyl-N-arylaminoalkyl, arylthio, lower aralkylthio, lower hydroxyalkyl, lower alkylthio, lower alkylsulfinyl, lower alkylsulfonyl, lower N-alkylaminosulfonyl, N-arylaminosulfonyl, arylsulfonyl, lower N,N-dialkylaminosulfonyl, lower N-alkyl-N-arylaminosulfonyl, heterocyclic,

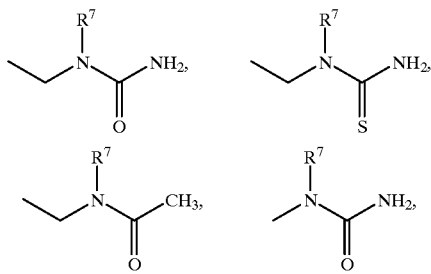

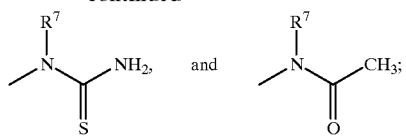

wherein $R^3$ is selected from hydrido, lower alkyl, halo, lower haloalkyl, cyano, nitro, formyl, carboxyl, lower alkoxycarbonyl, lower carboxyalkyl, lower alkoxycarbonylalkyl, amidino, cyanoamidino, aminocarbonyl, lower alkoxy, lower N-alkylamino, lower N,N-dialkylamino, lower N-arylaminocarbonyl, lower N,N-dialkylaminocarbonyl, lower N-alkyl-N-arylaminocarbonyl, lower alkylcarbonyl, lower alkylcarbonylalkyl, lower hydroxyalkyl, lower alkylthio, lower alkylsulfinyl, lower alkylsulfonyl, lower N-alkylaminosulfonyl, N-arylaminosulfonyl, arylsulfonyl, lower N,N-dialkylaminosulfonyl, lower N-alkyl-N-arylaminosulfonyl, lower cycloalkyl, heterocyclic, lower heterocyclicalkyl and lower aralkyl;

where $R^4$ is selected from lower aralkenyl, aryl, lower cycloalkyl, lower cycloalkenyl and five to ten membered heterocyclic; where $R^4$ is optionally substituted at a substitutable position with one or more radicals selected from halo, lower alkylthio, lower alkylsulfinyl, lower alkyl, lower alkenyl, lower alkylsulfonyl, cyano, carboxyl, lower alkoxycarbonyl, aminocarbonyl, lower N-alkylaminocarbonyl, N-arylaminocarbonyl, lower N,N-dialkylaminocarbonyl, lower N-alkyl-N-arylaminocarbonyl, lower haloalkyl, hydroxyl, lower alkoxy, lower hydroxyalkyl, lower haloalkoxy, sulfamyl, lower N-alkylaminosulfonyl, amino, lower N-alkylamino, lower N,N-dialkylamino, five- or six-membered heterocyclic, lower cycloalkylalkyl, nitro, acylamino,

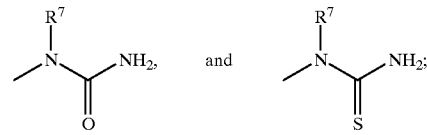

or wherein $R^3$ and $R^4$ together form

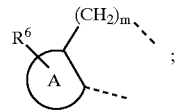

wherein m is 1 to 3, inclusive;
wherein A is selected from phenyl and five or six membered heteroaryl;
wherein $R^5$ is lower alkyl;
wherein $R^6$ is one or more radicals selected from halo, lower alkylthio, lower alkylsulfinyl, lower alkylsulfonyl, cyano, carboxyl, lower alkoxycarbonyl, aminocarbonyl, lower N-alkylaminocarbonyl, N-arylaminocarbonyl, lower alkyl, lower alkenyl, lower N,N-dialkylaminocarbonyl, lower N-alkyl-N-arylaminocarbonyl, lower haloalkyl, hydrido, hydroxyl, lower alkoxy, lower hydroxyalkyl, lower haloalkoxy, sulfamyl, lower N-alkylaminosulfonyl, amino, lower N-alkylamino, lower N,N-dialkylamino, five- or six membered heterocyclic, lower cycloalkylalkyl, nitro and acylamino; and wherein R⁷ is selected from hydrido, lower alkyl, aryl and lower aralkyl;
or a pharmaceutically-acceptable salt thereof.

A more preferred class of compounds consists of those compounds of Formula I wherein R¹ is phenyl, wherein R¹ is substituted at a substitutable position with one or more radicals selected from sulfamyl, halo, lower alkyl, lower alkoxy, hydroxyl, lower haloalkyl and

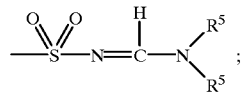

where R² is selected from hydrido, lower alkyl, lower haloalkyl, cyano, carboxyl, lower alkoxycarbonyl, lower carboxyalkyl, lower cyanoalkyl, lower alkoxycarbonylcyanoalkenyl, lower haloaralkyl, lower carboxyhaloalkyl, lower alkoxycarbonylhaloalkyl, lower aminocarbonylhaloalkyl, lower alkylaminocarbonylhaloalkyl, lower N-alkylamino, lower N,N-dialkylamino, N-arylamino, lower N-alkyl-N-arylamino, lower aminoalkyl, lower N-alkylaminoalkyl, lower N,N-dialkylaminoalkyl, lower N-arylaminoalkyl, lower N-aralkylaminoalkyl, lower N-alkyl-N-aralkylaminoalkyl, lower N-alkyl-N-arylaminoalkyl, aryloxy, lower aralkoxy, lower alkoxy, lower alkylthio, arylthio, lower aralkylthio, aminocarbonyl, lower aminocarbonylalkyl, lower N-alkylaminocarbonyl, N-arylaminocarbonyl, lower N,N-dialkylaminocarbonyl, lower N-alkyl-N-acrylaminocarbonyl, lower cycloalkylaminocarbonyl, lower carboxyalkylaminocarbonyl, lower aralkoxycarbonylalkylaminocarbonyl, lower hydroxyalkyl,

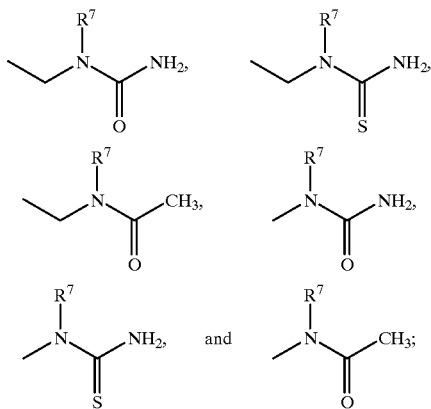

wherein R³ is selected from hydrido, lower alkyl, halo, cyano, lower hydroxyalkyl, lower alkylthio, lower alkylsulfinyl, lower alkylsulfonyl, lower alkoxy, lower N-alkylamino, lower N,N-dialkylamino, lower N-alkylaminosulfonyl, N-arylaminosulfonyl, arylsulfonyl, lower N,N-dialkylaminosulfonyl, lower N-alkyl-N-arylaminosulfonyl and lower cycloalkyl;
wherein R⁴ is selected from lower aralkenyl, aryl, lower cycloalkyl, lower cycloalkenyl and five to ten membered heterocyclic; wherein R⁴ is optionally substituted at a substitutable position with one or more radicals selected from halo, lower alkylthio, lower alkylsulfinyl, lower alkyl, lower alkenyl, lower alkylsulfonyl, cyano, carboxyl, lower alkoxycarbonyl, aminocarbonyl, lower haloalkyl, hydroxyl, lower alkoxy, lower hydroxyalkyl, lower haloalkoxy, sulfamyl, lower alkylaminosulfonyl, amino, lower N-alkylamino, lower N,N-dialkylamino, five or six membered heterocyclic, lower cycloalkylalkyl, nitro,

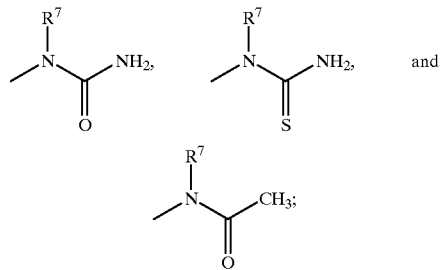

or wherein R³ and R⁴ together form

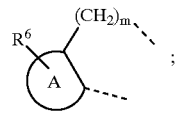

wherein m is 2;
wherein A is selected from phenyl and five or six membered heteroaryl;
wherein R⁵ is lower alkyl;
wherein R⁶ is one or more radicals selected from halo, lower alkylthio, lower alkylsulfinyl, lower alkyl, lower alkenyl, lower alkylsulfonyl, cyano, carboxyl, lower alkoxycarbonyl, aminocarbonyl, lower haloalkyl, hydroxyl, lower alkoxy, lower hydroxyalkyl, lower haloalkoxy, sulfamyl, amino, lower N-alkylamino, lower N,N-dialkylamino, lower cycloalkylalkyl and nitro; and
wherein R⁷ is selected from hydrido, lower alkyl, aryl and lower aralkyl;
or a pharmaceutically-acceptable salt thereof.

An even more preferred class of compounds consists of those compounds of Formula I wherein R¹ is phenyl, wherein R¹ is substituted at a substitutable position with one or more radicals selected from sulfamyl, halo, lower alkyl, lower alkoxy and

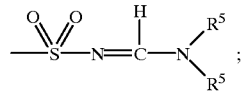

wherein R² is selected from hydrido, lower alkyl, lower haloalkyl, cyano, carboxyl, lower alkoxycarbonyl, lower carboxyalkyl, lower cyanoalkyl, lower alkoxycarbonylcyanoalkenyl, lower haloaralkyl, lower carboxyhaloalkyl, lower alkoxycarbonylhaloalkyl, lower aminocarbonylhaloalkyl, lower alkylaminocarbonylhaloalkyl, lower N-alkylamino, lower N,N-dialkylamino, N-arylamino, lower N-aralkylamino, lower N-alkyl-N-aralkylamino, lower N-alkyl-N-arylamino, lower aminoalkyl, lower N-alkylaminoalkyl, lower N,N-dialkylamiinoalkyl, lower N-arylaminoalkyl, lower N-aralkylaminoalkyl, lower N-alkyl-N-aralkylaminoalkyl, lower N-alkyl-N-arylaminoalkyl, lower alkoxy, aryloxy, lower aralkoxy, lower alkylthio, arylthio, lower aralkylthio, aminocarbonyl, lower aminocarbonylalkyl, lower N-alkylaminocarbonyl, N-arylaminocarbonyl, lower N,N-dialkylaminocarbonyl, lower N-alkyl-N-arylaminocarbonyl, lower cycloalkylaminocarbonyl, lower carboxyalkylaminocarbonyl, lower heterocyclicaminocarbonyl, lower aralkoxycarbonylalkylaminocarbonyl, lower hydroxyalkyl,

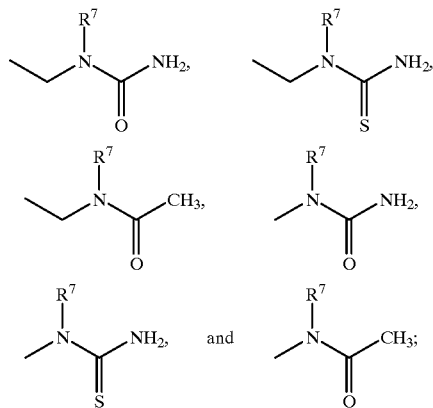

wherein $R^3$ is selected from hydrido, lower alkyl, halo, cyano, lower hydroxyalkyl, lower alkoxy, lower N-alkylamino, lower N,N-dialkylamino, lower alkylthio, lower alkylsulfonyl and lower cycloalkyl;

wherein $R^4$ is selected from lower aralkenyl, aryl, lower cycloalkyl, lower cycloalkenyl and five to ten membered heterocyclic; wherein $R^4$ is optionally substituted at a substitutable position with one or more radicals selected from halo, lower alkylthio, lower alkylsulfinyl, lower alkyl, lower alkenyl, lower alkylsulfonyl, cyano, carboxyl, lower alkoxycarbonyl, aminocarbonyl, lower haloalkyl, hydroxyl, lower alkoxy, lower hydroxyalkyl, lower haloalkoxy, sulfamyl, amino, lower N-alkylamino, lower N,N-dialkylamino, five or six membered heterocyclic, lower cycloalkylalkyl, nitro,

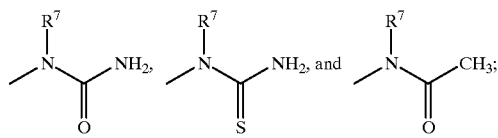

or wherein $R^3$ and $R^4$ together form

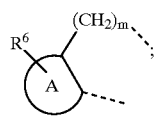

wherein m is 2;
wherein A is selected from phenyl and five membered heteroaryl;
wherein $R^5$ is lower alkyl;
wherein $R^6$ is one or more radicals selected from halo, lower alkyl, lower alkylsulfonyl, lower haloalkyl, lower alkoxy, sulfamyl, amino and nitro; and
wherein $R^7$ is selected from hydrido, lower alkyl, aryl and lower aralkyl;
or a pharmaceutically-acceptable salt thereof.

Within Formula I there is a subclass of compounds which consists of compounds wherein $R^1$ is phenyl substituted at a substitutable position with one or more radicals selected from halo, lower alkyl, sulfamyl and

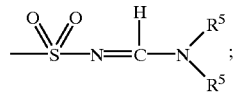

wherein $R^2$ is selected from hydrido, lower alkyl, lower haloalkyl, cyano, carboxyl, lower alkoxycarbonyl, lower carboxyalkyl, lower cyanoalkyl, lower alkoxycarbonylcyanoalkenyl, lower haloaralkyl, lower aminocarbonylhaloalkyl, lower alkylaminocarbonylhaloalkyl, lower N-alkylamino, lower N,N-dialkylamino, N-arylamino, lower N-aralkylamino, lower N-alkyl-N-aralkylamino, lower N-alkyl-N-arylamino, lower aminoalkyl, lower N-alkylaminoalkyl, lower N,N-dialkylaminoalkyl, lower N-arylaminoalkyl, lower N-aralkylaminoalkyl, lower N-alkyl-N-aralkylaminoalkyl, lower N-alkyl-N-arylaminoalkyl, lower alkoxy aryloxy, lower aralkoxy, lower alkylthio, arylthio, lower aralkylthio, aminocarbonyl, lower aminocarbonylalkyl, lower N-alkylaminocarbonyl, N-arylaminocarbonyl, lower N,N-dialkylaminocarbonyl, lower N-alkyl-N-arylaminocarbonyl, lower cycloalkylaminocarbonyl, lower carboxyalkylaminocarbonyl, lower aralkoxycarbonylalkylaminocarbonyl, lower hydroxyalkyl,

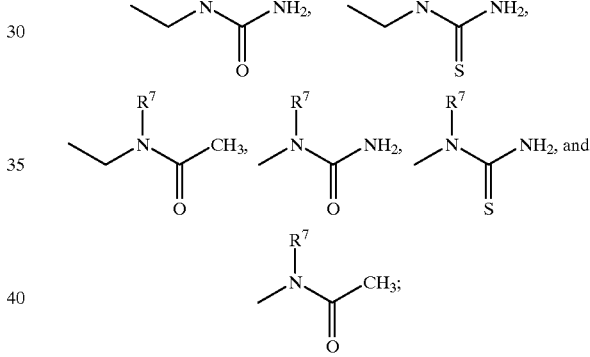

wherein $R^3$ is selected from hydrido, lower alkyl, halo, cyano, lower hydroxyalkyl, lower alkoxy, lower alkylthio, lower N-alkylamino, lower N,N-dialkylamino, lower alkylsulfonyl and lower cycloalkyl;
wherein $R^4$ is selected from lower aralkenyl, aryl, lower cycloalkyl, lower cycloalkenyl and five to ten membered heterocyclic; wherein $R^4$ is optionally substituted at a substitutable position with one or more radicals selected from halo, lower alkylthio, lower alkylsulfinyl, lower alkyl, lower alkenyl, lower alkylsulfonyl, cyano, carboxyl, lower alkoxycarbonyl, aminocarbonyl, lower haloalkyl, hydroxyl, lower alkoxy, lower hydroxyalkyl, lower haloalkoxy, sulfamyl, lower alkylaminocarbonyl, amino, lower N-alkylamino, lower N,N-dialkylamino, five or six membered heterocyclic lower cycloalkylalkyl, nitro,

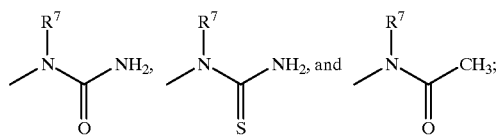

wherein $R^5$ is lower alkyl; and wherein R⁷ is selected from hydrido, lower alkyl, aryl and lower aralkyl;
or a pharmaceutically-acceptable salt thereof.

A class of compounds of particular interest consists of those compounds of Formula I wherein R¹ is phenyl, substituted at a substitutable position with one or more radicals selected from fluoro, chloro, methyl, sulfamyl and

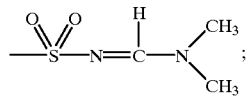

wherein R² is selected from hydrido, methyl, ethyl, isopropyl, tert-butyl, isobutyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, dichloropropyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, acetyl, propionyl, butyryl, isobutyryl, valeryl, isovaleryl, pivaloyl, hexanoyl, trifluoroacetyl, cyanomethyl, ethoxycarbonylcyanoethenyl, 1,1-difluoro-1-phenylmethyl, 1,1-difluoro-1-phenylethyl, difluoroacetyl, methoxycarbonyldifluoromethyl, difluoroacetamidyl, N,N-dimethyldifluoroacetamidyl, N-phenyldifluoroacetamidyl, N-ethylamino, N-methylamino, N,N-dimethylamino, N,N-diethylamino, N-phenylamino, N-benzylamino, N-phenylethylamino, N-methyl-N-benzylamino, N-ethyl-N-phenylamino, N-methyl-N-phenylamino, aminomethyl, N-methylaminomethyl, N,N-dimethylaminomethyl, N-phenylaminomethyl, N-benzylaminomethyl, N-methyl-N-benzylaminomethyl, N-methyl-N-phenylaminomethyl, methoxy, ethoxy, phenoxy, benzyloxy, methylthio, phenylthio, benzylthio, N-methylurea, N-methylthiourea, N-methylacetamidyl, urea, ureamethyl, thiourea, thioureamethyl, acetamidyl, N-phenylthioureamethyl, N-benzylthiouramethyl, N-methylthioureamethyl, N-phenylureamethyl, N-benzylureamethyl, N-methylureamethyl, N-phenylacetamidylmethyl, N-benzylacetamidylmethyl, N-methylacetamidylmethyl, aminocarbonyl, aminocarbonylmethyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-petnylaminocarbonyl, N-phenylaminocarbonyl, N,N-dimethylaminocarbonyl, N-phenylaminocarbonyl, N,N-dimethylaminocarbonyl, N-methyl-N-ethylaminocarbonyl, N-(3-fluorophenyl)aminocarbonyl, N-(4-methylphenyl)aminocarbonyl, N-(3-chlorophenyl)aminocarbonyl, N-methyl-N-(3-chlorophenyl)aminocarbonyl, N-(4-methoxyphenyl)aminocarbonyl, N-methyl-N-phenylaminocarbonyl, cyclopentylaminocarbonyl, cyclohexylaminocarbonyl, carboxymethylaminocarbonyl, benzyloxycarbonylmethylaminocarbonyl, hydroxypropyl, hydroxymethyl, and hydroxypropyl;
wherein R³ is selected from hydrido, methyl, ethyl, isopropyl, tert-butyl, isobutyl, hexyl, fluoro, chloro, bromo, cyano, methoxy, methylthio, methylsulfonyl, N-methylamino, N-ethylamino, N,N-dimethylamino, N,N-diethylamino, cyclopropyl, cyclopentyl, hydroxypropyl, hydroxymethyl, and hydroxyethyl; and
wherein R⁴ is selected from phenylethenyl, phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 1-cyclopentenyl, 4-cyclopentenyl, benzofuryl, 2,3-dihydrobenzofuryl, 1,2,3,4-tetrahydronaphthyl, benzothienyl, indenyl, indanyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl and pyrazinyl; wherein R⁴ is optionally substituted at a substitutable position with one or more radicals selected from fluoro, chloro, bromo, methylthio, methylsulfinyl, methyl, ethyl, propyl, isopropyl, tert-butyl, isobutyl, hexyl, ethylenyl, propenyl, methylsulfonyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, fluoromethyl, difluoromethyl, trifluoromethyl, chloromethyl, dichloromethyl, trichloromethyl, pentafluoroethyl, heptafluoropropyl, bromodifluoromethyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, sulfamyl, methylaminosulfonyl, hydroxypropyl, hydroxyisopropyl, hydroxymethyl, hydroxyethyl, trifluoromethoxy, amino, N-methylamino, N-ethylamino, N-ethyl-N-methylamino, N,N-diethylamino, formylamino, methylcarbonylamino, trifluoroacetamino, piperadinyl, piperzinyl, morpholino, cyclohexylmethyl, cyclopropylmethyl, cyclopentylmethyl, nitro,

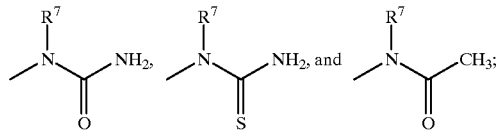

and
wherein R⁷ is selected form hydrido, methyl, ethyl, phenyl and benzyl;
or a pharmaceutically-acceptable salt thereof.

Within Formula I there is a second subclass of compounds of high interest wherein R¹ is phenyl substituted at a substitutable position with sulfamyl; wherein R² is selected from lower haloalkyl, cyano, carboxyl, lower alkoxycarbonyl, lower carboxyalkyl, aminocarbonyl, lower N-alkylaminocarbonyl, N-arylaminocarbonyl, lower N,N-dialkylaminocarbonyl, lower N-alkyl-N-arylaminocarbonyl, lower cycloalkylaminocarbonyl and lower hydroxyalkyl; wherein R³ and R⁴ together form

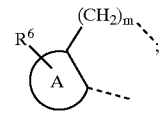

wherein m is 2: wherein A is selected from phenyl and five membered heteroaryl; and wherein R⁶ is one or more radicals selected from halo, lower alkyl, lower alkylsulfonyl, lower haloalkyl, lower alkoxy, amino and nitro; or a pharmaceutically-acceptable salt thereof.

A class of compounds of particular interest consists of those compounds of Formula I wherein R² is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, acetyl, propionyl, butyryl, isobutyryl, valeryl, isovaleryl, pivaloyl, hexanoyl, trifluoroacetyl, aminocarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N-phenylaminocarbonyl, N,N-dimethylaminocarbonyl, N-methyl-N-ethylaminocarbonyl, N-(3-fluorophenyl)aminocarbonyl, N-(4-methylphenyl)aminocarbonyl, N-(3-chlorophenyl)aminocarbonyl, N-(4-methoxyphenyl)aminocarbonyl, N-methyl-N-phenylaminocarbonyl, cyclohexylaminocarbonyl, hydroxypropyl, hydroxymethyl and hydroxyethyl; wherein A is selected from phenyl, furyl and thienyl; and wherein $R^6$ is one or more radicals selected from fluoro, chloro, bromo, methylsulfonyl, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, methylenedioxy, ethoxy, propoxy, n-butoxy, amino, and nitro; or a pharmaceutically-acceptable salt thereof.

Within Formula I there is a third subclass of compounds of high interest wherein $R^1$ is selected from phenyl, naphthyl, biphenyl, and five- or six-membered heteroaryl, wherein $R^1$ is substituted at a substitutable position with one or more radicals selected from halo, lower alkyl, lower alkoxy, hydroxyl and lower haloalkyl; wherein $R^2$ is selected from lower haloalkylo; wherein $R^3$ is hydrido; and wherein $R^4$ is aryl substituted at a substitutable position with sulfamyl; or a pharmaceutically-acceptable salt thereof.

A class of compounds of particular interest consists of those compounds of Formula I wherein $R^1$ is selected from phenyl, naphthyl, benzofuryl, benzothienyl, indolyl, benzodioxolyl, benzodioxanyl, pyridyl, thienyl, thiazolyl, oxazolyl, furyl and pyrazinyl; wherein $R^1$ is substituted at a substitutable position with one or more radicals selected from fluoro, chloro, bromo, fluoromethyl, difluoromethyl, trifluoromethyl, pentafluoroethyl, heptafluoropropyl, difluorochloromethyl, difluoropropyl, dichlorofluoromethyl, difluoroethyl, difluoropropyl, dichloroethyl, methyl, ethyl, propyl, hydroxyl, methoxy, ethoxy, propoxy and n-butoxy; wherein $R^2$ is selected from fluoromethyl, difluoromethyl, trifluoromethyl, chloromethyl, dichloromethyl, trichloromethyl, pentafluoroethyl, heptafluoropropyl, difluorochloromethyl, difluoroethyl, dichlorofluoromethyl, difluoropropyl, dichloroethyl and dichloroporpyl; wherein $R^3$ is hydrido; and wherein $R^4$ is phenyl substituted at a substitutable position with sulfamyl; or a pharmaceutically-acceptable salt thereof.

Within Formula I there is a subclass of compounds of high interest represented by Formula II:

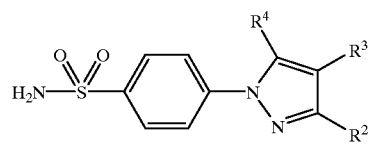

(II)

wherein $R^2$ is selected from hydrido, alkyl, haloalkyl, alkoxycarbonyl, cyano, cyanoalkyl, carboxyl, aminocarbonyl, alkylaminocarbonyl, cycloalkylaminocarbonyl, arylaminocarbonyl, carboxyalkylaminocarbonyl, carboxyalkyl, aralkoxycarbonylalkylaminocarbonyl, aminocarbonylalkyl, alkoxycarbonylcyanoalkenyl and hydroxyalkyl;

wherein $R^4$ is selected from hydrido, alkyl, cyano, hydroxyalkyl, cycloalkyl, alkylsulfonyl and halo; and wherein $R^4$ is selected from aralkenyl, aryl, cycloalkyl, cycloalkenyl and heterocyclic; wherein $R^4$ is optionally substituted at a substitutable position with one or more radicals selected from halo, alkylthio, alkylsulfonyl, cyano, nitro, haloalkyl, alkyl, hydroxyl, alkenyl, hydroxyalkyl, carboxy, cycloalkyl, alkylamino, dialkylamino, alkoxycarbonyl, aminocarbonyl, alkoxy, haloalkoxy, sulfamyl, heterocyclic and amino;

provided $R^2$ and $R^3$ are not both hydrido; further provided that $R^2$ is not carboxyl or methyl when $R^3$ is hydrido and when $R^4$ is phenyl; further provided that $R^4$ is not triazolyl when $R^2$ is methyl; further provided that $R^4$ is not aralkenyl when $R^2$ is carboxyl, aminocarbonyl or ethoxycarbonyl; further provided that $R^4$ is not phenyl when $R^2$ is methyl and $R^3$ is carboxyl; and further provided that $R^4$ is not unsubstituted thienyl when $R^2$ is trifluoromethyl;

or a pharmaceutically-acceptable salt thereof.

A class of compounds of particular interest consists of those compounds of Formula II wherein $R^2$ is selected from hydrido, lower alkyl, lower haloalkyl, lower alkoxycarbonyl, cyano, lower cyanoalkyl, carboxyl, aminocarbonyl, lower alkylaminocarbonyl, lower cycloalkylaminocarbonyl, arylaminocarbonyl, lower carboxyalkylaminocarbonyl, lower aralkoxycarbonylalkylaminocarbonyl, lower aminocarbonylalkyl, lower carboxyalkyl, lower alkoxycarbonylcyanoalkenyl and lower hydroxyalkyl;

wherein $R^3$ is selected from hydrido, lower alkyl, cyano, lower hydroxyalkyl, lower cycloalkyl, lower alkylsulfonyl and halo; and wherein $R^4$ is selected from aralkenyl, aryl, cycloalkyl, cycloalkenyl and heterocyclic; wherein $R^4$ is optionally substituted at a substitutable position with one or more radicals selected from halo, lower alkylthio, lower alkylsulfonyl, cyano, nitro, lower haloalkyl, lower alkyl, hydroxyl, lower alkenyl, lower hydroxyalkyl, carboxyl, lower cycloalkyl, lower alkylamino, lower dialkylamino, lower alkoxycarbonyl, aminocarbonyl, lower alkoxy, lower haloalkoxy, sulfamyl, five or six membered heterocyclic and amino; or a pharmaceutically-acceptable salt thereof.

A family of specific compounds of particular interest within Formula I consists of compounds and pharmaceutically-acceptable salts thereof as follows:

4-[5-(4-(N-ethylamino)phenyl)-3-(trifluoromethyl)-1H-pyrazol-1-yl]benzenesulfonamide;

4-[5-(4-(N-ethyl-N-methylamino)phenyl)-3-(trifluoromethyl)-1H-pyrazol-1-yl]benzenesulfonamide;

4-[5-(3-fluoro-4-(N-methylamino)phenyl)-3-(trifluoromethyl)-1H-pyrazol-1-yl]benzenesulfonamide;

4-[5-(3-chloro-4-(N-methylamino)phenyl)-3-(trifluoromethyl)-1H-pyrazol-1-yl]benzenesulfonamide;

4-[5-(3-methyl-4-(N-methylamino)phenyl)-3-(trifluoromethyl)-1H-pyrazol-1H-pyrazol-1-yl]benzenesulfonamide;

4-[5-(4-(N,N-dimethylamino)-3-fluorophenyl)-3-(trifluoromethyl)-1H-pyrazol-1-yl]benzenesulfonamide;

4-[5-(3-chloro-4-(N,N-dimethylamino)phenyl)-3-(trifluoromethyl)-1H-pyrazol-1-yl]benzenesulfonamide;

4-[5-(4-(N,N-dimethylamino)-3-methylphenyl)-3-(trifluoromethyl)-1H-pyrazol-1-yl]benzenesulfonamide;

4-[5-(4-(N-ethyl-N-methylamino)-3-fluorophenyl)-3-(trifluoromethyl)-1H-pyrazol-1-yl]benzenesulfonamide;

4-[5-(3-chloro-4-(N-ethyl-N-methylamino)phenyl)-3-(trifluoromethyl)-1H-pyrazol-1-yl]benzenesulfonamide;

4-[5-(4-(N-ethyl-N-methylamino)-3-methylphenyl)-3-(trifluoromethyl)-1H-pyrazol-1-yl]benzenesulfonamide;

4-[5-(4-(N,N-diethylamino)-3-fluorophenyl)-3-(trifluoromethyl)-1H-pyrazol-1-yl]benzenesulfonamide;

4-[5-(4-(3-chloro-4-(N,N-diethylamino)phenyl)-3-(trifluoromethyl)-1H-pyrazol-1-yl]benzenesulfonamide;

4-[5-(4-(N,N-diethylamino)-3-methylphenyl)-3-(trifluoromethyl)-1H-pyrazol-1-yl]benzenesulfonamide;

N-[4-[1-[4-(aminosulfonyl)phenyl]-3-(trifluoromethyl)-1H-pyrazol-5-yl]-3-fluorophenyl]-N-methylacetamide;

N-[4-[1-[4-(aminosulfonyl)phenyl]-3-(trifluoromethyl)-1H-pyrazol-5-yl]-3-chlorophenyl]-N-methylacetamide;

N-[4-[1-[4-(aminosulfonyl)phenyl]-3-(trifluoromethyl)-1H-pyrazol-5-yl]-3-methylphenyl]-N-methylacetamide;

N-[4-[1-[4-(aminosulfonyl)phenyl]-3-(trifluoromethyl)-1H-pyrazol-5-yl]-3-fluorophenyl]-N-methylurea;

N-[4-[1-[4-(aminosulfonyl)phenyl]-3-(trifluoromethyl)-1H-pyrazol-5-yl]-3-chlorophenyl]-N-methylurea;

N-[4-[1-[4-(aminosulfonyl)phenyl]-3-(trifluoromethyl)-1H-pyrazol-5-yl]-3-methylphenyl]-N-methylurea;

N-[4-[1-[4-(aminosulfonyl)phenyl]-3-(trifluoromethyl)-1H-pyrazol-5-yl]-3-fluorophenyl]-N-methylthiourea;

N-[4-[1-[4-(aminosulfonyl)phenyl]-3-(trifluoromethyl)-1H-pyrazol-5-yl]-3-chlorophenyl]-N-methylthiourea;

N-[4-[1-[4-(aminosulfonyl)phenyl]-3-(trifluoromethyl)-1H-pyrazol-5-yl]-3-methylphenyl]-N-methylthiourea;

4-[5-(3-(N,N-dimethylamino)phenyl)-3-(trifluoromethyl)-1H-pyrazol-1-yl]benzenesulfonamide;

4-[5-(3-(N-ethyl-N-methylamino)phenyl)-3-(trifluoromethyl)-1H-pyrazol-1-yl]benzenesulfonamide;

4-[5-(4-chloro-3-(N-methylamino)phenyl)-3-(trifluoromethyl)-1H-pyrazol-1-yl]benzenesulfonamide;

4-[5-(4-methyl-3-(N-methylamino)phenyl)-3-(trifluoromethyl)-1H-pyrazol-1-yl]benzenesulfonamide;

N-3-[1-[4-(aminosulfonyl)phenyl]-3-(trifluoromethyl)-1H-pyrazol-5-yl]phenyl]-N-methylacetamide;

N-3-[1-[4-(aminosulfonyl)phenyl]-3-(trifluoromethyl)-1H-pyrazol-5yl]-4-fluorophenyl]-N-methylacetamide;

N-3-[1-[4-(aminosulfonyl)phenyl]-3-(trifluoromethyl)-1H-pyrazol-5-yl]-4- methylphenyl]-N-methylurea;

N-3-[1-[4-(aminosulfonyl)phenyl]-3-(trifluoromethyl)-1H-pyrazol-5-yl]-4-fluorophenyl]-N-methylthiourea;

4-[5-(2-(N-ethyl-N-methylamino)-4-methylphenyl)-3-(trifluoromethyl)-1H-pyrazol-1-yl]benzenesulfonamide;

N-2-[1-[4-(aminosulfonyl)phenyl]-3-(trifluoromethyl)-1H-pyrazol-5-yl]-4-methylphenyl]-N-methylurea;

N-2-[1-[4-(aminosulfonyl)phenyl]-3-(trifluoromethyl)-1H-pyrazol-5-yl]-4-fluorophenyl]-N-methylthiourea;

4-[5-(1H-indol-5-yl)-3-(trifluoromethyl)-1H-pyrazol-1yl]benzenesulfonamide;

4-[5-(7-fluoro-1H-indol-5-yl)-3-(trifluoromethyl)-1H-pyrazol-1-yl]benzenesulfonamide;

4-[5-(1-ethyl-1H-indol-5-yl)-3-(trifluoromethyl)-1H-pyrazol-1-yl]benzenesulfonamide;

4-[5-(7-methyl-1H-indol-5-yl)-3-(trifluoromethyl)-1H-pyrazol-1-yl]benzenesulfonamide;

4-[5-(7-chloro-1-methyl-1H-indol-5-yl)-3-(trifluoromethyl)-1H-pyrazol-1-yl]benzenesulfonamide;

4-[5-(2,3-dihydro-1H-indol-5-yl)-3-(trifluoromethyl)-1H-pyrazol-1-yl]benzenesulfonamide;

4[5-(7-fluoro-1-methyl-2,3-dihydro-1H-indol-5-yl)-3-(trifluoromethyl)-1H-pyrazol-1-yl]benzenesulfonamide;

4-[3-aminomethyl-5-phenyl-1H-pyrazol-1-yl]benzenesulfonamide;

4-[3-(N-methylamino)methyl-5-phenyl-1H-pyrazol-1-yl]benzenesulfonamide;

4-[3-(N,N-dimethylamino)methyl-5-phenyl-1H-pyrazol-1-yl]benzenesulfonamide;

4-[5-phenyl-3-(N-phenylamion)methyl-1H-pyrazol-1-yl]benzenesulfonamide;

4-[3-(N-benzylamino)methyl-5-phenyl-1H-pyrazol-1-yl]benzenesulfonamide;

4-[3-(N-benzyl-N-methylamino)methyl-5-phenyl-1H-pyrazol-1-yl]benzenesulfonamide;

4-[3-(N-methyl-N-phenylamino)methyl-5-phenyl-1H-pyrazol-1-yl]benzenesulfonamide;

N-[[1-[4-(aminosulfonyl)phenyl]-5-phenyl-1H-pyrazol-3-yl]methyl]acetamide;

N-[[1-[4-(aminosulfonyl)phenyl]-5-phenyl-1H-pyrazol-3yl]methyl]-N-methylacetamide;

N-[[1-[4-(aminosulfonyl)phenyl]-5-phenyl-1H-pyrazol-3-yl]methyl]-N-phenylacetamide;

N-[[1-[4-(aminosulfonyl)phenyl]-5-phenyl-1H-pyrazol-3-yl]methyl]-N-benzylacetamide;

N-[[1-[4-(aminosulfonyl)phenyl]-5-phenyl-1H-pyrazol-3-yl]methyl]urea;

N-[[1-[4-(aminosulfonyl)phenyl]-5-phenyl-1H-pyrazol-3-yl]methyl]-N-methylurea;

N-[[1-[4-(aminosulfonyl)phenyl]-5-phenyl-1H-pyrazol-3-yl]methyl]-N-phenylurea;

N-[[1-[4-(aminosulfonyl)phenyl]-5-phenyl-1H-pyrazol-3-yl]methyl]-N-benzylurea;

N-[[1-[4-(aminosulfonyl)phenyl]-5-phenyl-1H-pyrazol-3-yl]methyl]thiourea;

N-[[1-[4-(aminosulfonyl)phenyl]-5-phenyl-1H-pyrazol-3-yl]methyl]-N-methylthiourea;

N-[[1-[4-(aminosulfonyl)phenyl]-5-phenyl-1H-pyrazol-3-yl]methyl]-N-phenylthiourea;

N-[[1-[4-(aminosulfonyl)phenyl]-5-phenyl-1H-pyrazol-3-yl]methyl]-N-benzylthiourea;

4-[4-methoxy-5-phenyl-3-(trifluoromethyl)-1H-pyrazol-1-yl]benzenesulfonamide;

4-[4-methylthio-5-phenyl-3-(trifluoromethyl)-1H-pyrazol-1-yl]benzenesulfonamide;

4-[4-(N-methylamino)-5-phenyl-3-(trifluoromethyl)-1H-pyrazol-1-yl]benzenesulfonamide;

4-[4-(N,N-dimethylamino)-5-phenyl-3-(trifluoromethyl)-1H-pyrazol-1-yl]benzenesulfonamide;

4-[3-methoxy-5-phenyl-1H-pyrazol-1-yl]benzenesulfonamide;

4-[3-ethoxy-5-phenyl-1H-pyrazol-1-yl]benzenesulfonamide;

4-[3-phenoxy-5-phenyl-1H-pyrazol-1-yl]benzenesulfonamide;

4-[3-benzyloxy-5-phenyl-1H-pyrazol-1-yl]benzenesulfonamide;

4-[3-methylthio-5-phenyl-1H-pyrazol-1-yl]benzenesulfonamide;

4-[3-benzylthio-5-phenyl-1H-pyrazol-1-yl]benzenesulfonamide;

4-[3-(N-methylamino)-5-phenyl-1H-pyrazol-1-yl]benzenesulfonamide;

4-[3-(N,N-dimethylamino)-5-phenyl-1H-pyrazol-1-yl]benzenesulfonamide;

4[3-(N-benzyl-N-methylamino)-5-phenyl-1H-pyrazol-1-yl]benzenesulfonamide;

N-[1-[4-(aminosulfonyl)phenyl]-5-phenyl-1H-pyrazol-3-yl]acetamide;

N-[1-[4-(aminosulfonyl)phenyl]-5-phenyl-1H-pyrazol-3-yl]-N-benzylacetamide;

N-[1-[4-(aminosulfonyl)phenyl]-5-phenyl-1H-pyrazol-3-yl]-N-benzylacetamide;

N-[1-[4-(aminosulfonyl)phenyl]-5-phenyl-1H-pyrazol-3-yl]urea;

N-[1-[4-(aminosulfonyl)phenyl]-5-phenyl-1H-pyrazol-3-yl]-N-methylurea;
N-[1-[4-(aminosulfonyl)phenyl]-5-phenyl-1H-pyrazol-3-yl]-N-benzylurea;
N-[1-[4-(aminosulfonyl)phenyl]-5-phenyl-1H-pyrazol-3-yl] thiourea;
N-[1-[4-(aminosulfonyl)phenyl]-5-phenyl-1H-pyrazol-3-yl]-N-methylthiourea;
N-[1-[4-(aminosulfonyl)phenyl]-5-phenyl-1H-pyrazol-3-yl]-N-benzylthiourea;
4-[5-phenyl-3-(1,1-difluoro-1-phenylmethyl)-1H-pyrazol-1-yl]benzenesulfonamide;
4-[5-phenyl-3-(1,1-difluoro-2-phenylethyl)-1H-pyrazol-1-yl]benzenesulfonamide;
1-[4-(aminosulfonyl)phenyl]-5-phenyl-1H-pyrazole-3-difluoroacetic acid;
methyl 1-[4-(aminosulfonyl)phenyl]-5-phenyl-1H-pyrazole-3-difluoroacetate;
1-[4-(aminosulfonyl)phenyl]-5-phenyl-1H-pyrazole-3-difluoroacetamide;
N,N-dimethyl-1-[4-(aminosulfonyl)phenyl]-5-phenyl-1H-pyrazole-3-difluoroacetamide;
N-phenyl-1-[4-(aminosulfonyl)phenyl]-5-phenyl-1H-pyrazole-3-difluoroacetamide;
1-[4-(aminosulfonyl)phenyl]-5-phenyl-1H-pyrazole-3-acetic acid;
1-[4-(aminosulfonyl)phenyl]-4-chloro-5-phenyl-1H-pyrazole-3-difluoroacetic acid;
1-[4-(aminosulfonyl)phenyl]-4-bromo-5-phenyl-1H-pyrazole-3-difluoroacetic acid;
1-[4-(aminosulfonyl)phenyl]-4-chloro-5-(4-chlorophenyl)-1H-pyrazole-3-acetic acid;
1-[4-(aminosulfonyl)phenyl]-4-bromo-5-phenyl-1H-pyrazole-3-acetic acid;
(R)-2-[1-[4-(amiosulfonyl)phenyl]-5-phenyl-1H-pyrazol-3-yl]propanoic acid;
(S)-2-[1-[4-(aminosulfonyl)phenyl]-5-phenyl-1H-pyrazol-3-yl]propanoic acid;
(R)-2-[1-[4-(aminosulfonyl)phenyl]-4-chloro-5-phenyl-1H-pyrazol-3-yl]propanoic acid;
(S)-2-[1-[4-(aminosulfonyl)phenyl]-4-chloro-5-phenyl-1H-pyrazol-3-yl]propanoic acid;
(R)-2-[1-[4-(aminosulfonyl)phenyl]-4-bromo-5-phenyl-1H-pyrazol-3-yl]propanoic acid;
(S)-2-[1-[4-(aminosulfonyl)phenyl]-4-bromo-5-phenyl-1H-pyrazol-3-yl]propanoic acid;
2-[1-[4-(aminosulfonyl)phenyl]-5-phenyl-1H-pyrazol-3-yl]-2-methylpropanoic acid;
2-[1-[4-(aminosulfonyl)phenyl]-4-phenyl-1H-pyrazol-3-yl] methylpropanoic acid;
2-[1-[4-(aminosulfonyl)phenyl]-4-bormo-5-phenyl-1H-pyrazol-3-yl]-2-methylpropanoic acid;
2-fluoro-4-[5-phenyl-3-(trifluoromethyl)-1H-pyrazol-1-yl] benzenesulfonamide;
3-fluoro-4-[5-phenyl-3-(trifluoromethyl)-1H-pyrazol-1-yl] benzenesulfonamide;
2-methyl-4-[5-phenyl-3-(trifluoromethyl)-1H-pyrazol-1-yl] benzenesulfonamide;
3-methyl-4-[5-phenyl-3-(trifluoromethyl)-1H-pyrazol-1-yl] benzenesulfonamide;
ethyl 1-[4-(aminosulfonyl)phenyl]-5-(4-chlorophenyl)-1H-pyrazole-3-carboxylate;
ethyl 1-[4-(aminosulfonyl)phenyl]-5-(4-methylphenyl)-1H-pyrazole-3-carboxylate;
isopropyl 1-[4-(aminosulfonyl)phenyl]-5-(4chlorophenyl)-1H-pyrazole-3-carboxylate;
methyl-1-[4-(aminosulfonyl)phenyl]-5-(4-aminophenyl)-1H-pyrazole-3-carboxylate;
1-[4-(aminosulfonyl)phenyl]-5-(4-chlorophenyl)-1H-pyrazole-3-carboxylic acid;
tert-butyl-1-[4-(aminosulfonyl)phenyl]-5-(4-chlorophenyl)-1H-pyrazole-3-carboxylate;
propyl-1-[4-(aminosulfonyl)phenyl]-5-(4-chlorophenyl)-1H-pyrazole-3-carboxylate;
butyl-1[4-(aminosulfonyl)phenyl]-5-(4-chlorophenyl)-1H-pyrazole-3-carboxylate;
isobutyl-1-[4-(aminosulfonyl)phenyl]-5-(4-chlorophenyl)-1H-pyrazole-3carboxylate;
pentyl-1-[4-(aminosulfonyl)phenyl]-5-(4-chlorophenyl)-1H-pyrazole-3-carboxylate;
methyl-1-[4-(aminosulfonyl)phenyl]-5-(4-chlorophenyl)-1H-pyrazole-3-carboxylate;
methyl-1-[4-(aminosulfonyl)phenyl]-5-(4-methylphenyl)-1H-pyrazole-3-carboxylate;
methyl-1-[4-(aminosulfonyl)phenyl]-5-(4-methoxyphenyl)-1H-pyrazole-3-carboxylate;
methyl-1-[4-(aminosulfonyl)phenyl]-5-(4-bromophenyl)-1H-pyrazole-3-carboxylate;
methyl-1-[4-(aminosulfonyl)phenyl]-5-(4-nitrophenyl)-1H-pyrazole-3-carboxylate;
methyl-1-[4-(aminosulfonyl)phenyl]-5-(4-fluorophenyl)-1H-pyrazole-3-carboxylate;
methyl-1-[4-(aminosulfonyl)phenyl]-5-(3,5-dichloro-4-methoxyphenyl-1H-pyrazole-3-carboxylate;
methyl-1-[4-(aminosulfonyl)phenyl]-5-(3,5-difluoro-4-methoxyphenyl)-1H-pyrazole-3-carboxylate;
N-[4-methylphenyl]-1-[4-(aminosulfonyl)phenyl]-5-(4-fluorophenyl)-1H-pyrazole-3-carboxamide;
N-[3-chlorophenyl]-1-[4-aminosulfonyl)phenyl]-5-(4-fluorophenyl)-1H-pyrazole-3-carboxamide;
N-[3-fluorophenyl]-1-[4-(aminosulfonyl)phenyl]-5-(4-fluorophenyl)-1H-pyrazole-3-carboxamide;
N-[3-fluorophenyl]-1-[4-(aminosulfonyl)phenyl]-5-(4-chlorophenyl)-1H-pyrazole-3-carboxamide;
phenylmethyl N-[[1-[4-(aminosulfonyl)phenyl]-5-(4-chlorophenyl)-1H-pyrazol-3-yl]carbonyl]glycinate;
1-[4-(aminosulfonyl)phenyl]-5-(4-bromophenyl)-1H-pyrazole-3-carboxamide;
1-[4-(aminosulfonyl)phenyl]-5-(4-chlorophenyl)-1H-pyrazole-3-carboxamide;
N-phenyl-1-[4-(aminosulfonyl)phenyl]-5-(4-fluorophenyl)-1H-pyrazole-3-carboxamide;
N-(4-methoxyphenyl)-1-[4-(aminosulfonyl)phenyl]-5-(4-fluorophenyl)-1H-pyrazole-3-carboxamide;
N-(4-methylphenyl)-1-[4-(aminosulfonyl)phenyl]-5-(4-chlorophenyl)-1H-pyrazole-3-carboxamide;
N,N-dimethyl-1-[4-(aminosulfonyl)phenyl]-5-(4-chlorophenyl)-1H-pyrazole-3-carboxamide;
N-methyl-1-[4-(aminosulfonyl)phenyl]-5-(4-chlorophenyl)-1H-pyrazole-3-carboxamide;
N-methyl-N-ethyl-1-[4-(aminosulfonyl)phenyl]-5-(4-chlorophenyl)-1H-pyrazole-3-carboxamide;
N-phenyl-1-[4-(aminosulfonyl)phenyl]-5-(4-chlorophenyl)-1H-pyrazole-3-carboxamide;
N-methyl-N-phenyl-1-[4-(aminosulfonyl)phenyl]-5-(4-chlorophenyl)-1H-pyrazole-3-carboxamide;
N-ethyl-1-[4-(aminosulfonyl)phenyl]-5-(4-chlorophenyl)-1H-pyrazole-3-carboxamide;
N-isopropyl-1-[4-(aminosulfonyl)phenyl]-5-(4-chlorophenyl)-1H-pyrazole-3-carboxamide;
N-propyl-1-[4-(aminosulfonyl)phenyl]-5-(4-chlorophenyl)-1H-pyrazole-3-carboxamide;
N-butyl-1[4-(aminosulfonyl)phenyl]-5-(4-chlorophenyl)-1H-pyrazole-3-carboxyamide;
N-isobutyl-1-[4-(aminosulfonyl)phenyl]-5-(4-chorophenyl)-1H-pyrazole-3-carboxamide;

N-tert-butyl-1-[4-(aminosulfonyl)phenyl]-5-(4-chlorophenyl)-1H-pyrazole-3-carboxyamide;
N-pentyl-1-[4-(aminosulfonyl)phenyl]-5-(4-chlorophenyl)-1H-pyrazole-3-carboxyamide;
N-cyclohexyl-1-[4-(aminosulfonyl)phenyl]5-(4-fluorophenyl)-1H-pyrazole-3-carboxamide;
N-cyclopentyl-1-[4-(aminosulfonyl)phenyl]5-(4-chlorophenyl)-1H-pyrazoel-3-carboxyamide;
4-[5(4-chlorophenyl)-3-(pyrrolidinocarboxamide)-1H-pyrazol-1yl]benzenesulfonamide;
4-[5-(4-chlorophenyl)-3-(piperidinocarboxamide)-1H-pyrazol-1-yl]benzenesulfonamide;
N-(3-chlorophenyl)-1-[4-(aminosulfonyl)phenyl]-5-(4-chlorophenyl)-1H-pyrazole-3-carboxamide;
N-(2-pyridyl)-1-[4-(aminosulfonyl)phenyl]5-(4-chlorophenyl)-1H-pyrazole-3-carboxamide;
N-methyl-N-(3chlorophenyl)-1-[4-(aminosulfonyl)phenyl]-5-(4-chlorophenyl)-1H-pyrazole-3-carboxamide;
1-[4-(aminosulfonyl)phenyl]-5-(4-nitrophenyl)-1H-pyrazole-3-carboxamide;
1-[4-(aminosulfonyl)phenyl]-5-(4-fluorophenyl)-1H-pyrazole-3-carboxamide;
1-[4-(aminosulfonyl)phenyl]-5-phenyl-1H-pyrazole-3-carboxamide;
1-[4-(aminosulfonyl)phenyl]-5-(3-chloro-4-methoxyphenyl)-1H-pyrazole-3-carboxamide;
1-[4-(aminosulfonyl)phenyl]-5-(4-methylthiophenyl)-1H-pyrazole-3-carboxamide;
1-[4-(aminosulfonyl)phenyl]-5-(4-methoxyphenyl)-1H-pyrazole-3-carboxamide;
1-[4-(aminosulfonyl)phenyl]-5-(4-methylphenyl)-1H-pyrazole-3-carboxamide;
N-methyl 1-[4-(aminosulfonyl)phenyl]-5-(4-methoxyphenyl)-1H-pyrazole-3-carboxamide;
N-[[1-[4-(aminosulfonyl)phenyl]-5-(4-chlorophenyl)-1H-pyrazol-3-yl]carbonyl]glycine;
1-[4-(aminosulfonyl)phenyl]-5-(3-bromo-4-methoxyphenyl)-1H-pyrazole-3-carboxamide;
1-[4-(aminosulfonyl)phenyl]-5-(3,5-dichloro-4-methoxyphenyl)-1H-pyrazole-3-carboxamide;
4-[5-(4-bromophenyl)-3-cyano-1H-pyrazol-1-yl]benzenesulfonamide;
4-[3-cyano-5-(4-fluorophenyl)-1H-pyrazol-1-yl]benzenesulfonamide;
4-[5-(4-chlorophenyl)-3-cyano-1H-pyrazol-1-yl]benzenesulfonamide;
4-[3-cyano-5-(4-methoxyphenyl)-1H-pyrazol-1-yl]benzenesulfonamide;
4-[3-cyano-5-(4-methylphenyl)-1H-pyrazol-1-yl]benzenesulfonamide;
4-[3-cyano-5-(4-methylthiophenyl)-1H-pyrazol-1-yl]benzenesulfonamide;
4-[5-(3-chloro-4-methoxyphenyl)-3-cyano-1H-pyrazol-1-yl]benzenesulfonamide;
4-[5-(3,5-dichloro-4-methoxyphenyl)-3-cyano-1H-pyrazol-1-yl]benzenesulfonamide;
4-[5-(3-bromo-4-methoxyphenyl)-3-cyano-1H-pyrazol-1-yl]benzenesulfonamide;
4-[3-cyano-5-phenyl-1H-pyrazol-1-yl]benzenesulfonamide;
4-[5-(4-nitrophenyl)-3-(cyano)-1H-pyrazol-1-yl]benzenesulfonamide;
4-[4-chloro-5-(4-fluorophenyl)-1H-pyrazol-1-yl]benzenesulfonamide;
4-[4-chloro-5-(4-chlorophenyl)-1H-pyrazol-1-yl]benzenesulfonamide;
4-[4-bromo-5-(4-chlorophenyl)-1H-pyrazol-1-yl]benzenesulfonamide;
4-[4-chloro-5-phenyl-1H-pyrazol-1-yl]benzenesulfonamide;
4-[4-chloro-5-(3,5-dichloro-4-methoxyphenyl)-1H-pyrazol-1-yl]benzenesulfonamide;
4-[4-bromo-5-(4-methylphenyl)-1H-pyrazol-1-yl]benzenesulfonamide;
4-[4-chloro-5-(4-methylphenyl)-1H-pyrazol-1-yl]benzenesulfonamide;
4-[4-chloro-5-(3-chloro-4-methoxyphenyl)-1H-pyrazol-1-yl]benzenesulfonamide;
4-[4chloro-5-(4-methoxyphenyl)-1H-pyrazol-1-yl]benzenesulfonamide;
4-[4-bromo-5-(4-methoxyphenyl)-1H-pyrazol-1-yl]benzenesulfonamide;
4-[4-cyano-5-(4-methoxyphenyl)-1H-pyrazol-1-yl]benzenesulfonamide;
4-[4-5-(3,5-difluoro-4-methoxyphenyl)-1H-pyrazol-1-yl]benzenesulfonamide;
4-[4-methyl-5-phenyl-1H-pyrazol-1-yl]
4-[4-fluoro-5-phenyl-1H-pyrazol-1-yl]benzenesulfonamide;
4-[5-(4-chlorophenyl)-4-methylsulfonyl-1H-pyrazol-1-yl]benzenesulfonamide;
4-[4-chloro-5-(4-chlorophenyl)-3-(trifluoromethyl)-1H-pyrazol-1-yl]benzenesulfonamide;
4-[4-ethyl-5-phenyl-3-(trifluoromethyl)-1H-pyrazol-1-yl]benzenesulfonamide;
4-[4-methyl-5-phenyl-3-(trifluoromethyl)-1H-pyrazol-1-yl]benzenesulfonamide;
4-[5-(4-methoxyphenyl)-4-methyl-3-(trifluoromethyl)-1H-pyrazol-1-yl]benzenesulfonamide;
4-[5-(4-chlorophenyl)-4-methyl-3-(trifluoromethyl)-1H-pyrazol-1-yl]benzenesulfonamide; 4-[5-(4-chlorophenyl)-4-ethyl-3-(trifluoromethyl)-1H-pyrazol-1-yl]benzenesulfonamide;
4-[4-ethyl-5-(4-methylphenyl)-3-(trifluoromethyl)-1H-pyrazol-1-yl]benzenesulfonamide;
4-[4-ethyl-5-(4-methoxy-3-methylphenyl)-3-(trifluoromethyl)-1H-pyrazol-1-yl]benzenesulfonamide;
4-[4-ethyl-5-(4-methoxyphenyl)-3-(trifluoromethyl)-1H-pyrazol-1-yl]benzenesulfonamide;
4-[4-cyclopropyl-5-phenyl-3-(trifluoromethyl)-1H-pyrazol-1-yl]benzenesulfonamide;
4-[4-ethyl-5-(3-fluoro-4-chlorophenyl)-3-(trifluoromethyl)-1H-pyrazol-1-yl]benzenesulfonamide;
4-[4-hydroxymethyl-5-phenyl-3-(trifluoromethyl)-1H-pyrazol-1-yl]benzenesulfonamide;
4-[5-(4-fluorophenyl)-4-methyl-3-(trifluoromethyl)-1H-pyrazol-1-yl]benzenesulfonamide;
4-[4-methyl-5-(4-methylphenyl)-3-(trifluoromethyl)-1H-pyrazol-1-yl]benzenesulfonamide;
4-[4-fluoro-5-phenyl-3-(trifluoromethyl)-1H-pyrazol-1-yl]benzenesulfonamide;
4-[4-bromo-5-(4-chlorophenyl)-3-(difluoromethyl)-1H-pyrazol-1-yl]benzenesulfonamide;
4-[4-chloro-5-(3,5-dichloro-4-methoxyphenyl)-3-(difluoromethyl)-1H-pyrazol-1-yl]benzenesulfonamide;
4-[4-chloro-3-(difluoromethyl)-5-phenyl-1H-pyrazol-1-yl]benzenesulfonamide;
4-[4-bromo-3-(difluoromethyl)-5phenyl-1H-pyrazol-1-yl]benzenesulfonamide;
4-[4-chloro-3-(difluoromethyl)-5-(4-methoxyphenyl)-1H-pyrazol-1-yl]benzenesulfonamide;
4-[4-chloro-3-cyano-5-phenyl-1H-pyrazol-1-yl]benzenesulfonamide;
4-[4-chloro-5-(4-chlorophenyl)-3-cyano-1H-pyrazol-1-yl]benzenesulfonamide;

4-[4-chloro-3-cyano-5-(4-fluorophenyl)-1H-pyrazol-1-yl]
benzenesulfonamide;
4-[4-bromo-3-cyano-5-(4-fluorophenyl)-1H-pyrazol-1-yl]
benzenesulfonamide;
4-[4-bromo-3-cyano-5-phenyl-1H-pyrazol-1-yl]
benzenesulfonamide;
ethyl [1-(4-aminosulfonylphenyl)-4-bromo-5-[4-chlorophenyl)-1H-pyrazol-3-yl]carboxylate;
methyl [1-(4-aminosulfonylphenyl)-4-chloro-5-phenyl-1H-pyrazol-3-yl]carboxylate;
methyl [1-(4-aminosulfonylphenyl)-4-chloro-5-(4-chlorophenyl)-1H-pyrazol-3-yl]carboxylate;
ethyl [1-(4-aminosulfonylphenyl)-4-chloro-5-(4-chlorophenyl)-1H-pyrazol-3-yl]carboxylate;
methyl [1-(4-aminosulfonylphenyl)-4-chloro-5-(4-fluorophenyl)-1H-pyrazol-3-yl]carboxylate;
methyl [1-(4-aminosulfonylphenyl)-4-bromo-5-(4-fluorophenyl)-1H-pyrazol-3-yl]carboxylate;
methyl [1-(4-aminosulfonylphenyl)-4-chloro-5-(3-chloro-4-methoxyphenyl)-1H-pyrazol-3-yl]carboxylate;
methyl [1-(4-aminosulfonylphenyl)-4-chloro-5-(3,5-dichloro-4-methoxyphenyl)-1H-pyrazol-3-yl]carboxylate;
methyl [1-(4-aminosulfonylphenyl)-5-(3-bromo-4-methoxyphenyl)-4-chloro-1H-pyrazol-3-yl]carboxylate;
[1-(4-aminosulfonylphenyl)-4-chloro-5-phenyl-1H-pyrazol-3-yl]carboxamide;
[1-(4-aminosulfonylphenyl)-4-chloro-5-(4-chlorophenyl)-1H-pyrazol-3-yl]carboxamide;
[1-(4-aminosulfonylphenyl)-4-chloro-5-(4-fluorophenyl)-1H-pyrazol-3-yl]carboxamide;
[1-(4-aminosulfonylphenyl)-4-bromo-5-(4-chlorophenyl)-1H-pyrazol-3-yl]carboxamide;
[1-(4-aminosulfonylphenyl)-4-bromo-5-phenyl-1H-pyrazol-3-yl]carboxamide;
[1-(4-aminosulfonylphenyl)-4-chloro-5-(4-chlorophenyl)-1H-pyrazol-3-yl]carboxylic acid;
[1-(4-aminosulfonylphenyl)-4-chloro-5-phenyl-1H-pyrazol-3-yl]carboxylic acid;
[1-(4-aminosulfonylphenyl)-4-chloro-5-(3,5-dichloro-4-methoxyphenyl)-1H-pyrazol-3-yl]carboxylic acid;
4-[4-chloro-3-isopropyl-5-phenyl-1H-pyrazol-1-yl]benzenesulfonamide;
4-[4-chloro-3-methyl-5-phenyl-1H-pyrazol-1-yl]benzenesulfonamide;
4-[4-chloro-3-hydroxymethyl-5-phenyl-1H-pyrazol-1-yl]benzenesulfonamide;
4-[4-chloro-5-(4-chlorophenyl)-3-hydroxymethyl-1H-pyrazol-1-yl]benzenesulfonamide;
[1-(4-aminosulfonylphenyl)-4-chloro-5-(4-chlorophenyl)-1H-pyrazol-3-yl]propanoic acid;
4-[5-(4-chlorophenyl)-3-(trifluoromethyl)-1H-pyrazol-1-yl]benzenesulfonamide;
4-[5-phenyl-3-(trifluoromethyl)-1H-pyrazol-1-yl]benzenesulfonamide;
4-[5-(4-fluorophenyl)-3-(trifluoromethyl)-1H-pyrazol-1-yl]benzenesulfonamide;
4-[5-(4-cyanophenyl)-3-(trifluoromethyl)-1H-pyrazol-1-yl]benzenesulfonamide;
4-[5-(2,4-difluorophenyl)-3-(trifluoromethyl)-1H-pyrazol-1-yl]benzenesulfonamide;
4-[5-(2,6-difluorophenyl)-3-(trifluoromethyl)-1H-pyrazol-1-yl]benzenesulfonamide;
4-[5-(4-methoxyphenyl)-3-(trifluoromethyl)-1H-pyrazol-1-yl]benzenesulfonamide;
4-[5-(3,4-dichlorophenyl)-3-(trifluoromethyl)-1H-pyrazol-1-yl]benzenesulfonamide;
4-[5-(4-bromophenyl)-3-(trifluoromethyl)-1H-pyrazol-1-yl]benzenesulfonamide;
4-[5-(2,4-dichlorophenyl)-3-(trifluoromethyl)-1H-pyrazol-1-yl]benzenesulfonamide;
4-[5-(3-chlorophenyl)-3-(trifluoromethyl)-1H-pyrazol-1-yl]benzenesulfonamide;
4-[5-(4-methylphenyl)-3-(trifluoromethyl)-1H-pyrazol-1-yl]benzenesulfonamide;
4-[5-(4-trifluoromethylphenyl)-3-(trifluoromethyl)-1H-pyrazol-1-yl]benzenesulfonamide;
4-[5-(4-trifluoromethoxyphenyl)-3-(trifluoromethyl)-1H-pyrazol-1-yl]benzenesulfonamide;
4-[5-(4-nitrophenyl)-3-(trifluoromethyl)-1H-pyrazol-1-yl]benzenesulfonamide;
4-[5-(2-chlorophenyl)-3-(trifluoromethyl)-1H-pyrazol-1-yl]benzenesulfonamide;
4-[5-(2-fluorophenyl)-3-(trifluoromethyl)-1H-pyrazol-1-yl]benzenesulfonamide;
4-[5-(4-aminophenyl)-3-(trifluoromethyl)-1H-pyrazol-1-yl]benzenesulfonamide;
4-[5-(2-methylphenyl)-3-(trifluoromethyl)-1H-pyrazol-1-yl]benzenesulfonamide;
4-[5-(4-fluoro-2-methylphenyl)-3-(trifluoromethyl)-1H-pyrazol-1-yl]benzenesulfonamide;
4-[5-(3-methylphenyl)-3-(trifluoromethyl)-1H-pyrazol-1-yl]benzenesulfonamide;
4-[5-(4-ethoxyphenyl)-3-(trifluoromethyl)-1H-pyrazol-1-yl]benzenesulfonamide;
4-[5-(3,5-dimethyl-4-methoxyphenyl)-3-(trifluoromethyl)-1H-pyrazol-1-yl]benzenesulfonamide;
4-[5-(3-fluorophenyl)-3-(trifluoromethyl)-1H-pyrazol-1-yl]benzenesulfonamide;
4-[5-(3-fluoro-4-methoxyphenyl)-3-(trifluoromethyl)-1H-pyrazol-1-yl]benzenesulfonamide;
4-[5-(4-methylthiophenyl)-3-(trifluoromethyl)-1H-pyrazol-1-yl]benzenesulfonamide;
4-[5-(4-chloro-3-methylphenyl)-3-(trifluoromethyl)-1H-pyrazol-1-yl]benzenesulfonamide;
4-[5-(4-ethylphenyl)-3-(trifluoromethyl)-1H-pyrazol-1-yl]benzenesulfonamide;
4-[5-(2,4-dimethylphenyl)-3-(trifluoromethyl)-1H-pyrazol-1-yl]benzenesulfonamide;
4-[5-(2-methoxyphenyl)-3-(trifluoromethyl)-1H-pyrazol-1-yl]benzenesulfonamide;
4-[5-(4-methoxy-3-methylphenyl)-3-(trifluoromethyl)-1H-pyrazol-1-yl]benzenesulfonamide;
4-[5-(3-bromo-4-methylthiophenyl)-3-(trifluoromethyl)-1H-pyrazol-1-yl]benzenesulfonamide;
4-[5-(4-hydroxy-3-methylphenyl)-3-(trifluoromethyl)-1H-pyrazol-1-yl]benzenesulfonamide;
4-[5-(3-chloro-4-methylphenyl)-3-(trifluoromethyl)-1H-pyrazol-1-yl]benzenesulfonamide;
4-[5-(3,4-dimethoxyphenyl)-3-(trifluoromethyl)-1H-pyrazol-1-yl]benzenesulfonamide;
4-[5-(3-chloro-4-methoxyphenyl)-3-(trifluoromethyl)-1H-pyrazol-1-yl]benzenesulfonamide;
4-[5-(3-chloro-4-methoxy-5-methylphenyl)-3-(trifluoromethyl)-1H-pyrazol-1-yl]benzenesulfonamide;
4-[5-(3-ethyl-4-methoxyphenyl)-3-(trifluoromethyl)-1H-pyrazol-1-yl]benzenesulfonamide;
4-[5-(4-fluoro-2-methoxyphenyl)-3-(trifluoromethyl)-1H-pyrazol-1-yl]benzenesulfonamide;
4-[5-(4-hydroxymethylphenyl)-3-(trifluoromethyl)-1H-pyrazol-1-yl]benzenesulfonamide;
4-[5-(4-methoxy-3-(1-propenyl)phenyl)-3-(trifluoromethyl)-1H-pyrazol-1-yl]benzenesulfonamide;
4-[5-(3,5-dichloro-4-methoxyphenyl)-3-(trifluoromethyl)-1H-pyrazol-1-yl]benzenesulfonamide;

4-[5-(2,4-dimethoxyphenyl)-3-(trifluoromethyl)-1H-pyrazol-1-yl]benzenesulfonamide;
4-[5-(3-chloro-4-fluorophenyl)-3-(trifluoromethyl)-1H-pyrazol-1-yl]benzenesulfonamide;
4-[5-(4-methoxy-3-propylphenyl)-3-(trifluoromethyl)-1H-pyrazol-1-yl]benzenesulfonamide;
4-[5-(3,5-difluoro-4-methoxyphenyl)-3-(trifluoromethyl)-1H-pyrazol-1-yl]benzenesulfonamide;
4-[5-(3-fluoro-4-methylthiophenyl)-3-(trifluoromethyl)-1H-pyrazol-1-yl]benzenesulfonamide;
4-[5-(3-cyclopropylmethyl-4-methoxyphenyl)-3-(trifluoromethyl)-1H-pyrazol-1-yl]benzenesulfonamide;
4-[1-[4-(aminosulfonyl)phenyl]-3-(trifluoromethyl)-1H-pyrazol-5-yl]benzoic acid;
4-[5-(3-methyl-4-methylthiophenyl)-3-(trifluoromethyl)-1H-pyrazol-1-yl]benzenesulfonamide;
4-[5-(3-chloro-4-methylthiophenyl)-3-(trifluoromethyl)-1H-pyrazol-1-yl]benzenesulfonamide;
4-[5-(4-(N,N-dimethylamino)phenyl)-3-(trifluoromethyl)-1H-pyrazol-1-yl]benzenesulfonamide;
4-[5-(4-methyl-3-nitrophenyl)-3-(trifluoromethyl)-1H-pyrazol-1-yl]benzenesulfonamide;
4-[5-(4-(N-methylamino)phenyl)-3-(trifluoromethyl)-1H-pyrazol-1-yl]benzenesulfonamide;
4-[5-(3-amino-4-methylphenyl)-3-(trifluoromethyl)-1H-pyrazol-1-yl]benzenesulfonamide;
methyl-4-[1-[4-(aminosulfonyl)phenyl]-3-(trifluoromethyl)-1H-pyrazol-5-yl]benzoate;
4-[1-[4-(aminosulfonyl)phenyl]-3-(trifluoromethyl)-1H-pyrazol-5-yl]benzamide;
4-[5-(3,5-difluorophenyl)-3-(trifluoromethyl)-1H-pyrazol-1-yl]benzenesulfonamide;
4-[5-(2,4,6-trifluorophenyl)-3-(trifluoromethyl)-1H-pyrazol-1-yl]benzenesulfonamide;
4-[5-(2,6-dichlorophenyl)-3-(trifluoromethyl)-1H-pyrazol-1-yl]benzenesulfonamide;
4-[5-(2,4,6-trichlorophenyl)-3-(trifluoromethyl)-1H-pyrazol-1-yl]benzenesulfonamide;
4-[5-(3-methoxyphenyl)-3-(trifluoromethyl)-1H-pyrazol-1-yl]benzenesulfonamide;
4-[5-(3,4-dimethylphenyl)-3-(trifluoromethyl)-1H-pyrazol-1-yl]benzenesulfonamide;
4-[5-(1,3-benzodioxol-5-yl)-3-(trifluoromethyl)-1H-pyrazol-1-yl]benzenesulfonamide;
4-[5-(2-fluoro-4-methoxyphenyl)-3-(trifluoromethyl)-1H-pyrazol-1-yl]benzenesulfonamide;
4-[5-(2-chloro-4-methoxyphenyl)-3-(trifluoromethyl)-1H-pyrazol-1-yl]benzenesulfonamide;
4-[5-(4-chloro-2-methoxyphenyl)-3-(trifluoromethyl)-1H-pyrazol-1-yl]benzenesulfonamide;
4-[5-(2-methylthiophenyl)-3-(trifluoromethyl)-1H-pyrazol-1-yl]benzenesulfonamide;
4-[5-(3-methylthiophenyl)-3-(trifluoromethyl)-1H-pyrazol-1-yl]benzenesulfonamide;
4-[5-(2-methylsulfinylphenyl)-3-(trifluoromethyl)-1H-pyrazol-1-yl]benzenesulfonamide;
4-[5-(3-methylsulfinylphenyl)-3-(trifluoromethyl)-1H-pyrazol-1-yl]benzenesulfonamide;
4-[5-(4-methylsulfinylphenyl)-3-(trifluoromethyl)-1H-pyrazol-1-yl]benzenesulfonamide;
4-[5-(2-fluoro-4-methylphenyl)-3-(trifluoromethyl)-1H-pyrazol-1-yl]benzenesulfonamide;
4-[5-(4-fluoro-3-methylphenyl)-3-(trifluoromethyl)-1H-pyrazol-1-yl]benzenesulfonamide;
4-[5-(2-chloro-4-methylphenyl)-3-(trifluoromethyl)-1H-pyrazol-1-yl]benzenesulfonamide;
4-[5-(4-chloro-2-methylphenyl)-3-(trifluoromethyl)-1H-pyrazol-1-yl]benzenesulfonamide;
4-[5-(4-hydroxyphenyl)-3-(trifluoromethyl)-1H-pyrazol-1-yl]benzenesulfonamide;
4-[5-(3,4-dihydroxyphenyl)-3-(trifluoromethyl)-1H-pyrazol-1-yl]benzenesulfonamide;
4-[5-(4-isopropylphenyl)-3-(trifluoromethyl)-1H-pyrazol-1-yl]benzenesulfonamide;
N-[4-[1-[4-(aminosulfonyl)phenyl]-3-trifluoromethyl-1H-pyrazol-5-yl]phenyl]acetamide;
N-[4-[1-[4-(aminosulfonyl)phenyl]-3-trifluoromethyl-1H-pyrazol-5-yl]phenyl]formamide;
N-[4-[1-[4-(aminosulfonyl)phenyl]-3-trifluoromethyl-1H-pyrazol-5-yl]phenyl]trifluoroacetamide;
4-[5-(4-[N-methylaminosulfonyl]phenyl)-3-(trifluoromethyl)-1H-pyrazol-1-yl]benzenesulfonamide;
4-[5-(2,5-dichlorophenyl)-3-(trifluoromethyl)-1H-pyrazol-1-yl]benzenesulfonamide;
4-[5-(4-n-butoxyphenyl)-3-(trifluoromethyl)-1H-pyrazol-1-yl]benzenesulfonamide;
4-[5-(4-[aminosulfonyl]phenyl)-3-(trifluoromethyl)-1H-pyrazol-1-yl]benzenesulfonamide;
4-[5-(2,3-difluorophenyl)-3-(trifluoromethyl)-1H-pyrazol-1-yl]benzenesulfonamide;
4-[5-(2,5-difluorophenyl)-3-(trifluoromethyl)-1H-pyrazol-1-yl]benzenesulfonamide;
4-[5-(2,3,4-trifluorophenyl)-3-(trifluoromethyl)-1H-pyrazol-1-yl]benzenesulfonamide;
4-[5-(3,4,5-trifluorophenyl)-3-(trifluoromethyl)-1H-pyrazol-1-yl]benzenesulfonamide;
4-[5-(2,4,5-trifluorophenyl)-3-(trifluoromethyl)-1H-pyrazol-1-yl]benzenesulfonamide;
4-[5-(2,5,6-trifluorophenyl)-3-(trifluoromethyl)-1H-pyrazol-1-yl]benzenesulfonamide;
4-[5-(2,3,4,5-tetrafluorophenyl)-3-(trifluoromethyl)-1H-pyrazol-1-yl]benzenesulfonamide;
4-[5-(2,3,4,6-tetrafluorophenyl)-3-(trifluoromethyl)-1H-pyrazol-1-yl]benzenesulfonamide;
4-[5-(2,3,5,6-tetrafluorophenyl)-3-(trifluoromethyl)-1H-pyrazol-1-yl]benzenesulfonamide;
4-[5-(pentafluorophenyl)-3-(trifluoromethyl)-1H-pyrazol-1-yl]benzenesulfonamide;
4-[5-(2,3,4-trichlorophenyl)-3-(trifluoromethyl)-1H-pyrazol-1-yl]benzenesulfonamide;
4-[5-(3,4,5-trichlorophenyl)-3-(trifluoromethyl)-1H-pyrazol-1-yl]benzenesulfonamide;
4-[5-(2,4,5-trichlorophenyl)-3-(trifluoromethyl)-1H-pyrazol-1-yl]benzenesulfonamide;
4-[5-(2,5,6-trichlorophenyl)-3-(trifluoromethyl)-1H-pyrazol-1-yl]benzenesulfonamide;
4-[5-(2,3,4,5-tetrachlorophenyl)-3-(trifluoromethyl)-1H-pyrazol-1-yl]benzenesulfonamide;
4-[5-(2,3,4,6-tetrachlorophenyl)-3-(trifluoromethyl)-1H-pyrazol-1-yl]benzenesulfonamide;
4-[5-(2,3,5,6-tetrachlorophenyl)-3-(trifluoromethyl)-1H-pyrazol-1-yl]benzenesulfonamide;
4-[5-(2,3,4,5,6-pentachlorophenyl)-3-(trifluoromethyl)-1H-pyrazol-1-yl]benzenesulfonamide;
4-[5-(4-tert-butylphenyl)-3-(trifluoromethyl)-1H-pyrazol-1-yl]benzenesulfonamide;
4-[5-(4-isobutylphenyl)-3-(trifluoromethyl)-1H-pyrazol-1-yl]benzenesulfonamide;
4-[5-(4-chlorophenyl)-3-(difluoromethyl)-1H-pyrazol-1-yl]benzenesulfonamide;
4-[5-(4-trifluoromethylphenyl)-3-(difluoromethyl)-1H-pyrazol-1-yl]benzenesulfonamide;
4-[5-(4-methylthiophenyl)-3-(difluoromethyl)-1H-pyrazol-1-yl]benzenesulfonamide;
4-[5-(4-(1-morpholino)phenyl)-3-(difluoromethyl)-1H-pyrazol-1-yl]benzenesulfonamide;

4-[5-(4-methylphenyl)-3-(difluoromethyl)-1H-pyrazol-1-yl]
benzenesulfonamide;
4-[5-phenyl-3-(difluoromethyl)-1H-pyrazol-1-yl]
benzenesulfonamide;
4-[5-(4-methoxyphenyl)-3-(difluoromethyl)-1H-pyrazol-1-yl]benzenesulfonamide;
4-[5-(3,4-dimethylphenyl)-3-(difluoromethyl)-1H-pyrazol-1-yl]benzenesulfonamide;
4-[5-(3-fluoro-4-methoxyphenyl)-3-(difluoromethyl)-1H-pyrazol-1-yl]benzenesulfonamide;
4-[1-[4-(aminosulfonyl)phenyl]-3-(difluoromethyl)-1H-pyrazol-5-yl]benzoic acid;
methyl 4-[1-[4-(aminosulfonyl)phenyl]-3-(difluoromethyl)-1H-pyrazol-5-yl]benzoate;
4-[1-(4-aminosulfonylphenyl)-3-(difluoromethyl)-1H-pyrazol-5-yl]benzamide;
4-[5-(2-fluoro-4-methoxyphenyl)-3-(difluoromethyl)-1H-pyrazol-1-yl]benzenesulfonamide;
4-[5-(4-cyanophenyl)-3-(difluoromethyl)-1H-pyrazol-1-yl]
benzenesulfonamide;
4-[5-(3-chloro-4-methylphenyl)-3-(difluoromethyl)-1H-pyrazol-1-yl]benzenesulfonamide;
4-[5-(3-chloro-4-methoxyphenyl)-3-(difluoromethyl)-1H-pyrazol-1-yl]benzenesulfonamide;
4-[5-(4-chloro-3-methylphenyl)-3-(difluoromethyl)-1H-pyrazol-1-yl]benzenesulfonamide;
4-[5-(3,4-dimethoxyphenyl)-3-(difluoromethyl)-1H-pyrazol-1-yl]benzenesulfonamide;
4-[5-(3,5-dichloro-4-methoxyphenyl)-3-(difluoromethyl)-1H-pyrazol-1-yl]benzenesulfonamide;
4-[5-(3,5-difluoro-4-methoxyphenyl)-3-(difluoromethyl)-1H-pyrazol-1-yl]benzenesulfonamide;
4-[5-(2-methoxyphenyl)-3-(difluoromethyl)-1H-pyrazol-1-yl]benzenesulfonamide;
4-[5-(3-bromo-4-methoxyphenyl)-3-(difluoromethyl)-1H-pyrazol-1-yl]benzenesulfonamide;
4-[5-(4-methylsulfonylphenyl)-3-(difluoromethyl)-1H-pyrazol-1-yl]benzenesulfonamide;
4-[5-(5-bromo-2-thienyl)-3-(difluoromethyl)-1H-pyrazol-1-yl]benzenesulfonamide;
4-[5-(5-chloro-2-thienyl)-3-(difluoromethyl)-1H-pyrazol-1-yl]benzenesulfonamide;
4-[5-(1-cyclohexenyl)-3-(difluoromethyl)-1H-pyrazol-1-yl]
benzenesulfonamide;
4-[5-(cyclohexyl)-3-(difluoromethyl)-1H-pyrazol-1-yl]
benzenesulfonamide;
4-[5-(biphenyl)-3-(difluoromethyl)-1H-pyrazol-1-yl]
benzenesulfonamide;
4-[5-(1,4-benzodioxan-6-yl)-3-(difluoromethyl)-1H-pyrazol-1-yl]benzenesulfonamide;
4-[3-(difluoromethyl)-5-(4-methylcyclohexyl)-1H-pyrazol-1-yl]benzenesulfonamide;
4-[5-(methyl-1-cyclohexenyl)-3-(difluoromethyl)-1H-pyrazol-1-yl]benzenesulfonamide;
4-[5-(2-methyl-1-cyclopentenyl)-3-(difluoromethyl)-1H-pyrazol-1-yl]benzenesulfonamide;
4-[5-(benzofuran-2-yl)-3-(difluoromethyl)-1H-pyrazol-1-yl]benzenesulfonamide;
4-[5-(1,3-benzodioxol-5-yl)-3-(difluoromethyl)-1H-pyrazol-1-yl]benzenesulfonamide;
4-[5-(2-pyrazinyl)-3-(difluoromethyl)-1H-pyrazol-1-yl]
benzenesulfonamide;
4-[5-(4-(morpholino)phenyl)-3-(difluoromethyl)-1H-pyrazol-1-yl]benzenesulfonamide;
4-[5-(2,5-dimethyl-3-furyl)-3-(difluoromethyl)-1H-pyrazol-1-yl]benzenesulfonamide;
4-[5-(5-methyl-2-furyl)-3-(difluoromethyl)-1H-pyrazol-1-yl]benzenesulfonamide;

4-[5-(1-chloro-1-methyl-4-cyclohexyl)-3-(difluoromethyl)-1H-pyrazol-1-yl]benzenesulfonamide;
4-[5-(3,4-dibromo-4-methylcyclohexyl)-3-(difluoromethyl)-1H-pyrazol-1-yl]benzenesulfonamide;
4-[5-(2-methoxycyclohexyl)-3-(difluoromethyl)-1H-pyrazol-1-yl]benzenesulfonamide;
4-[5-(2-thienyl)-3-(difluoromethyl)-1H-pyrazol-1-yl]
benzenesulfonamide;
4-[5-(2,4-dimethyl-3-thienyl)-3-(difluoromethyl)-1H-pyrazol-1-yl]benzenesulfonamide;
4-[5-(2,5-dichloro-3-thienyl)-3-(difluoromethyl)-1H-pyrazol-1-yl]benzenesulfonamide;
4-[5-(benzofuran-5-yl)-3-(trifluoromethyl)-1H-pyrazol-1-yl]benzenesulfonamide;
4-[5-(5-bromo-2-thienyl)-3-(trifluoromethyl)-1H-pyrazol-1-yl]benzenesulfonamide;
4-[5-(5-chloro-2-thienyl)-3-(trifluoromethyl)-1H-pyrazol-1-yl]benzenesulfonamide;
4-[5-(5-indanyl)-3-(trifluoromethyl)-1H-pyrazol-1-yl]
benzenesulfonamide;
4-[5-(5-methyl-2-thienyl)-3-(trifluoromethyl)-1H-pyrazol-1-yl]benzenesulfonamide;
4-[5-(2,3-dihydrobenzofuran-5-yl)-3-(trifluoromethyl)-1H-pyrazol-1-yl]benzenesulfonamide;
4-[5-(1-cyclohexenyl)-3-(trifluoromethyl)-1H-pyrazol-1-yl]
benzenesulfonamide;
4-[5-(5-benzothienyl)-3-(trifluoromethyl)-1H-pyrazol-1-yl]
benzenesulfonamide;
4-[5-(3,4-dihydro-2H-1-benzopyran-6-yl)-3-(trifluoromethyl)-1H-pyrazol-1-yl]benzenesulfonamide;
4-[5-(3,4-dihydro-2H-1-benzothiopyran-6-yl)-3-(trifluoromethyl)-1H-pyrazol-1-yl]benzenesulfonamide;
4-[5-(2-phenylethenyl)-3-(trifluoromethyl)-1H-pyrazol-1-yl]benzenesulfonamide;
4-[5-(4-methyl-1,3-benzodioxol-6-yl)-3-(trifluoromethyl)-1H-pyrazol-1-yl]benzenesulfonamide;
4-[5-(4-methyl-1,3-benzodioxol-5-yl)-3-(trifluoromethyl)-1H-pyrazol-1-yl]benzenesulfonamide;
4-[5-(2-pyrazinyl)-3-(trifluoromethyl)-1H-pyrazol-1-yl]
benzenesulfonamide;
4-[5-(biphenyl)-3-(trifluoromethyl)-1H-pyrazol-1-yl]
benzenesulfonamide;
4-[5-(1,2,3,4-tetrahydronaphth-6-yl])-3-(trifluoromethyl)-1H-pyrazol-1-yl]benzenesulfonamide;
4-[5-(2-naphthyl)-3-(trifluoromethyl)-1H-pyrazol-1-yl]
benzenesulfonamide;
4-[5-(2-thiazolyl)-3-(trifluoromethyl)-1H-pyrazol-1-yl]
benzenesulfonamide;
4-[5-(2-oxazolyl)-3-(trifluoromethyl)-1H-pyrazol-1-yl]
benzenesulfonamide;
4-[5-(cyclohexyl)-3-(trifluoromethyl)-1H-pyrazol-1-yl]
benzenesulfonamide;
4-[5-(cyclopentyl)-3-(trifluoromethyl)-1H-pyrazol-1-yl]
benzenesulfonamide;
4-[5-(cycloheptyl)-3-(trifluoromethyl)-1H-pyrazol-1-yl]
benzenesulfonamide;
4-[5-(1-cyclopentenyl)-3-(trifluoromethyl)-1H-pyrazol-1-yl]benzenesulfonamide;
4-[5-(2-furyl)-3-(trifluoromethyl)-1H-pyrazol-1-yl]
benzenesulfonamide;
4-[5-(2-pyridyl)-3-(trifluoromethyl)-1H-pyrazol-1-yl]
benzenesulfonamide;
4-[5-(3-pyridyl)-3-(trifluoromethyl)-1H-pyrazol-1-yl]
benzenesulfonamide;
4-[5-(6-methyl-3-pyridyl)-3-(trifluoromethyl)-1H-pyrazol-1-yl]benzenesulfonamide;
4-[5-(4-pyridyl)-3-(trifluoromethyl)-1H-pyrazol-1-yl]
benzenesulfonamide;

4-[5-(3-cyclohexenyl)-3-(trifluoromethyl)-1H-pyrazol-1-yl]
benzenesulfonamide;

4-[5-(4-cyclohexenyl)-3-(trifluoromethyl)-1H-pyrazol-1-yl]
benzenesulfonamide;

4-[5-(4-methylcyclohex-4-ene-1-yl)-3-(trifluoromethyl)-
1H-pyrazol-1-yl]benzenesulfonamide;

4-[5-(5-chloro-2-furyl)-3-(trifluoromethyl)-1H-pyrazol-1-
yl]benzenesulfonamide;

4-[5-(5-bromo-2-furyl)-3-(trifluoromethyl)-1H-pyrazol-1-
yl]benzenesulfonamide;

4-[5-(6-methoxy-2-naphthyl)-3-(trifluoromethyl)-1H-
pyrazol-1-yl]benzenesulfonamide;

4-[5-(4-chlorophenyl)-3-(heptafluoropropyl)-1H-pyrazol-1-
yl]benzenesulfonamide;

4-[5-(4-chlorophenyl)-3-(chlorodifluoromethyl)-1H-
pyrazol-1-yl]benzenesulfonamide;

4-[5-(4-chlorophenyl)-3-(pentafluoroethyl)-1H-pyrazol-1-
yl]benzenesulfonamide;

4-[5-(3-chloro-4-methoxyphenyl)-3-(chloromethyl)-1H-
pyrazol-1-yl]benzenesulfonamide;

4-[3-(chlorodifluoromethyl)-5-(3-fluoro-4-
methoxyphenyl)-1H-pyrazol-1-yl]benzenesulfonamide;

4-[5-(phenyl)-3-(fluoromethyl)-1H-pyrazol-1-yl]
benzenesulfonamide;

4-[3-(dichloromethyl)-5-(3-fluoro-4-methoxyphenyl)-1H-
pyrazol-1-yl]benzenesulfonamide;

4-[3-(bromodifluoromethyl)-5-(3-fluoro-4-
methoxyphenyl)-1H-pyrazol-1-yl]benzenesulfonamide;

4-[5-(4-chlorophenyl)-3-(fluoromethyl)-1H-pyrazol-1-yl]
benzenesulfonamide;

4-[5-(4-chlorophenyl)-3-(chloromethyl)-1H-pyrazol-1-yl]
benzenesulfonamide;

4-[5-(4-chlorophenyl)-3-(dichloromethyl)-1H-pyrazol-1-yl]
benzenesulfonamide;

4-[5-(4-chlorophenyl)-3-(dichlorofluoromethyl)-1H-
pyrazol-1-yl]benzene sulfonamide;

4-[5-(4-fluorophenyl)-3-(trichloromethyl)-1H-pyrazol-1-yl]
benzenesulfonamide;

4-[5-(4-chlorophenyl)-3-(1,1-difluoroethyl)-1H-pyrazol-1-
yl]benzenesulfonamide;

4-[5-(4-chlorophenyl)-3-(1,1-difluoropropyl)-1H-pyrazol-
1-yl]benzenesulfonamide;

4-[5-(4-chlorophenyl)-3-(1,1-dichloroethyl)-1H-pyrazol-1-
yl]benzenesulfonamide;

4-[5-(4-chlorophenyl)-3-(1,1-dichloropropyl)-1H-pyrazol-
1-yl]benzenesulfonamide;

4-[5-(4-chlorophenyl)-3-nitro-1H-pyrazol-1-yl]
benzenesulfonamide;

4-[5-(4-chlorophenyl)-3-(amidino)-1H-pyrazol-1-yl]
benzenesulfonamide;

4-[5-(4-chlorophenyl)-3-(methylsulfonyl)-1H-pyrazol-1-yl]
benzenesulfonamide;

4-[5-(4-chlorophenyl)-3-(N-methyl-aminosulfonyl)-1H-
pyrazol-1-yl]benzenesulfonamide;

4-[5-(4-fluorophenyl)-3-(imidazolyl)-1H-pyrazol-1-yl]
benzenesulfonamide;

4-[5-(4-fluorophenyl)-3-(2-pyridyl)-1H-pyrazol-1-yl]
benzenesulfonamide;

4-[5-(4-chlorophenyl)-3-(N-cyanoamidino)-1H-pyrazol-1-
yl]benzenesulfonamide;

4-[5-(4-chlorophenyl)-3-(tetrazolyl)-1H-pyrazol-1-yl]
benzenesulfonamide;

4-[5-(4-chlorophenyl)-3-(phenylsulfonyl)-1H-pyrazol-1-yl]
benzenesulfonamide;

4-[5-(4-chlorophenyl)-3-(N-phenylaminosulfonyl)-1H-
pyrazol-1-yl]benzenesulfonamide;

4-[5-(4-chlorophenyl)-3-(N,N-dimethylaminosulfonyl)-1H-
pyrazol-1-yl]benzenesulfonamide;

4-[5-(4-chlorophenyl)-3-(N-methyl-N-
phenylaminosulfonyl)-1H-pyrazol-1-yl]
benzenesulfonamide;

4-[5-(4-chlorophenyl)-3-(N-ethylaminosulfonyl)-1H-
pyrazol-1-yl]benzenesulfonamide;

4-[5-(4-chlorophenyl)-3-(N-isopropylaminosulfonyl)-1H-
pyrazol-1-yl]benzenesulfonamide;

4-[5-(4-chlorophenyl)-3-(N-methyl-N-ethylaminosulfonyl)-
1H-pyrazol-1-yl]benzenesulfonamide;

4-[5-(4-chlorophenyl)-3-(N-methyl-N-(3-chlorophenyl)
aminosulfonyl)-1H-pyrazol-1-yl]benzenesulfonamide;

4-[5-(4-chlorophenyl)-3-(N-methyl-N-(2-pyridyl)
aminosulfonyl)-1H-pyrazol-1-yl]benzenesulfonamide;

4-[3-methyl-5-phenyl-1H-pyrazol-1-yl]
benzenesulfonamide;

4-[3-isobutyl-5-phenyl-1H-pyrazol-1-yl]
benzenesulfonamide;

4-[3-(3-hydroxypropyl)-5-phenyl-1H-pyrazol-1-yl]
benzenesulfonamide;

4-[5-(4-fluorophenyl)-3-(3-hydroxypropyl)-1H-pyrazol-1-
yl]benzenesulfonamide;

4-[5-(3,5-dichloro-4-methoxyphenyl)-3-(3-hydroxypropyl)-
1H-pyrazol-1-yl]benzenesulfonamide;

4-[5-(4-methylphenyl)-3-(2-hydroxyisopropyl)-1H-pyrazol-
1-yl]benzenesulfonamide;

1-[4-(aminosulfonyl)phenyl]-5-(4-fluorophenyl)-1H-
pyrazole-3-propanoic acid;

1-[4-(aminosulfonyl)phenyl]-5-(4-chlorophenyl)-1H-
pyrazole-3-propanoic acid;

1-[4-(aminosulfonyl)phenyl]-5-(4-chlorophenyl)-1H-
pyrazole-3-propanamide;

methyl 1-[4-(aminosulfonyl)phenyl]-5-(4-fluorophenyl)-
1H-pyrazole-3-propanoate;

4-[3-(3-hydroxymethyl)-5-phenyl-1H-pyrazol-1-yl]
benzenesulfonamide;

4-[5-(4-chlorophenyl)-3-(3-hydroxymethyl)-1H-pyrazol-1-
yl]benzenesulfonamide;

4-[3-(3-hydroxymethyl)-5-(4-methoxyphenyl)-1H-pyrazol-
1-yl]benzenesulfonamide;

4-[5-(3,5-dichloro-4-methoxyphenyl)-3-(3-
hydroxymethyl)-1H-pyrazol-1-yl]benzenesulfonamide;

4-[5-(3-chloro-4-methoxyphenyl)-3-(3-hydroxymethyl)-
1H-pyrazol-1-yl]benzenesulfonamide;

ethyl 3-[1-(4-aminosulfonylphenyl)-5-(phenyl)-1H-pyrazol-
3-yl]-2-cyano-2-propenoate;

4-[5-(4-chlorophenyl)-3-(chloro)-1H-pyrazol-1-yl]
benzenesulfonamide;

4-[5-(4-chlorophenyl)-3-(bromo)-1H-pyrazol-1-yl]
benzenesulfonamide;

4-[5-(4-chlorophenyl)-3-(fluoro)-1H-pyrazol-1-yl]
benzenesulfonamide;

4-[3-(difluoromethyl)-4,5-dihydro-7-methoxy-1H-benz[g]
indazol-1-yl]benzenesulfonamide;

4-[3-(difluoromethyl)-4,5-dihydro-7-methyl-1H-benz[g]
indazol-1-yl]benzenesulfonamide;

4-[4,5-dihydro-7-methoxy-3-(trifluoromethyl)-1H-benz[g]
indazol-1-yl]benzenesulfonamide;

4-[4,5-dihydro-3-(trifluoromethyl)-1H-benz[g]indazol-1-yl]
benzenesulfonamide;

4-[4,5-dihydro-7-methyl-3-(trifluoromethyl)-1H-benz[g]
indazol-1-yl]benzenesulfonamide;

4-[4,5-dihydro-6,8-dimethyl-3-(trifluoromethyl)-1H-benz
[g]indazol-1-yl]benzenesulfonamide;

4-[4,5-dihydro-6,8-dimethoxy-3-(trifluoromethyl-1H-benz
[g]indazol-1-yl]benzenesulfonamide;

methyl[1-(4-aminosulfonylphenyl)-4,5-dihydro-7-methoxy-
1H-benz[g]indazol-3-yl]carboxylate;

4-[4,5-dihydro-3-trifluoromethyl-1H-thieno[3,2,g]indazol-1-yl]benzenesulfonamide;
4-[1-phenyl-3-(difluoromethyl)-1H-pyrazol-5-yl]benzenesulfonamide;
4-[1-(4-chlorophenyl)-3-(difluoromethyl)-1H-pyrazol-5-yl]benzenesulfonamide;
4-[1-(4-fluorophenyl)-3-(difluoromethyl)-1H-pyrazol-5-yl]benzenesulfonamide;
4-[1-(4-methoxyphenyl)-3-(difluoromethyl)-1H-pyrazol-5-yl]benzenesulfonamide;
4-[1-phenyl-3-(trifluoromethyl)-1H-pyrazol-5-yl]benzenesulfonamide;
4-[1-(4-chlorophenyl)-3-(trifluoromethyl)-1H-pyrazol-5-yl]benzenesulfonamide;
4-[1-(4-fluorophenyl)-3-(trifluoromethyl)-1H-pyrazol-5-yl]benzenesulfonamide; and
4-[1-(4-methoxyphenyl)-3-(trifluoromethyl)-1H-pyrazol-5-yl]benzenesulfonamide.

A family of specific compounds of particular interest within Formula II consists of compounds and pharmaceutically-acceptable salts thereof as follows:
4-[5-(4-chlorophenyl)-3-(trifluoromethyl)-1H-pyrazol-1-yl]benzenesulfonamide;
4-[5-phenyl-3-(trifluoromethyl)-1H-pyrazol-1-yl]benzenesulfonamide;
4-[5-(4-fluorophenyl)-3-(trifluoromethyl)-1H-pyrazol-1-yl]benzenesulfonamide;
4-[5-(4-methoxyphenyl)-3-(trifluoromethyl)-1H-pyrazol-1-yl]benzenesulfonamide;
4-[5-(4-chlorophenyl)-3-(difluoromethyl)-1H-pyrazol-1-yl]benzenesulfonamide;
4-[5-(4-methylphenyl)-3-(trifluoromethyl)-1H-pyrazol-1-yl]benzenesulfonamide;
4-[4-chloro-5-(4-chlorophenyl)-3-(trifluoromethyl)-1H-pyrazol-1-yl]benzenesulfonamide;
4-[3-(difluoromethyl)-5-(4-methylphenyl)-1H-pyrazol-1-yl]benzenesulfonamide;
4-[3-(difluoromethyl)-5-phenyl-1H-pyrazol-1-yl]benzenesulfonamide;
4-[3-(difluoromethyl)-5-(4-methoxyphenyl)-1H-pyrazol-1-yl]benzenesulfonamide;
4-[3-cyano-5-(4-fluorophenyl)-1H-pyrazol-1-yl]benzenesulfonamide;
4-[3-(difluoromethyl)-5-(3-fluoro-4-methoxyphenyl)-1H-pyrazol-1-yl]benzenesulfonamide;
4-[5-(3-fluoro-4-methoxyphenyl)-3-(trifluoromethyl)-1H-pyrazol-1-yl]benzenesulfonamide;
4-[4-chloro-5-phenyl-1H-pyrazol-1-yl]benzenesulfonamide;
4-[5-(4-chlorophenyl)-3-(hydroxymethyl)-1H-pyrazol-1-yl]benzenesulfonamide; and
4-[5-(4-N,N-dimethylamino)phenyl)-3-(trifluoromethyl)-1H-pyrazol-1-yl]benzenesulfonamide.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where the term "alkyl" is used, either alone or within other terms such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of tow to about twenty carbon atoms or, preferably, two to about twelve carbon atoms. More preferred alkyl radicals are "lower alkenyl" radicals having two to about six carbon atoms. Examples of such radicals include ethenyl, n-propenyl, butenyl, and the like. The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radical shaving one to about ten carbon atoms any one of which may be substituted with one or more hydroxyl radicals. More preferred hydroxyalkyl radicals are "lower hydroxyalkyl" radicals having one to sic carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms, such as methoxy radical. More preferred alkoxy radicals are "lower alkoxy" radicals having one to sic carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" or "alkoxyalkyl" radicals maybe further substituted with one or more halo atoms, such as fluoro, chloro or bromo, to provide "haloalkoxy" or "haloalkoxyalkyl" radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocyclic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 5 to 6 membered heteromonocyclic group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. Preferred heterocyclic radicals include five to ten membered fused or unfused radicals. More preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The term "arylsulfonyl" embraces aryl radicals as defined above, attached to a sulfonyl radical. Examples of such radicals include phenylsulfonyl. The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—SO$_2$NH$_2$). The terms "N-alkylaminosulfonyl" and "N,N-dialkylaminosulfonyl" denote sulfamyl radicals substituted, respectively, with one alkyl radical, or two alkyl radicals. More preferred alkylaminosulfonyl radicals are "lower alkylaminosulfonyl" radicals having one to six carbon atoms. Examples of such lower alkylaminosulfonyl radicals include N-methylaminosulfonyl, N-ethylaminosulfonyl and N-methyl-N-ethylaminosulfonyl. The terms "N-arylaminosulfonyl" and "N-alkyl-N-arylaminosulfonyl" denote sulfamyl radicals substituted, respectively, with one aryl radical, or one alkyl and one aryl radical. More preferred N-alkyl-N-arylaminosulfonyl radicals are "lower N-alkyl-N-arylsulfonyl" radicals having alkyl radicals of one to six carbon atoms. Examples of such lower N-alkyl-N-aryl aminosulfonyl radicals include N-methyl-phenylaminosulfonyl and N-ethyl-phenylaminosulfonyl The terms "carboxy" or "carboxyl", whether used alone or with other terms, such as "carboxyalkyl", denotes —CO$_2$H. The terms "alkanoyl" or "carboxyalkyl" embrace radicals having a carboxy radical as defined above, attached to an alkyl radical. The alkanoyl radicals may be substituted or unsubstituted, such as formyl, acetyl, propionyl (propanoyl), butanoyl (butyryl), isobutanoyl (isobutyryl), valeryl (pentanoyl), isovaleryl, pivaloyl, hexanoyl or the like. The term "carbonyl", whether used alone or with other terms, such as "alkylcarbonyl", denotes —(C=O)—. The term "alkylcarbonyl" embraces radicals having a carbonyl radical substituted with an alkyl radical. More preferred alkylcarbonyl radicals are "lower alkylcarbonyl" radicals having one to six carbon atoms. Examples of such radicals include methylcarbonyl and ethylcarbonyl. The term "alkylcarbonylalkyl", denotes an alkyl radical substituted with an "alkylcarbonyl" radical. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl,, ethoxycarbonyl, propoxycarbonyl, butoxycarbonyl and hexyloxycarbonyl. The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl, tert-butoxycarbonylethyl, and methoxycarbonylethyl. The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)NH$_2$. The terms "N-alkylaminocarbonyl" and "N,N-dialkylaminocarbonyl" denote aminocarbonyl radicals which have been substituted with one alkyl radical and with two alkyl radicals, respectively. More preferred are "lower alkylaminocarbonyl" having lower alkyl radicals as described above attached to an aminocarbonyl radical. The terms "N-arylaminocarbonyl" and "N-alkyl-N-arylaminocarbonyl" denote aminocarbonyl radicals substituted, respectively, with one aryl radical, or one alkyl and one aryl radical. The term "aminocarbonylalkyl" embraces alkyl radicals substituted with aminocarbonyl radicals. The term "N-cycloalkylaminocarbonyl" denoted aminocarbonyl radicals which have been substituted with at least one cycloalkyl radical. More preferred are "lower cycloalkylaminocarbonyl" having lower cycloalkyl radicals of three to seven carbon atoms, attached to an aminocarbonyl radical. The term "aminoalkyl" embraces alkyl radicals substituted with amino radicals. The term "alkylaminoalkyl" embraces aminoalkyl radicals having the nitrogen atom substituted with an alkyl radical. The term "amidino" denotes an —C(=NH)—NH$_2$ radical. The term "cyanoamidino" denotes an —C(=N—CN)—NH$_2$ radical. The term "heterocyclicalkyl" embraces heterocyclic-substituted alkyl radicals. More preferred heterocyclicalkyl radicals are "lower heterocyclicalkyl" radicals having one to six carbon atoms and a heterocyclic radical. Examples include such radicals as pyrrolidinylmethyl, pyridylmethyl and thienylmethyl. The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The aryl in said aralkyl may be additionally substituted with halo, alkyl, alkoxy, halkoalkyl and haloalkoxy. The terms benzyl and phenylmethyl are interchangeable. The term "cycloalkyl" embraces radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term "cycloalkenyl" embraces unsaturated cyclic radicals having three to ten carbon atoms, such as cyclobutenyl, cyclopentenyl, cyclohexenyl and cycloheptenyl. The term "alkylthio" embraces radicals containing a linear or branched alkyl radical, of one to ten carbon atoms, attached to a divalent sulfur atom. An example of "alkylthio" is methylthio, (CH$_3$—S—). The term "alkylsulfinyl" embraces radicals containing a linear or branched alkyl radical, of one to ten carbon atoms, attached to a divalent —S(=O)— atom. The term "aminoalkyl" embraces alkyl radicals substituted with amino radicals. More preferred aminoalkyl radicals are "lower aminoalkyl" having one to six carbon atoms. Examples include aminomethyl, aminoethyl and aminobutyl. The term "alkylaminoalkyl" embraces aminoalkyl radicals having the nitrogen atom substituted with at least one alkyl radical. More preferred alkylaminoalkyl radicals are "lower alkylaminoalkyl" having one to six carbon atoms attached to a lower aminoalkyl radical as described above. The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to a nitrogen atom. Suitable "alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aralkylamino" denotes amino groups which have been substituted with one or two aralkyl radicals, such as N-benzylamino. The "aralkylamino" radicals may be further substituted on the aryl ring portion of the radical. The terms "N-alkyl-N-arylamino" and "N-aralkyl-N-alkylamino" denote amino groups which have been substituted with one aralkyl and one alkyl radical, or one aryl and one alkyl radical, respectively, to an amino group. The terms "N-arylaminoalkyl" and "N-aralkylaminoalkyl" denote amino groups which have been substituted with one aryl radical or one aralkyl radical, respectively, and having the amino group attached to an alkyl radical. More preferred arylaminoalkyl radicals are "lower arylaminoalkyl" having the arylamino radical attached to one to six carbon atoms. Examples of such radicals include N-phenylaminomethyl and N-phenyl-N-methylaminomethyl. The terms "N-alkyl-N-arylaminoalkyl" and "N-aralkyl-N-alkylaminoalkyl" denote N-alkyl-N-arylamino and N-alkyl-N-aralkylamino groups, respectively, and having the amino group attached to alkyl radicals. The term "acyl", whether used alone, or within a term such as "acylamino", denotes a radical provided by the residue after removal of hydroxyl from an organic acid. The term "acylamino" embraces an amino radical substituted with an acyl group. An examples of an "acylamino" radical is acetylamino or acetamido (CH$_3$C(=O)—NH—) where the amine may be further substituted with alkyl, aryl or aralkyl. The term "arylthio" embraces aryl radicals of six to ten carbon atoms, attached to a divalent sulfur atom. An example of "arylthio" is phenylthio. The term "aralkylthio" embraces aralkyl radicals as described above, attached to a divalent sulfur atom. An example of "aralkylthio" is benzylthio. The term "aryloxy" embraces aryl radicals, as defined above, attached to an oxygen atom. Examples of such radicals include phenoxy. The term "aralkoxy" embraces oxy-containing aralkyl radicals attached through an oxygen atom to other radicals. More preferred aralkoxy radicals are "lower aralkoxy" radicals having phenyl radicals attached to lower alkoxy radical as described above. The term "haloaralkyl" embraces aryl radicals as defined above attached to haloalkyl radicals. The term "carboxyhaloalkyl" embraces carboxyalkyl radicals as defined above having halo radicals attached to the alkyl portion. The term "alkoxycarbonylhaloalkyl" embraces alkoxycarbonyl radicals as defined above substituted on a haloalkyl radical. The term "aminocarbonylhaloalkyl" embraces aminocarbonyl radicals as defined above substituted on a haloalkyl radical. The term "alkylaminocarbonylhaloalkyl" embraces alkylaminocarbonyl radicals as defined above substituted on a haloalkyl radical. The term "alkoxycarbonylcyanoalkenyl" embraces alkoxycarbonyl radicals as defined above, and a cyano radical, both substituted on an alkenyl radical. The term "carboxyalkylaminocarbonyl" embraces aminocarbonyl radicals substituted with carboxyalkyl radicals, as defined above. The term "aralkoxycarbonylalkylaminocarbonyl" embraces aminocarbonyl radicals substituted with aryl-substituted alkoxycarbonyl radicals, as defined above. The term "cycloalkylalkyl" embraces cycloalkyl radicals having three to ten carbon atoms attached to an alkyl radical, as defined above. More preferred cycloalkylalkyl radicals are "lower cycloalkylalkyl" radicals having cycloalkyl radicals attached to lower alkyl radicals as defined above. Examples include radicals such as cyclopropylmethyl, cyclobutylmethyl, and cyclohexylethyl. The term "aralkenyl" embraces aryl radicals attached to alkenyl radicals having two to ten carbon atoms, such as phenylbutenyl, and phenylethenyl or styryl.

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable.

Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartartic, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made form N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–VIII, wherein the $R^1$–$R^7$ substituents are as defined for Formula I, above, except where further noted.

SCHEME I

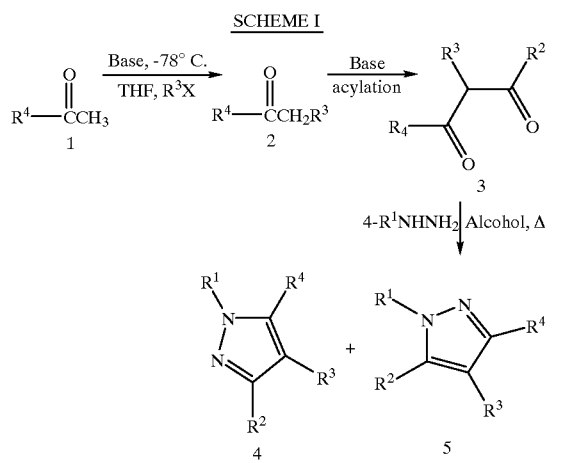

Synthetic Scheme I shows the preparation of tetrasubstituted pyrazoles from starting material 1. In step 1 of synthetic Scheme I, the phenyl-methyl ketone (1) is treated with a base and an alkylating reagent ($R^3X$, where X represents a leaving group such as tosyl) to give the substituted ketone (2). In step 2, the substituted ketone (2) is treated with base, such as sodium methoxide, and an acylating reagent such as an ester ($R^2CO_2CH_3$), or ester equivalent ($R^2CO$-imidazole, to give the intermediate diketone (3) in a procedure similar to that developed by Reid and Calvin, *J. Amer. Chem. Soc.*, 72, 2948–2952 (1950). In step 3, the diketone (3) is reacted with a substituted hydrazine in acetic acid or an alcoholic solvent to give a mixture of pyrazoles (4) and (5). Separation of the desired pyrazole (4) can be achieved by chromatography or recrystallization.

SCHEME II

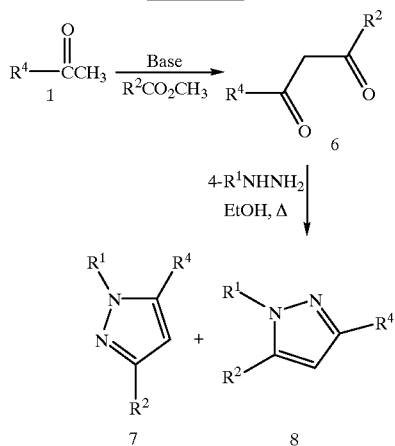

Synthetic Scheme II shows the preparation of compounds embraced by Formula I, where $R^3$ is a hydrogen atom. In step 1, ketone (1) is treated with a base, preferably NaOMe or NaH, and an ester, or ester equivalent, to form the intermediate diketone (6) which is used without further purification. In step 2, diketone (6) in an anhydrous protic solvent, such as absolute ethanol or acetic acid, is treated with the hydrochloride salt or the free base of a substituted hydrazine at reflux for 10 to 24 hours to afford a mixture of pyrazoles (7) and (8). Recrystallization from diethyl ether/hexane or chromatography affords (7), usually as a light yellow or tan solid.

Scheme III

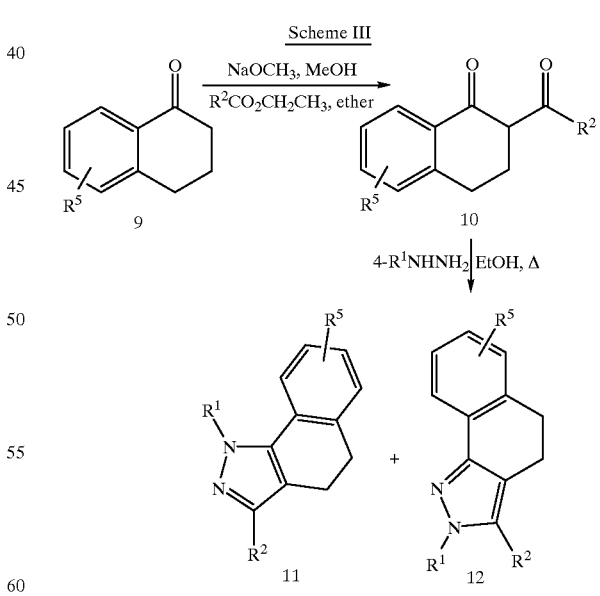

Synthetic Scheme III shows the procedure for preparation of 4,5-dihydrobenz[g]indazole compounds embraced by Formula I. In step 1, ethyl trifluoroacetate is reacted with base, such as 25% sodium methoxide in a protic solvent, such as methanol, and a 1-tetralone derivative (9) to give the intermediate diketone (10). In step 2, the diketone (10) in an anhydrous protic solvent, such as absolute ethanol or acetic acid, is treated with the free base or hydrochloride salt of a substituted hydrazine at reflux for 24 hours to afford a mixture of pyrazoles (11) and (12). Recrystallization gives the 4,5-dihydro benz[g]indazolyl-benzenesulfonamide (11).

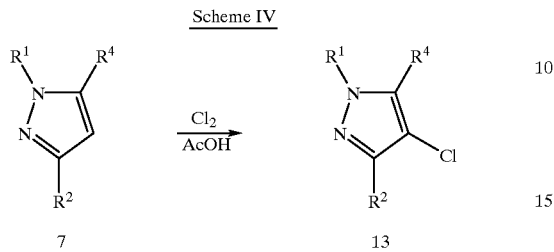

Scheme IV

Synthetic Scheme IV shows the preparation of pyrazole compounds (13), where $R^3$ is chlorine, from the available pyrazole compounds (7), where $R^3$ is hydrogen. Chlorination results from passing a stream of chlorine gas at room temperature through a solution containing (7).

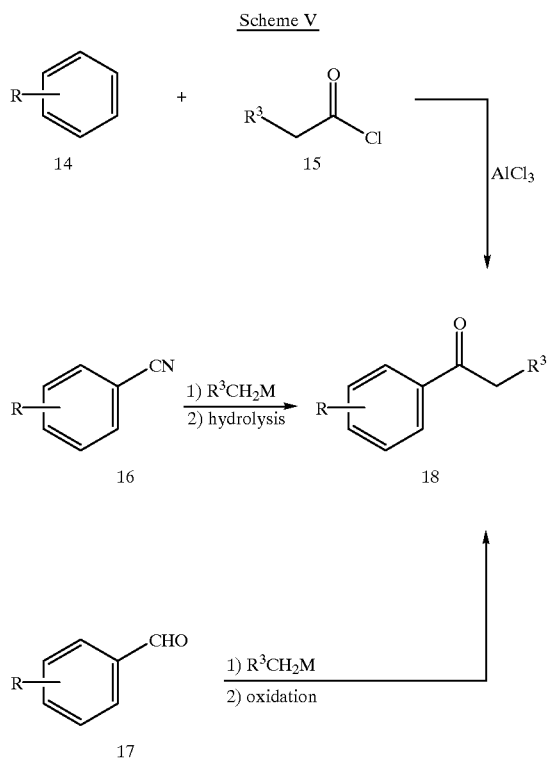

Scheme V

Synthetic Scheme V shows the preparation of substituted ketones 18 which are not commercially available as used in Scheme I. The ketones can be prepared by standard Friedel-Craft acylation of the starting substituted benzenes 14 with acid chlorides or anhydrides 15. Alternatively, the ketones can be prepared from phenylcarbonitriles 16 by standard organometallic techniques where M represents metals such as lithium, magnesium, and the like. An alternative organometallic route is shown from the aldehydes 17 where M represents metals such as lithium, magnesium, and the like. Oxidation with a suitable oxidizing agent, such as $CrO_3$, follows to produce the ketones.

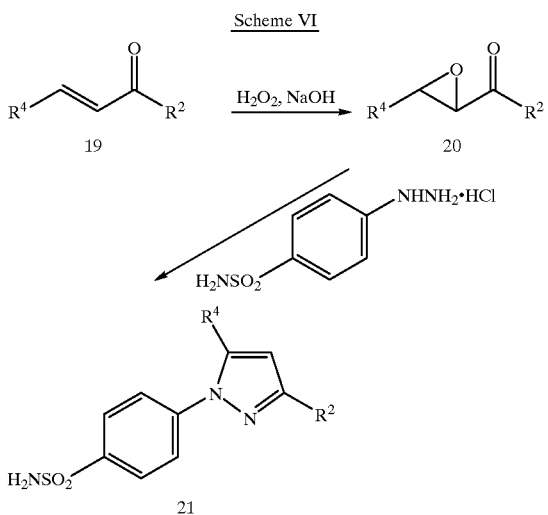

Scheme VI

Synthetic Scheme VI shows an alternative regioselective method of constructing the pyrazole 21. Commercially available enones 19 can be epoxidized to give epoxyketones 20, which are treated with 4-sulfonaminophenylhydrazine hydrochloride to provide the pyrazole 21.

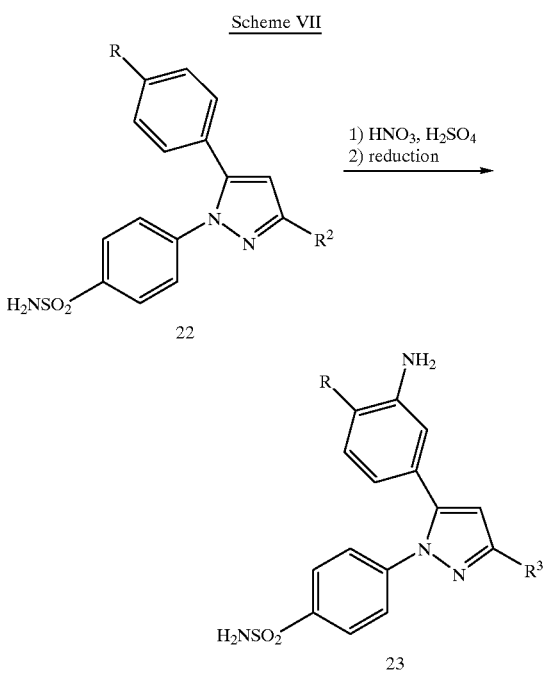

Scheme VII

Synthetic Scheme VII shows the preparation of pyrazoles 23 (where $R^4$ is 3-amino-4-substituted phenyl) from starting material 22. Appropriate 5-(4-substituted aryl)pyrazoles can be nitrated next to the R-group under standard nitration conditions and the nitro group reduced to the amino group, preferably with hydrazine and Pd/C. The amino compounds can be further manipulated by alkylation of the amino group.

Scheme VIII

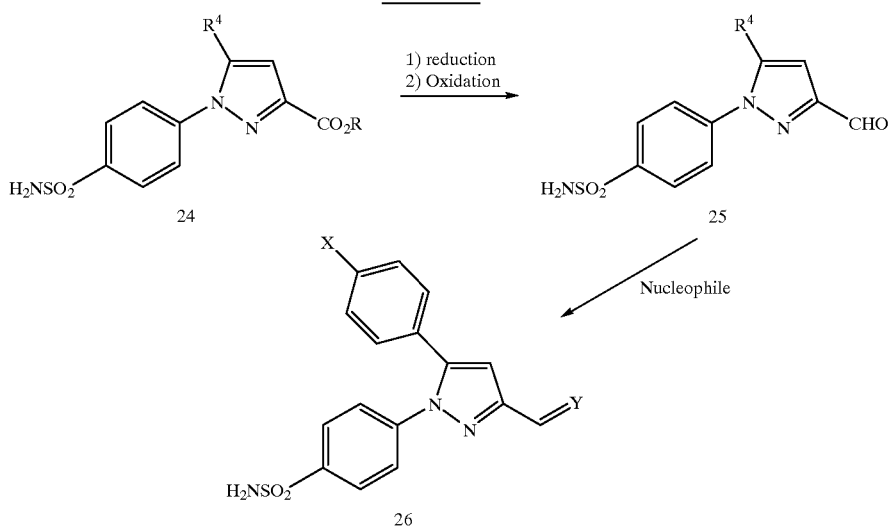

Synthetic Scheme VIII shows the preparation of pyrazoles 26 from esters 24. Reduction of the ester 24 to the alcohol, preferably with lithium aluminum hydride (LAH) followed by oxidation, preferably with $MnO_2$, gives the aldehyde 25. Various nucleophiles (such as hydroxamates and 1,3-dicarbonyl compounds) can be condensed with the aldehyde to give the desired oximes or olefins 26.

The following examples contain detailed descriptions of the methods of preparation of compounds of Formulas I—II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. HRMS is an abbreviation for High resolution mass spectrometry. In the following tables, "ND" represents "not determined".

EXAMPLE 1

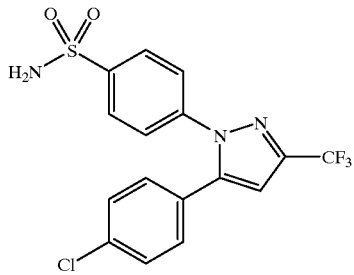

4-[5-(4-Chlorophenyl)-3-(trifluoromethyl)-1H-pyrazol-1-yl]benzenesulfonamide

Step 1: Preparation of 4,4,4-trifluoro-1-[4-(chloro)phenyl]-butane-1,3-dione.

Ethyl trifluoroacetate (23.52 g, 166 mmol) was placed in a 500 mL three-necked round bottom flask, and dissolved in methyl tert-butyl ether (75 mL). To the stirred solution was added 25% sodium methoxide (40 mL, 177 mmol) via an addition funnel over a 2 minute period. Next 4'-chloroacetophenone (23.21 g, 150 mmol) was dissolved in methyl tert-butyl ether (20 mL), and added to the reaction dropwise over 5 minutes. After stirring overnight (15.75 hours), 3N HCl (70 mL) was added. The organic layer was collected, washed with brine (75 mL), dried over $MgSO_4$, filtered, and concentrated in vacuo to give a 35.09 g of yellow-orange solid. The solid was recrystallized from iso-octane to give 31.96 g (85%) of the dione: mp 66–67° C.

Step 2: Preparation of 4-[5-(4-chlorophenyl)-3-(trifluoromethyl)-1H-pyrazol-1-yl]benzenesulfonamide.

4-Sulphonamidophenylhydrazine hydrochloride (982 mg, 4.4 mmol 1.1 equivalent) was added to a stirred solution of 4,4,4-trifluoro-1-[4-(chloro)phenyl]-butane- 1,3-dione from Step 1 (1.00 g, 4.0 mmol) in ethanol (50 mL). The reaction was heated to reflux and stirred for 20 hours. (HPLC area percent showed a 96:3 ratio of 4-[5-(4-chlorophenyl)-3-(trifluoromethyl)-1H-pyrazol-1-yl]benzenesulfonamide to its regioisomer (4-[3-(4-chlorophenyl)-5-(trifluoromethyl)-1H-pyrazol-1-yl]benzenesulfonamide). After cooling to room temperature, the reaction mixture was concentrated in vacuo. The residue was taken up in ethyl acetate, washed with water and with brine, dried over $MgSO_4$, filtered, and concentrated in vacuo to give a light brown solid which was recrystallized from ethyl acetate and iso-octane to give the pyrazole (1.28 g, 80%, mp 143–145° C.). HPLC showed that the purified material was a 99.5:0.5 mixture of 4-[5-(4-chlorophenyl)-3-(trifluoromethyl)-1H-pyrazol-1-yl]benzenesulfonamide to its regioisomer. $^1H$ NMR ($CDCl_3$/$CD_3OD$ 10/1) d 5.2 (s, 2H), 6.8 (s, 1H), 7.16 (d, j=8.5 Hz, 2H), 7.35 (d, j=8.5 Hz, 2H), 7.44 (d, j=8.66, 2H), 7.91 (d, j=8.66, 2H); $^{13}C$ NMR ($CDCl_3$/$CD_3OD$ 10/1) d 106.42 (d, j=0.03 Hz), 121.0 (q, j=276 Hz), 125.5, 126.9, 127.3, 129.2, 130.1, 135.7, 141.5, 143.0, 143.9 (q, j=37 Hz), 144.0; $^{19}F$ NMR ($CDCl_3$/$CD_3OD$ 10/1) d −62.9. EI GC-MS M+=401.

EXAMPLE 2

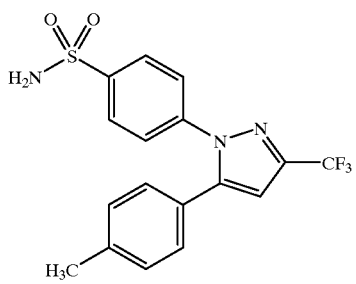

4-[5-(4-Methylphenyl)-3-(trifluoromethyl)-1H-pyrazol-1-yl]benzenesulfonamide

Step 1: Preparation of 1-(4-methylphenyl)-4,4,4-trifluorobutane-1,3-dione

4'-Methylacetophenone (5.26 g, 39.2 mmol) was dissolved in 25 mL of methanol under argon and 12 mL (52.5 mmol) sodium methoxide in methanol (25%) was added. The mixture was stirred for 5 minutes and 5.5 mL (46.2 mmol) ethyl trifluoroacetate was added. After refluxing for 24 hours, the mixture was cooled to room temperature and concentrated. 100 mL 10% HCl was added and the mixture extracted with 4×75 mL ethyl acetate. The extracts were dried over $MgSO_4$, filtered and concentrated to afford 8.47 g (94%) of a brown oil which was carried on without further purification.

Step 2: Preparation of 4-[5-(4-methylphenyl)-3-(trifluoromethyl)-1H-pyrazol-1-yl]benzenesulfonamide To the dione from Step 1 (4.14 g, 18.0 mmol) in 75 mL absolute ethanol was added 4.26 g (19.0 mmol) 4-sulphonamidophenylhydrazine hydrochloride. The reaction was refluxed under argon for 24 hours. After cooling to room temperature and filtering, the reaction mixture was concentrated to afford 6.13 g of an orange solid. The solid was recrystallized from methylene chloride/hexane to give 3.11 g (8.2 mmol, 46%) of the product as a pale yellow solid: mp 157–159° C.; Anal. calc'd for $C_{17}H_{14}N_3O_2SF_3$: C, 53.54; H; 3.70; N, 11.02. Found: C, 53.17; H, 3.81; N, 10.90.

EXAMPLE 3

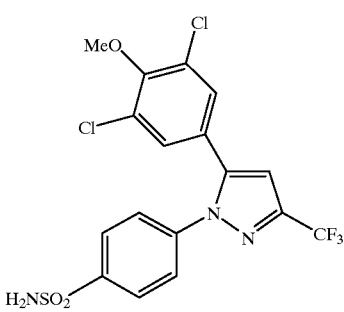

4-[5-(3,5-Dichloro-4-methoxyphenyl)-3-(trifluoromethyl)-1H-pyrazol-1-yl]benzenesulfonamide Step 1: Preparation of 3,5-dichloro-4-methoxyacetophenone To a cooled solution (0° C.) of 7.44 g (55.8 mmol) $AlCl_3$ in 25 mL of $CH_2Cl_2$ under argon was added 2.5 mL of acetic anhydride dropwise. After stirring for 0.5 hours, 4.18 g (23.6 mmol) of 2,6-dichloroanisole was added dropwise. The reaction was stirred at 0° C. for 1 hour, warmed to room temperature and stirred for 12 hours. The reaction was poured into 6 mL conc. hydrochloric acid/80 mL ice water. The aqueous phase was extracted with ethyl acetate (3×75 mL). The combined organic washes were dried over $MgSO_4$, filtered, and stripped to afford the crude product as a yellow oil. NMR analysis showed that acylation only occured para to the methoxy. The crude oil was used without any further purification.

Steps 2 and 3: Preparation of 4-[5-(3,5-dichloro-4-methoxyphenyl)-3-(trifluoromethyl)-1H-pyrazol-1-yl]benzenesulfonamide The title compound was prepared in the same manner as Example 2. Steps 1 and 2 and was purified on a prep plate eluting with 10:1 hexane/ethyl acetate to afford a yellow solid: Anal. calc'd for $C_{17}H_{12}N_3O_3SF_3Cl_2 \cdot H_2O$: C, 42.16; H, 2.91; N, 8.68. Found: C, 42.03; H, 2.54; N, 8.45.

EXAMPLE 4

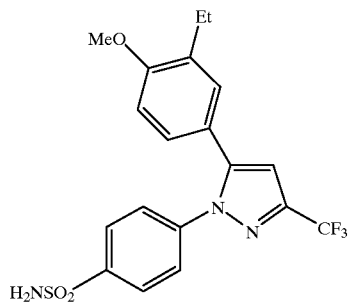

4-[5-(3-Ethyl-4-methoxyphenyl)-3-(trifluoromethyl)-1H-pyrazol-1-yl]benzenesulfonamide Step 1: Preparation of 3-ethyl-4-methoxyacetophenone $AlCl_3$ (4.9 g, 36.8 mmol) was added to a solution of 2-ethylanisole (2.5 g, 18.4 mmol) in methylene chloride (50 mL). Acetyl chloride (1.3 mL, 18.4 mmol) was added dropwise to the reaction mixture, which was then stirred at reflux for 0.5 hours. After cooling to room temperature, the reaction was poured over crushed ice and followed up with a methylene chloride/water extraction. The organic layer was dried over magnesium sulfate, filtered and concentrated. The crude product was chromatographed on a 4000 micron chromatotron plate with 10% ethyl acetate/90% hexane as eluant to afford 2.3 g of desired material.

Steps 2 and 3: Preparation of 4-[5-(3-ethyl-4-methoxyphenyl)-3-(trifluoromethyl)-1H-pyrazol-1-yl]benzenesulfonamide The title compound was prepared using the procedure described in Example 2. Steps 1 and 2: Anal. calcd for $C_{19}H_{18}N_3O_3SF_3$: C, 53.64; H, 4.26; N, 9.88. Found: C, 53.69; H, 4.36; N, 9.88.

EXAMPLE 5

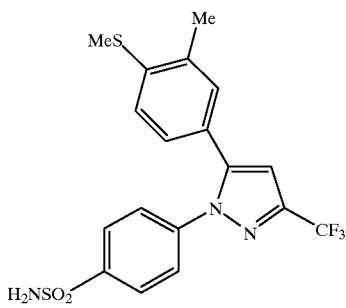

4-[5-(3-Methyl-4-methylthiophenyl)-3-(trifluoromethyl)-1H-pyrazol-1-yl]benzenesulfonamide Step 1: Preparation of 2-methylthioanisole Methyl iodide (0.5 mL, 8.1 mmol) and potassium carbonate (1.1 g, 8.1 mmol) were added to a solution of o-thiocresol (1.0 g, 8.1 mmol) in 10 mL of DMF. The reaction was stirred at 50° C. for 4 hours and poured into hexane and water. The organic layer was separated, dried over magnesium sulfate and concentrated to afford 1.1 g of desired material.

Steps 2, 3 and 4: Preparation of 4-[5-(3-methyl)-4-methylthiophenyl)-3-(trifluoromethyl)-1H-pyrazol-1-yl]benzenesulfonamide The title compound was prepared using the procedures found in Example 4. Steps 1, 2 and 3: Anal. calcd. for $C_{18}H_{16}N_3O_2S_2F_3$: C, 50.58; H, 3.77; N, 9.83. Found: C, 50.84; H, 3.62; N, 9.62.

EXAMPLE 6

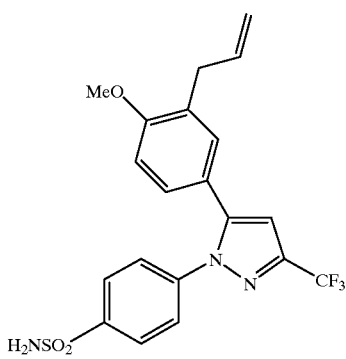

4-[5-(3-(3-Propenyl)-4-methoxyphenyl)-3-(trifluoromethyl)-1H-pyrazol-1-yl]benzenesulfonamide Step 1: Preparation of 3-allyl-4-methoxyacetophenone Potassium hydroxide (3.2 g, 56.8 mmol) was added to a solution of 3-allyl-4-hydroxyacetophenone (10 g, 56.8) in 125 mL THF. Dimethyl sulfate (excess) was added and the reaction was stirred at 50° C. for 16 hours. The reaction was cooled, concentrated and poured into EtOAc and water. The organic layer was separated and washed with dilute sodium hydroxide to get rid of unreacted starting material. The ethyl acetate layer was dried and concentrated to afford 9.2 g of 3-allyl-4-methoxy acetophenone.

Steps 2 and 3: Preparation of 4-[5-(3-(3-propenyl)-4-methoxyphenyl)-3-(trifluoromethyl)-1H-pyrazol-1-yl]benzenesulfonamide The title compound was prepared using the procedures described in Example 2, Steps 1 and 2: Anal. calc'd for $C_{20}H_{18}N_3F_3O_3S$: C, 54.92; H, 4.15; N, 9.61. Found: C, 54.70; H, 4.12; N, 9.43.

EXAMPLE 7

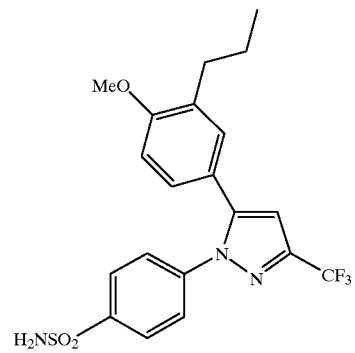

4-[5-(3-Propyl-4-methoxyphenyl)-3-(trifluoromethyl)-1H-pyrazol-1-yl]benzenesulfonamide Step 1: Preparation of 3-n-propyl-4-methoxyacetophenone To a solution of the product in Example 6, Step 1 (3 g, 17.0 mmol) in 50 mL of ethanol was added a catalytic amount of 4% Pd/C. The reaction mixture was stirred in a Parr shaker at room temperature at 5 psi hydrogen for 0.5 hours. The reaction was filtered and concentrated to afford 4 g of pure 3-propyl-4-methoxy acetophenone.

Steps 2 and 3: Preparation of 4-[5-(3-n-propyl-4-methoxyphenyl)-3-(trifluoromethyl)-1H-pyrazol-1-yl]benzenesulfonamide The title compound was prepared using the procedures described in Example 2. Steps 1 and 2: Anal. calcd. for $C_{20}H_{20}N_3F_3O_3S$: C, 54.66; H, 4.59; N, 9.56. Found: C, 54.84; H, 4.65; N, 9.52.

EXAMPLE 8

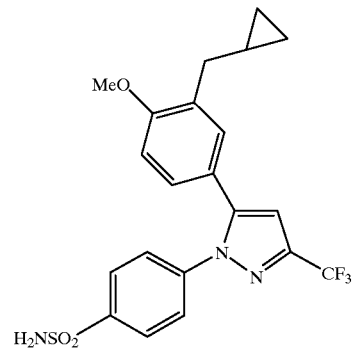

4-[5-(3-Cyclopropylmethyl-4-methoxyphenyl)-3-(trifluoromethyl)-1H-pyrazol-1-yl]benzenesulfonamide Step 1: Preparation of 3-cyclopropylmethyl-4-methoxyacetophenone To a solution of the product in Example 6, Step 1 (3 g, 17.0 mmol) and catalytic Pd(OAc)$_2$ in 20 mL Et$_2$O was added ethereal diazomethane until starting material was consumed. The reaction was filtered, concentrated and chromatographed on a 4000 micron chromatotron plate (20% EA/80% hexane as eluant) to afford 2.5 g of desired ketone.
Steps 2 and 3: Preparation of 4-[5-(3-cyclopropylmethyl-4-methoxyphenyl)-3-(trifluoromethyl)-1H-pyrazol-1-yl]benzenesulfonamide The title compound was prepared using the procedures described in Example 2. Steps 1 and 2: Anal. calc'd. for $C_{21}H_{20}N_3F_3SO_3$: C, 55.87; H, 4.47; N, 9.31. Found: C, 55.85; H, 4.27; N, 9.30.

EXAMPLE 9

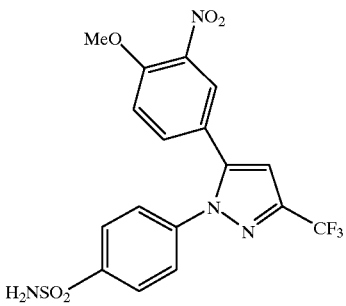

4-[4-Methyl-3-nitrophenyl)-3-(trifluoromethyl)-1H-pyrazol-1-yl]benzenesulfonamide To a solution of the product of Example 2 (500 mg, 1.31 mmol) and 5 mL of sulfuric acid was added nitric acid (0.6 mL, 1.31 mmol) and the reaction was stirred at room temperature for 0.5 hours. The mixture was poured over ice, the solid precipitate was filtered and chromatographed on a 4000 micron plate (20% EtOAc/80% hexane as eluant) to afford 410 mg of desired material: Anal. calc'd for $C_{17}H_{13}N_4O_4SF_3$: C, 47.89; H, 3.07; N, 13.14. Found: C, 47.86; H, 2.81; N, 13.15.

EXAMPLE 10

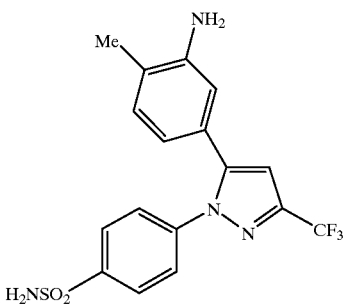

4-[5-(3-Amino-4-methylphenyl)-3-(trifluoromethyl)-1H-pyrazol-1-yl]benzenesulfonamide A catalytic amount of 10% Pd/C was added to a solution of hydrazine hydrate (0.022 mL, 0.7 mmol) in 10 mL of ethanol. The reaction mixture was refluxed for 15 minutes before the addition of the compound from Example 9 (100 mg, 0.23 mmol), and the resulting reaction mixture was refluxed for another 2 hours. The reaction was cooled, filtered through Celite and concentrated to afford 100 mg of title compound: Anal. calc'd for $C_{17}H_{15}N_4O_2SF_3.0.5\ CO_2$: C, 50.24; H, 3.61; N, 13.39. Found: C, 50.49; H, 3.44; N, 13.37.

EXAMPLE 11

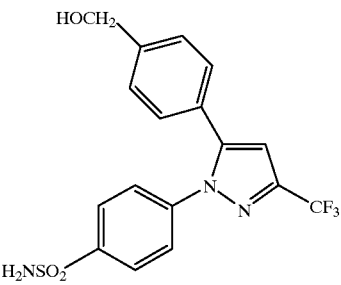

4-[5-(4-Hydroxymethylphenyl)-3-(trifluoromethyl)-1H-pyrazol-1-yl]benzenesulfonamide Step 1: Preparation of 4-[5-(4-bromomethylphenyl)-3-(trifluoromethyl)-1H-pyrazol-1-yl]benzenesulfonamide The product from Example 2 (1.13 g, 3.0 mmol) and N-bromosuccinimide (NBS, 0.64 g, 3.6 mmol) were dissolved in 40 mL of benzene and irradiated with a UV lamp for 3 hours. The reaction was cooled to room temperature and poured into 50 mL of $H_2O$. The organic phase was separated, washed with brine and dried over $MgSO_4$. The crude pyrazole was obtained as an amber oil. The oil was purified via radical band chromatography eluting with 30% ethyl acetate/70% hexane to afford the 4-bromomethyl compound as a yellow oil which crystallized upon standing.

Step 2: Preparation of 4-[5-4-hydroxymethylphenyl)-3-(trifluoromethyl)-1H-pyrazol-1-yl]benzenesulfonamide The bromo methyl compound from Step 1 was dissolved in 30 mL of acetone/4 mL of $H_2O$ and refluxed for 120 hours. The reaction was concentrated and the residue dissolved in 50 mL of ethyl acetate and dried over $MgSO_4$. The crude product was obtained as an amber oil. The oil was purified via radial band chromatography eluting with 30% ethyl acetate/70% hexane to afford the title compound as a yellow solid. Anal. calc'd for $C_{17}H_{14}N_3O_3SF_3$: C, 51.38; H, 3.55; N, 10.57. Found: C, 51.28; H, 3.59; N, 10.31.

EXAMPLE 12

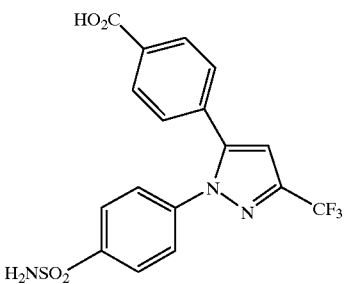

4-[1-(4-Aminosulfonyl)phenyl)-3-(trifluoromethyl)-1H-pyrazol-5-yl]benzoic acid

To the product from Example 11 in 2 mL of acetone was added 1.33 M Jones reagent until an orange color persisted. The reaction was poured into 20 mL of ethyl acetate and 20 mL of $H_2O$ and the organic layer separated, washed with saturated sodium bisulfite and dried over $MgSO_4$. The crude product was filtered through silica gel/Celite to afford the title compound as a yellow solid HRMS m/z 411.0507 (calc'd for $C_{17}H_{12}N_3O_4SF_3$, 411.0500).

The following compounds in Table I were prepared according to procedures similar to that exemplified in Examples 1–12, with the substitution of the appropriate acetophenone.

TABLE I

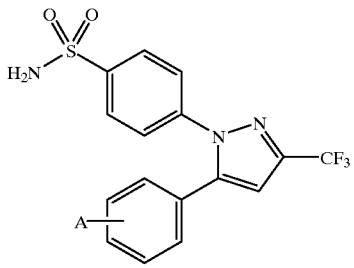

| Ex. | A | M.P. (° C.) | Analytical |
|---|---|---|---|
| 13 | 4-Br | 137–139 | Calc. C, 43.07; H, 2.48; N, 9.42; Br, 17.91 |
|    |      |         | Obs. C, 43.01; H, 2.32; N, 9.39; Br, 17.62 |
| 14 | 3-Cl | 154–155 | Calc. C, 47.83; H, 2.76; N, 10.46; Cl, 8.82 |
|    |      |         | Obs. C, 47.61; H, 2.85; N, 10.31; Cl, 8.43 |
| 15 | 2-Cl | 159–160 | Calc. C, 47.83; H, 2.76; N, 10.46 |
|    |      |         | Obs. C, 47.47; H, 2.65; N, 10.31 |
| 16 | 4-CF$_3$ | 144–145 | Calc. C, 46.90; H, 2.55; N, 9.65 |
|    |          |         | Found: C, 46.98; H, 2.57; N, 9.61 |
| 17 | 4-F | 168–169 | Calc. C, 49.87; H, 2.88; N, 10.90 |
|    |     |         | Found: C, 49.83; H, 2.89; N, 10.86 |
| 18 | H | 164–165 | Calc. C, 52.31; H, 3.29; N, 11.43 |
|    |   |         | Found: C, 52.14; H, 3.07; N, 11.34 |
| 19 | 4-OCH$_3$ | 153–154 | Calc. C, 51.38; H, 3.55; N, 10.57 |
|    |           |         | Found: C, 51.00; H, 3.48; N, 10.24 |
| 20 | 4-OCF$_3$ | 101–103 | Calc. C, 45.24; H, 2.46; N, 9.31 |
|    |           |         | Found: C, 45.22; H, 2.37; N, 9.29 |
| 21 | 2-CH$_3$ | 126–128 | Calc. C, 53.54; H, 3.70; N, 11.02 |
|    |          |         | Found: C, 53.52; H, 3.55; N, 11.06 |
| 22 | 2,4-di-F | 127–130 | M + H 404 |
| 23 | 2,6-di-F | 178–180 | M + H 404 |
| 24 | 4-CN | 196–197.5 | |
| 25 | 3,4-di-Cl | 145–147 | Calc. C, 44.05; H, 2.31; N, 9.63; Cl, 16.25 |
|    |           |         | Found: C, 44.00; H, 2.20; N, 9.63; Cl, 16.46 |
| 26 | 2,4-di-Cl | 153–155 | Calc. C, 43.87; H, 2.35; N, 9.59 |
|    |           |         | Found: C, 43.78; H, 2.13; N, 9.56 |
| 27 | 4-NO$_2$ | 169–172 (dec) | Calc. C, 46.61; H, 2.69; N, 13.59; S, 7.78 |
|    |          |               | Obs.: C, 46.52; H, 2.67; N, 13.51; S, 7.84 |
| 28 | 2-F | 165–166 | Calc. C, 49.87; H, 2.88; N, 10.90 |
|    |     |         | Found: C, 49.49; H, 2.62; N, 10.79 |
| 29 | 4-NH$_2$ | 124–127 (dec) | HRMS: 382.0671 |
| 30 | 4-F, 2-CH$_3$ | 170–171 | Calc. C, 51.13; H, 3.28; N, 10.52 |
|    |               |         | Found: C, 50.83, H, 2.98; N, 10.55 |
| 31 | 3-CH$_3$ | 135–137 | Calc. C, 53.54; H, 3.70; N, 11.02 |
|    |          |         | Found: C, 53.15; H, 3.58; N, 10.96 |
| 32 | 4-OCH$_2$CH$_3$ | 141–142 | Calc. C, 51.43; H, 4.08; N, 9.99 |
|    |                  |         | Found: C, 51.49; H, 3.80; N, 10.08 |
| 33 | 4-OCH$_3$, 3,5-di-CH$_3$ | 143–144 | Calc. C, 53.64; H, 4.26; N, 9.87 |
|    |                           |         | Found: C, 53.49; H, 4.39; N, 9.64 |
| 34 | 3-F | 143–144 | Calc. C, 49.87; H, 2.88; N, 10.90 |
|    |     |         | Found: C, 49.80; H, 2.80; N, 10.84 |
| 35 | 4-OCH$_3$, 3-F | 155–156 | Calc. C, 49.16; H, 3.15; N, 10.11 |
|    |                |         | Found: C, 48.77; H, 2.93; N, 9.96 |
| 36 | 4-SCH$_3$ | 165–166 | Calc. C, 49.39; H, 3.41; N; 10.16 |
|    |           |         | Found: C, 49.48; H, 3.46; N, 10.26 |
| 37 | 4-Cl, 3-CH$_3$ | ND | Calc. C, 49.10; H, 3.15; N, 10.11 |
|    |                |    | Found: C, 49.00; H, 3.00; N, 10.10 |
| 38 | 4-CH$_2$CH$_3$ | ND | Calc. C, 54.68; H, 4.08; N, 10.63 |
|    |                 |    | Found: C, 54.54; H, 3.73; N, 10.67 |
| 39 | 2,4-di-CH$_3$ | ND | Calc. C, 54.68; H, 4.08; N, 10.63 |
|    |               |    | Found: C, 54.31; H, 4.32; N, 10.39 |
| 40 | 2-OCH$_3$ | 167–168 | Calc. C, 51.38; H, 3.55; N, 10.57 |
|    |           |         | Found: C, 51.29; H, 3.34; N, 10.52 |
| 41 | 4-OCH$_3$, 3-CH$_3$ | 146–147 | |
| 42 | 4-SCH$_3$, 3-Br | 141–144 | HRMS: 490.9595 |

TABLE I-continued

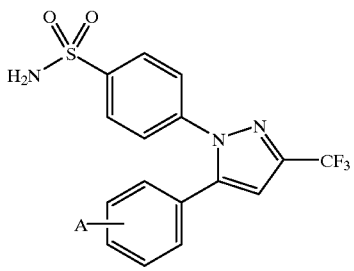

| Ex. | A | M.P. (° C.) | Analytical |
|---|---|---|---|
| 43 | 4-CH$_3$, 3-Cl | 186–190 | Calc. C, 49.10; H, 3.15; N, 10.11<br>Found: C, 49.21; H, 3.17; N, 10.10 |
| 44 | 3,4-di-OCH$_3$ | 192–193 | Calc. C, 50.58; H, 3.77; N, 9.83<br>Found: C, 50.58; H, 3.83; N, 9.72 |
| 45 | 4-OCH$_3$, 3-Cl | 166–168 | Calc. C, 47.29; H, 3.03; N, 9.73<br>Found: C, 47.21; H, 2.91; N, 9.55 |
| 46 | 4-OCH$_3$, 3-Cl, 5-CH$_3$ | ND | Calc. C, 48.49; H, 3.39; N, 9.42<br>Found: C, 48.27; H, 3.42; N, 9.22 |
| 47 | 2-OCH$_3$, 4-F | 163–164 | Calc. C, 49.16; H, 3.15; N, 10.12<br>Found: C, 49.32; H, 3.27; N, 10.18 |
| 48 | 2,4-di-OCH$_3$ | ND | Calc. C, 50.58; H, 3.77; N, 9.83<br>Found: C, 50.40; H, 3.78; N, 9.83 |
| 49 | 4-F, 3-Cl | ND | Calc. C, 45.78; H, 2.40; N, 10.01<br>Found: C, 45.75; H, 2.34; N, 10.15 |
| 50 | 4-OCH$_3$, 3,5-di-F | ND | Calc. C, 47.12; H, 2.79; N, 9.70<br>Found: C, 46.72; H, 2.75; N, 9.54 |
| 51 | 4-SCH$_3$, 3-F | ND | Calc. C, 47.33; H, 3.04; N, 9.74<br>Found: C, 47.25; H, 3.39; N, 9.45 |
| 52 | 4-SCH$_3$, 3-Cl | ND | Calc. C, 45.59; H, 2.93; N, 9.38<br>Found: C, 45.56; H, 2.76; N, 9.52 |
| 53 | 4-N(CH$_3$)$_2$ | ND | HRMS: 410.1016 |
| 54 | 4-N(CH$_2$CH$_3$)$_2$ | ND | HRMS: 438.1353 |

EXAMPLE 55

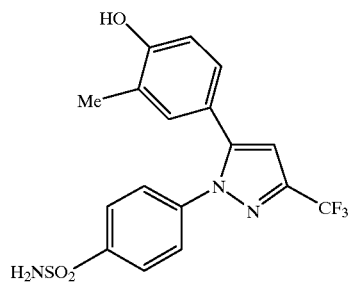

4-[5-(4-Hydroxy-3-methylphenyl)-3-(trifluoromethyl)-1H-pyrazol-1-yl]benzenesulfonamide To a solution of the product of Example 41 (240 mg, 0.58 mmol) in DMF (3 mL) was added NaSMe (205 mg, 2.9 mmol) and the mixture heated to reflux for 2 hours. The mixture was cooled, poured into 0.1N HCl and extracted with EtOAc (3×). The combined extracts were dried over MgSO$_4$ and concentrated. Flash chromatography using 1:1 hexane/ethyl acetate provided 31 mg of the title compound: Anal. calc'd for C$_{17}$H$_{14}$N$_3$O$_3$SF$_3$.0.25 H$_2$O: C, 50.80; H, 3.64; N, 10.45. Found: C, 50.71; H, 3.47; N, 10.39.

EXAMPLE 56

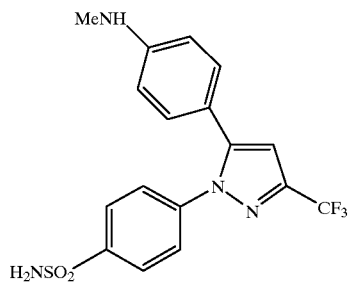

4-[5-(4-(N-Methylamino)phenyl)-3-(trifluoromethyl)-1H-pyrazol-1-yl]benzenesulfonamide To a solution of the product of Example 53 (431 mg, 1.0 mmol) in 10 ml methanol was added 36 mg (0.17 mmol) ruthenium (III) chloride hydrate, followed by 1.5 mL 30% hydrogen peroxide (14.7 mmol) over 2 hours. The reaction was quenched with 25 mL of 1M KOH in methanol and concentrated to give 1.24 g of a brown solid. The solid was purified on a prep plate eluting with 2/97/1 methanol/methylene chloride/ammonium chloride to give 52 mg (0.14 mmol, 12%) of the product as a yellow solid.

EXAMPLE 57

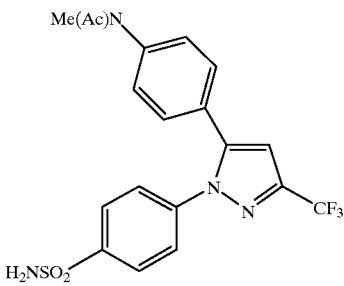

N-[4-[1-[4-(Aminosulfonyl)phenyl]-3-(trifluoromethyl)-1H-pyrazol-5-yl]phenyl]-N-methylacetamide 19 mg (0.051 mmol) of the product from Example 56 was treated with 0.03 mL acetic anhydride (0.32 mmol) and 0.03 mL triethylamine (0.22 mmol) in 3 mL methylene chloride at room temperature for 12 hours. The reaction mixtured was concentrated and the residue dissolved in 10 mL ethyl acetate. After washing with brine (2×10 mL), the solution was dried over MgSO$_4$, filtered and concentrated to afford the title compound (18.4 mg, 74%) as a yellow solid: HRMS m/e 438.0976 (calc'd for $C_{19}H_{17}N_4O_3SF_3$, 438.0974).

EXAMPLE 58

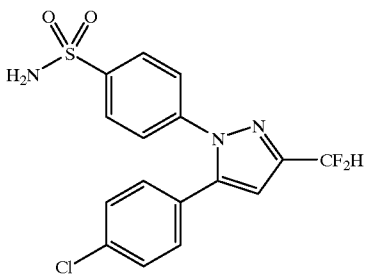

4-[5-(4-Chlorophenyl)-3-(difluoromethyl)-1H-pyrazol-1-yl]benzenesulfonamide

Step 1: Preparation of 4,4-difluoro-1-[4-(chloro)phenyl]-butane-1,3-dione.

Ethyl difluoroacetate (24.82 g, 200 mmol) was placed in a 500 mL three-necked round bottom flask, and dissolved in diethyl ester (200 mL). To the stirred solution was added 25% sodium methoxide in methanol (48 mL, 210 mmol) via an addition funnel over a 2 minute period. Next, 4'-chloroacetophenone (25.94 g, 200 mmol) was dissolved in diethyl ether (50 mL), and added to the reaction dropwise over 5 minutes. After stirring overnight (18 hours), 1N HCl (250 mL) and ether (250 mL) were added. The organic layer was collected, washed with brine (250 mL), dried over MgSO$_4$, filtered, and concentrated in vacuo to give 46.3 g of a yellow solid. The solid was recrystallized from methylene chloride and iso-octane to give 31.96 g (69%) of the dione: mp 65–66.5° C.

Step 2: Preparation of 4-[5-(4-chlorophenyl)-3-(difluoromethyl)-1H-pyrazol-1-yl]benzenesulfonamide 4-Sulphonamidophenylhydrazine hydrochloride (1.45 g, 6.5 mmol 1.3 equivalent) and 4,4-difluoro-1-[4 -(chloro)phenyl]butane-1,3-dione from Step 1 (1.16 g, 5 mmol) were dissolved in ethanol (10 mL). The reaction was heated to reflux and stirred for 20 hours. After cooling to room temperature, the reaction mixture was concentrated in vacuo. The residue was taken up in ethyl acetate (100 mL), washed with water (100 mL) and with brine (100 mL), dried over MgSO$_4$, filtered, and concentrated in vacuo to give 1.97 g of a light brown solid which was recrystallized from ethanol and water to give 4-[5-(4-chlorophenyl)-3-(difluoromethyl)-1H-pyrazol-1-yl]benzenesulfonamide (1.6 g, 83%): mp 185–186° C.

EXAMPLE 59

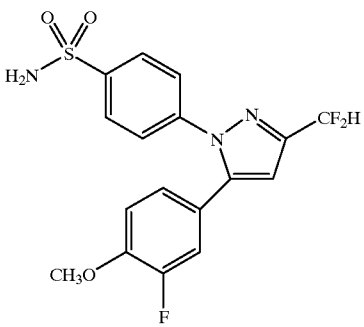

4-[5-(3-Fluoro-4-methoxyphenyl)-3-(difluoromethyl)-1H-pyrazol-1-yl]benzenesulfonamide Step 1: Preparation of 3'-fluoro-4'-methoxy-acetophenone.

Aluminum chloride (80.0 g, 0.6 mol) and chloroform (750 mL) were placed in a 2 L three-necked round bottom flask fitted with a mechanical stirrer and cooled by means of an ice bath. To the stirred solution acetyl chloride (51.0 g, 0.65 mol) was added dropwise, maintaining the temperature between 5–10° C. The mixture was stirred for 10 minutes at 5° C. before the dropwise addition at 5–10° C. of 2-fluoroanisole (63.6 g, 0.5 mol). The mixture was stirred at 0–10° C. for 1 hour and poured into ice (1 L). The resultant layers were separated and the aqueous layer was extracted with dichloromethane (2×250 mL). The combined organic layers were washed with water (2×150 mL), dried over anhydrous MgSO$_4$, filtered and concentrated in vacuo to a volume of 300 mL. Hexanes were added and a white solid formed which was isolated by filtration and air dried. This material was recrystallized from a mixture of dichloromethane and hexanes to afford (77.2 g, 92%) of material suitable for use in the next step: mp 92–94° C.; $^1$H NMR (DMSO-d$_6$) 7.8 (m, 2H), 7.3 (t, 1H), 3.9 (s, 3H), 2.5 (s, 3H).

Step 2: Preparation of 4,4-difluoro-1-(3-fluoro-4-methoxyphenyl)-butane-1,3-dione.

Ethyl difluoroacetate (4.06 g, 32.7 mmol) was placed in a 250 mL Erlenmeyer flask, and dissolved in methyl tert-butyl ether (50 mL). To the stirred solution was added 25% sodium methoxide (7.07 g, 32.7 mmol) followed by 3'-fluoro-4'-methoxyacetophenone from Step 1 (5.0 g, 29.7 mmol). After stirring for 16 hours, 1N HCl (50 mL) was added. The organic layer was collected, washed with water (2×50 mL), dried over anhydrous MgSO$_4$, filtered, and added to hexanes to precipitate a tan solid (7.0 g, 96%): mp 70–72° C.; $^1$H NMR (DMSO-d$_6$) 8.0 (m, 3H), 7.3 (t, 1H), 6.9 (s, 1H), 6.5 (t, 1H), 3.9 (s, 3H).

Step 3: Preparation of 4-[5-(3-fluoro-4-methoxyphenyl)-3-(difluoromethyl)-1H-pyrazol-1-yl]benzenesulfonamide.

4,4-Difluoro-1-(3-fluoro-4-methoxyphenyl)-butane-1,3-dione from Step 2 (7.0 g, 28.4 mmol) was dissolved in ethanol (150 mL). To the stirred mixture was added 4-sulphonamidophenylhydrazine hydrochloride (7.4 g, 33 mmol) and stirred at reflux overnight (16 hours). The mixture was cooled and water was added until crystals slowly appeared. The product was isolated by filtration and air dried to provide the desired product as a light tan solid (9.8 g, 87%): mp 159–161° C.; $^1$H NMR (DMSO-d$_6$) 7.85 (d, 2H), 7.5 (m, 6H), 7.3–6.9 (m, 5H), 3.8 (s 3H). Anal. Calc'd for $C_{17}H_{14}N_3SO_3F_3$: C, 51.38; H, 3.55; N, 10.57. Found: C, 51.46; H, 3.52; N, 10.63.

EXAMPLE 60

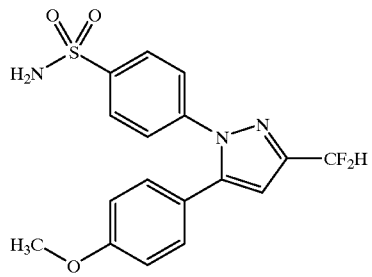

4-[3-Difluoromethyl-5-(4-methoxyphenyl)-1-H-pyrazol-1-yl]benzenesulfonamide

Step 1. Preparation of 4,4,4-trifluoromethyl-1-(4-methoxyphenyl)butane-1,3-dione.

To a stirred solution of 4-methoxyacetophenone (11.43 g, 76.11 mmol) and ethyl difluoroacetate (8.4 mL, 10.4 g, 83.72 mmol) in diethyl ether (300 mL) in a 500 mL round bottomed flask was added sodium methoxide in methanol (18.2 mL of a 25% solution, 79.91 mmol). The solution became a dark lavender color within thirty minutes, and then a gray suspension within 1.5 hours. The reaction was stirred for 60 hours. Diethyl ether (300 mL) was added and the mixture was acidified (pH 2) with 1N HCl. The mixture was transferred to a separatory funnel, mixed and separated. The ethereal phase was washed with water, dried over magnesium sulfate, and filtered. Hexane was added causing precipitation of an orange solid 5.25 g of 4,4,4-trifluoromethyl-1-(4-methoxyphenyl)butane-1,3-dione. An additional 3.43 g of product was obtained by recrystallization of the concentrated mother liquor from hexane: $^1$H NMR (CDCl$_3$) 400 mHz 15.58 (br s, 1 H), 7.94 (d, J=8.87 Hz, 2H), 6.98 (d, J=8.87 Hz, 2H), 6.49 (s, 1H), 6.00 (t, J=54.55 Hz, 1 H), 3.89 (s, 3H).

Step 2. Preparation of 4-[5-(4-methoxyphenyl)-3-difluoromethyl-1-H-pyrazol-1-yl]benzenesulfonamide A mixture of 4,4,4-trifluoromethyl-1-(4-methoxyphenyl)butane-1,3-dione from Step 1 (2.006 g, 8.79 mmol) and 4-sulfonamidophenylhydrazine hydrochloride salt (2.065 g, 9.23 mmol) dissolved in ethanol (25 mL) was heated to reflux for 16 hours. The reaction was cooled to room temperature, was concentrated and recrystallized from methanol yielding 4-[5-(4-methoxyphenyl)-3-difluoromethyl-1-H-pyrazol-1-yl]benzenesulfonamide as fluffy tan crystals (1.49 g, 45%): mp 133–135° C.; $^1$H NMR (CDCl$_3$) 300 mHz 7.90 (d, J=8.863 Hz, 2H), 7.45 (d, J=8.863 Hz, 2H), 7.14 (d, J=8.863 Hz, 2H), 6.88 (d, J=8.863 Hz, 2H), 6.77 (t, J=56.47 Hz, 1H), 6.68 (s, 1 H), 4.96(br s, 2 H), 3.83(s, 3 H); $^{19}$NMR (CDCl$_3$) 300 mHz –112.70 (d, J=57.9 Hz). High resolution mass spectrum Calc'd for $C_{17}H_{15}F_2N_3O_3S$: 379.0802. Found: 379.0839. Elemental analysis calc'd for $C_{17}H_{15}F_2N_3O_3S$: C, 53.82; H, 3.99; N, 11.08. Found: C, 53.75; H, 3.99; N, 11.04.

The following compounds in Table II were obtained according to procedures similar to that exemplified in Examples 58–60, with the substitution of the appropriate acetophenone.

TABLE II

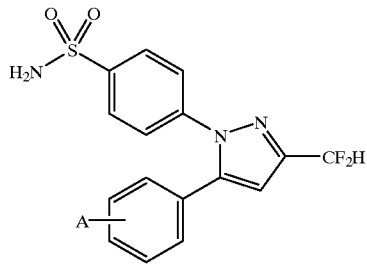

| Ex. | A | M.P. (° C.) | Anal. |
|---|---|---|---|
| 61 | 4-CF$_3$ | 202–205 | M + H 418 |
| 62 | 4-SCH$_3$ | 157–158 | |
| 63 | 4-(1-morpholino) | 167–171 | M + 434 |
| 64 | 4-CH$_3$ | 158–159 | Calc. C, 56.19; H, 4.16; N, 11.56 |
| | | | Obs. C, 56.25; H, 4.17; N, 11.61 |
| 65 | 3,4-di-CH$_3$ | 168–171 | Calc. C, 57.28; H, 4.54; N, 11.13 |
| | | | Obs. C, 57.34; H, 4.59; N, 11.16 |
| 66 | 4-CO$_2$CH$_3$ | 157–158 | Calc. C, 53.56; H, 3.09; N, 15.61 |
| | | | Obs. C, 53.45; H, 3.11; N, 15.62 |
| 67 | 4-CONH$_2$ | 235–236 | HRMS: 393.0833 |
| 68 | 4-CO$_2$H | 258–260 (dec) | HRMS: 394.0662 |
| 69 | 2-F, 4-OCH$_3$ | 138–140 | Calc. C, 51.38; H, 3.55; N, 10.57 |
| | | | Obs. C, 51.14; H, 3.48; N, 10.40 |
| 70 | 4-CN | 222–224 | Calc. C, 54.54; H, 3.23; N, 14.97 |
| | | | Obs.: C, 54.58; H, 3.21; N, 15.06 |
| 71 | 3-Cl, 4-CH$_3$ | 156–158 | Calc. C, 51.32; H, 3.55; N, 10.56 |
| | | | Obs: C, 51.46; H, 3.53; N, 10.53 |

TABLE II-continued

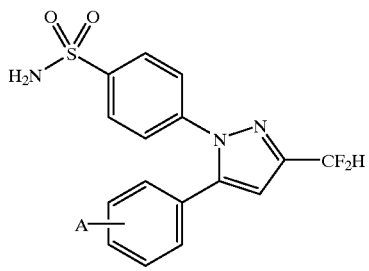

| Ex. | A | M.P. (° C.) | Anal. |
|---|---|---|---|
| 72 | 3-Cl, 4-OCH₃ | 160 | Calc. C, 49.34; H, 3.41; N, 10.15; Cl, 8.57; S, 7.75 |
| | | | Obs.: C, 49.41; H, 3.37; N, 10.17; Cl, 8.62; S, 7.67 |
| 73 | 4-Cl, 3-CH₃ | 163–165 | Calc. C, 51.32; H, 3.55; N, 10.56 |
| | | | Obs.: C, 51.42; H, 3.57; N, 10.53 |
| 74 | 3,4-di-OCH₃ | 181–185 | Calc. C, 52.81; H, 4.19; N, 10.26 |
| | | | Obs.: C, 52.86; H, 4.19; N, 10.20 |
| 75 | 3,5-di-Cl, 4-OCH₃ | 170–173 | Calc. C, 45.55; H, 2.92; N, 9.37 |
| | | | Obs.: C, 45.83; H, 3.05; N, 9.31 |
| 76 | 3,5-di-F, 4-OCH₃ | 149–150 | Calc. C, 49.16; H, 3.15; N, 10.12 |
| | | | Obs.: C, 49.24; H, 3.16; N, 10.13 |
| 77 | 2-OCH₃ | 129–132 | Calc. C, 53.82; H, 3.99; N, 11.08 |
| | | | Obs.: C, 53.82; H, 3.97; N, 11.15 |
| 78 | 3-Br, 4-OCH₃ | 164 | HRMS: 456.9883 |
| 79 | 4-SO₂CH₃ | 209–210 | |
| 80 | 4-C₆H₅ | 167–170 | M + 425 |
| 81 | H | 171–172 | HRMS: 349.0737 |

EXAMPLE 82

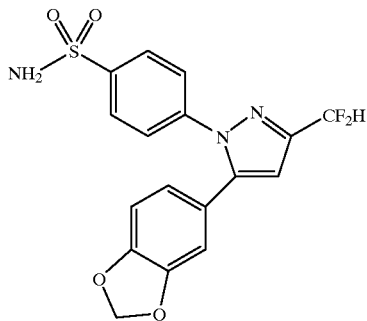

4-[5-(1,3-Benzodioxol-5-yl)-3-(difluoromethyl)-1H-pyrazol-1-yl]benzenesulfonamide Step 1. Preparation of 1-(1,3-benzodioxol-5-yl)-4,4-difluorobutane-1,3-dione.

Ethyl difluoroacetate (1.72 g, 11 mmol) was dissolved in ether (25 mL). To the stirred solution was added 25% sodium methoxide (2.38 g, 11 mmol) followed by 3',4'-(methylenedioxy)acetophenone (1.64 g, 10 mmol). After stirring 16 hours, 1N HCl (25 mL) was added. The organic layer was collected and washed with water (2×25 mL), dried over magnesium sulfate, filtered, and concentrated. The resulting crude dione was used in the next step without further purification or characterization.

Step 2. Preparation of 5-(1,3-benzodioxol-5-yl)-4-[3-(difluoromethyl)-1H-pyrazol-1-yl]benzenesulfonamide.

1-(1,3-Benzodioxol-5-yl)-4,4-difluorobutane-1,3-dione from Step 1 (2.4 g, 10 mmol) was dissolved in ethanol (100 mL). To the stirred mixture was added 4-sulfonamidophenylhydrazine hydrochloride (2.46 g, 11 mmol) and heated to reflux for 16 hours. The mixture was cooled and water was added until crystals slowly appeared. Filtration yielded a light tan solid (3.3 g, 84%): mp 214–218° C.; ¹H NMR (D₆-DMSO): 7.86 (d, J=8.7 Hz, 3H), 7.51 (d, J=8.7 Hz, 2H), 7.49 (brs, 2H), 7.3–6.7 (m, 5H), 6.06(s, 2H). Anal. Calc'd for C₁₇H₁₃N₃SO₄F₂: C, 51.91; H, 3.33; N, 10.68. Found: C, 51.90; H, 3.25; N. 10.65.

EXAMPLE 83

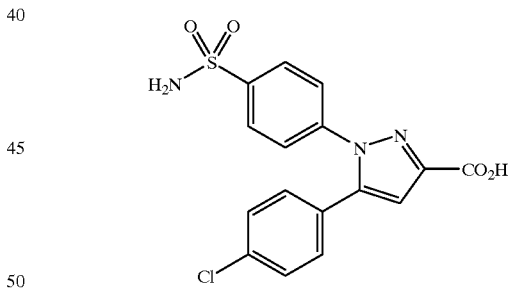

4-[4-(Aminosulfonyl)phenyl]-5-(4-chlorophenyl)-1H-pyrazole-3-carboxylic acid

Step 1: Preparation of methyl-4-[4-(chloro)phenyl]-2,4-dioxobutanoate.

Dimethyl oxalate (23.6 g, 200 mmol) was placed in a 500 mL three-necked round bottom flask, and dissolved in diethyl ether (200 mL). To the stirred solution was added 25% sodium methoxide in methanol (48 mL, 210 mmol): via an addition funnel over a 2 minute period. Next, 4'-chloroacetophenone (25.94 g, 200 mmol) was dissolved in diethyl ether (50 mL), and added to the reaction dropwise over 3 minutes. After stirring overnight (18 hours), 1N HCl (400 mL) and ethyl acetate (750 mL) were added. The organic layer was collected, washed with brine (350 mL), dried over MgSO₄, filtered, and concentrated in vacuo to give 45.7 g of a yellow solid. The solid was recrystallized from ethyl acetate and iso-octane to give 23 g (48%) of the dione: mp 108.5–110.5° C.

Step 3: Preparation of 4-[4-(aminosulfonyl)phenyl)-5-(4-chlorophenyl)-1H-pyrazole-3-carboxylic acid 4-Sulphonamidophenylhydrazine hydrochloride (1.45 g, 6.5 mmol, 1.3 equivalent) and methyl-4-[4-(chloro)phenyl]-2,4-dioxobutanoate (1.2 g, 5 mmol) were dissolved in ethanol (50 mL). The reaction was heated to reflux and stirred for 20 hours. After cooling to room temperature, the reaction mixture was concentrated in vacuo. The residue was taken up in ethyl acetate (200 mL) and washed with water (100 mL) and brine (100 mL), dried over $MgSO_4$, filtered and concentrated in vacuo to give 1.7 g of a light brown solid which was recrystallized from methanol and water to yield 1.6 g (85%) of a white solid. This material was dissolved in methanol (150 mL) and 3N NaOH (75 mL) and stirred at reflux for 3 hours. The methanol was removed in vacuo and the aqueous solution acidified with concentrated HCl. The product was extracted into ethyl acetate (200 mL), which was washed with brine (100 mL), dried over $MgSO_4$ filtered and concentrated to give 4-[4-(aminosulfonyl)phenyl]-5-(4-chlorophenyl)-1H-pyrazole-3-carboxylic acid, 1.4 g (74%): mp 135° C. (dec).

EXAMPLE 84

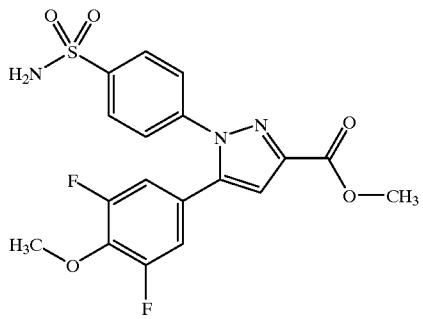

Methyl 1(4-aminosulfonylphenyl)-5-(3,5-difluoro-4-methoxyphenyl)-1-H-pyrazole-3-carboxylate Step 1. Preparation of 3,5-difluoro-4-methoxy-acetophenone.

To a stirred suspension of $AlCl_3$ (24.05 g, 180.40 mmol) in chloroform (300 mL, dried by passage through alumina at 4° C. (ice bath) under nitrogen was added acetyl chloride (11.0 mL, 152.65 mmol) over 20 minutes. This chilled suspension was stirred at 0° C. for 30 minutes and 2,6-difluoro anisole was added dropwise over 30 minutes. The resulting suspension was warmed to room temperature and stirred overnight. The reaction was quenched by slowly pouring it into a rapidly stirred ice/water mixture. The water layer was extracted with methylene chloride (2×50 mL) and the organic phases were combined and concentrated in vacuo yielding a clear mobile oil. In a 50 mL round bottomed flask was added the above clear oil, DMF (25 mL), $K_2CO_3$ (15 g). Methyl iodide (6 mL) was added and the suspension stirred at 45° C. under nitrogen overnight. Water (1 mL) was added and the mixture was heated for an additional 14 hours. The crude reaction mixture was cooled to room temperature, diluted with water (250 mL) and extracted with diethyl ether (3×100 mL). The ether phase was washed with sodium bicarbonate saturated solution, potassium bisulfate (0.1 N solution), dried over $MgSO_4$, filtered and concentrated in vacuo yielding a clear mobile liquid. This liquid was distilled (30° C., 1 mm) yielding 12.5 g of a clear liquid which was a mixture of 3,5-difluoro-4-methoxyacetophenone and 3,5-difluoro-4-acetoxyacetophenone in an 85:15 ratio. The yield based upon this ratio was 41%. This ketone was used as is.

Step 2. Preparation of methyl 1-(4-aminosulfonylphenyl)-5-(3,5-difluoro-4-methoxyphenyl)-1-H-pyrazole-3-carboxylate To a stirred solution of 3,5-difluoro-4-methoxyacetophenone from Step 1 (6.46 g, 34.70 mmol) and dimethyl oxalate (6.15 g, 52.05 mmol) in methanol (80 mL), was added sodium methoxide solution (13.4 mL of 25% solution, 58.99 mmol) in one portion and the reaction stirred overnight. The crude reaction was diluted with methylene chloride, washed with potassium bisulfate (0.1N solution), brine, dried over $MgSO_4$, filtered, and concentrated in vacuo yielding methyl 4-(3,5-difluoro-4-methoxyphenyl)-2,4-dioxo-butanoate as an off white crystalline solid which was used as is. A mixture of 4-(3,5-difluoro-4-methoxyphenyl)-2,4-dioxo-butanoate and 4-sulfonamidophenylhydrazine hydrochloride salt (7.76 g, 34.70 mmol) dissolved in methanol was warmed to reflux for 9 hours. Upon allowing the clear reaction to cool to room temperature, a crystalline precipitate formed which was collected by vacuum filtration yielding 5.45 g, (37% based upon the 3,5-difluoro-4-methoxyacetophenone) of methyl 1-(4-aminosulfonylphenyl)-5-(3,5-difluoro-4-methoxyphenyl)-1-H-pyrazole-3-carboxylate as an off-white solid: mp 185–190° C.; $^1H$ NMR ($CDCl_3$/300 mHz) 7.95 (d, J=8.86, 2H), 7.49 (d, J=8.86, 2H), 7.02 (s, 1H), 6.77 (m, 2H), 4.99 (s, 2H), 4.04 (s, 3 H), 3.98 (s, 3H); $^{19}F$ NMR ($CDCl_3$/300 mHz) −126.66. Anal. Calc'd for $C_{17}H_{13}F_2N_3O_3S$: C, 51.06; H, 3.57; N, 9.92. Found: C, 51.06; H, 3.54, N, 9.99.

EXAMPLE 85

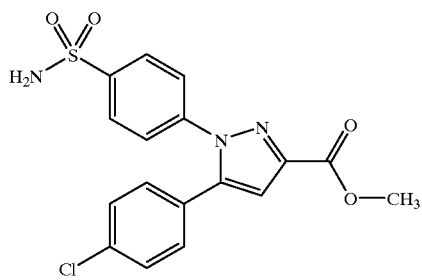

Methyl [1-(4-aminosulfonylphenyl)-5-(4-chlorophenyl)-1H-pyrazole-3-yl]carboxylate Step 1. Preparation of methyl 4-[4-(chloro)phenyl]-2,4-dioxobutanoate Dimethyl oxalate (15.27 g, 0.129 mol) and 4'-chloroacetophenone (20.0 g, 0.129 mol) were charged to a 500 mL round-bottom flask, with provisions made for magnetic stirring, and diluted with methanol (300 mL).

Sodium methoxide (25% in methanol, 70 mL) was added in one portion. The reaction was stirred at room temperature for 16 hours. The reaction became an insoluble mass during this time. The solid was mechanically broken up, then concentrated hydrochloric acid (70 mL) was added, and the white suspension was stirred vigorously at room temperature for sixty minutes. The suspension was cooled to 0° C. and held for 30 minutes. The solid was filtered, and the filter cake was washed with cold water (100 mL). Upon drying, methyl 4-[4-(chloro)phenyl]-2,4-dioxobutanoate was obtained (16.94 g, 54.4%) as the enol: $^1$H NMR (CDCl$_3$/300 MHz) 7.94 (d, J=8.66 Hz, 2H), 7.48 (d, J=8.66 Hz, 2H), 7.04 (s, 1H), 3.95 (s, 3H), 3.48 (s, 1H).

Step 2. Preparation of methyl (1-(4-aminosulfonylphenyl)-5-(4-chlorophenyl)-1H-pyrazole-3-yl]carboxylate.

A 100 mL round-bottomed flask equipped with magnetic stirrer and nitrogen inlet was charged with methyl 4-[4-(chloro)phenyl]-2,4-dioxobutanoate from Step 1 (5.0 g, 20.78 mmol), 4-sulfonamidylphenylhydrazine hydrochloride (5.11 g, 22.86 mmol) and methanol (50 mL). The reaction vessel was heated to reflux and held for 16 hours. A precipitate formed overnight. The suspension was cooled to 0° C., held for 0.5 hour, filtered and washed with cold water to provide, after air-drying, 7.91 g (91%) of crude product. Recrystallized 3.50 g from boiling ethanol to yield 3.14 g (97%) of pure methyl [1-(4-aminosulfonylphenyl)-5-(4-chlorophenyl)-1H-pyrazole-3 -yl]carboxylate: mp 227° C.; $^1$H NMR (CDCl$_3$/300 MHz) 7.91 (d, J=8.86 Hz, 2H), 7.44 (d, J=8.86 Hz, 2H), 7.33 (d, J=8.66 Hz, 2H), 7.14 (d, J=8.66 Hz, 2H), 7.03 (s, 1H), 3.96 (s, 3H). Mass Spectrum, MH+=392. Anal. Calc'd for C$_{17}$H$_{14}$N$_3$O$_4$ClS: C, 52.11; H, 3.60; N, 10.72; Cl, 9.05; S, 8.18. Found: C, 52.07; H, 3.57; N, 10.76, Cl, 9.11; S, 8.27.

EXAMPLE 86

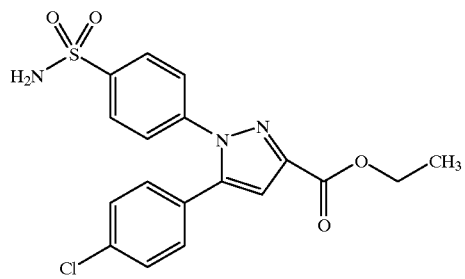

Ethyl [1-(4-aminosulfonylphenyl)-5-(4-chlorophenyl)-1H-pyrazole-3-yl]carboxylate Methyl [1-(4-aminosulfonylphenyl)-5-(4-chlorophenyl)-1H-pyrazole-3-yl]carboxylate (Example 85) (0.10 g) was dissolved in absolute ethanol (10 mL and a catalytic amount of 21% NaOEt/EtOH was added. The reaction was stirred without temperature control for 72 hours, then water (10 mL) was added. The produce crystallized, the suspension was cooled to 0° C. and held for 30 minutes. The product was filtered, washed with water (5 mL) and dried to yield 0.071 g (70%) of a white solid: Mass Spectrum: MH+=406. Anal. Calc'd for C$_{18}$H$_{16}$N$_3$O$_4$ClS: C, 53.27; H, 3.97; N, 10.35; Cl, 8.74; S, 7.90. Found: C, 53.04; H, 4.00; N, 10.27; Cl, 8.69; S, 7.97.

The following compounds in Table III were prepared according to procedures similar to that exemplified in Examples 83–86, with the substitution of the appropriate reagents.

TABLE III

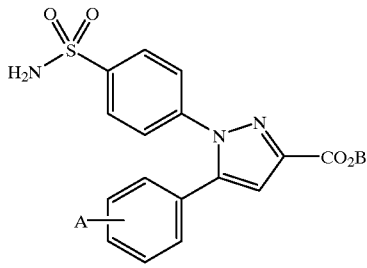

| Ex. | A | B | M.P. (° C.) | Analytical. |
|---|---|---|---|---|
| 87 | 4-NO$_2$ | —CH$_3$ | 216–220 | MH+ = 403 |
| 88 | 4-F | —CH$_3$ | ND | Calc. C, 54.40; H, 3.76; N, 11.19; S, 8.54 |
| | | | | Obs. C, 54.49; H, 3.70; N, 11.25; S, 8.50 |
| 89 | 4-NH$_2$ | —CH$_3$ | 267–269 (dec) | MH+ = 373 |
| 90 | 4-Br | —CH$_3$ | 221–224 | MH+ = 438 |
| 91 | 4-OCH$_3$ | —CH$_3$ | 169–171 | HRMS: 387.0930 |
| 92 | 4-CH$_3$ | —CH$_3$ | 213–215 | HRMS: 371.0965 |
| 93 | 4-CH$_3$ | —CH$_2$CH$_3$ | 219–220 | Calc. C, 59.21; H, 4.97; N, 10.90 |
| | | | | Obs. C, 58.73; H, 4.96; N, 10.78 |
| 94 | 4-Cl | —CH$_2$CH$_2$CH$_3$ | ND | Calc. C, 54.35; H, 4.32; N, 10.01; Cl, 8.44; S, 7.64 |
| | | | | Obs. C, 54.11; H, 4.28; N, 10.14; Cl, 8.54; S, 7.64 |
| 95 | 3,5-di-Cl, 4-OCH$_3$ | —CH$_3$ | 225–229 | |

EXAMPLE 96

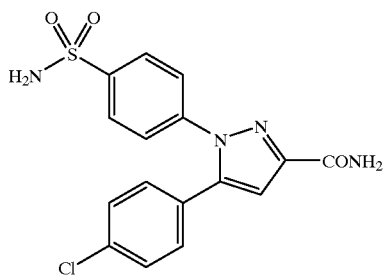

4-[4-(Aminosulfonyl)phenyl]-5-(4-chlorophenyl)-
1H-pyrazole-3-carboxamide

4-[4-(Aminosulfonyl)phenyl]-5-(4-chlorophenyl)-1H-pyrazole-3-carboxylic acid (Example 83) (1.08 g, 2.86 mmol), HOBt (0.66 g, 4.3 mmol) and EDC (0.66 g, 3.4 mmol) were dissolved in dimethylformamide (DMF) (20 mL) and stirred at ambient temperature for 5 minutes. To this solution was added NH$_4$OH (30%, 2.0 mL) and the reaction stirred for an additional 18 hours. This solution was then poured into ethyl acetate (200 mL) and 1N HCl (200 mL), shaken and separated. The organic layer was washed with saturated NaHCO$_3$ (150 mL) and brine (150 mL), dried over MgSO$_4$, filtered and concentrated to yield 0.9 g of a white solid which was recrystallized from ethyl acetate and iso-octane to yield 4-[4-(aminosulfonyl)phenyl]-5-(4-chlorophenyl)-1H-pyrazole-3-carboxamide (0.85 g, 79%): mp 108–110° C.

EXAMPLE 97

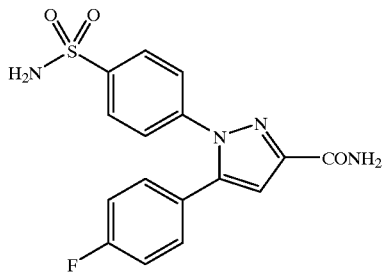

[1-(Aminosulfonylphenyl)-5-(4-fluorophenyl-1H-pyrazol-3-yl]carboxamide

A 250 mL three-neck round-bottom flask, equipped with a thermometer, gas sparging tube, reflux condenser and provisions for magnetic stirring, was charged with methyl [1-(4-aminosulfonylphenyl)-5-(4-fluorophenyl)-1H-pyrazol-3-yl]carboxylate (Example 88) (3.0 g, 7.99 mmol), methanol (100 mL), and a catalytic amount of sodium cyanide. Anhydrous ammonia gas was sparged through the reaction vessel for 16 hours without temperature control. The suspension turned a deep red during this time. The reaction was sparged with anhydrous nitrogen at room temperature for 20 minutes, cooled to 0° C. and held for 30 minutes. The solid was filtered and washed with cold water (50 mL) to yield, upon drying, 1.87 g (65%) of [1-(4-aminosulfonylphenyl)-5-(4-fluorophenyl)-1H-pyrazol-3-yl] carboxamide as a white solid: mp 214–216° C.; $^1$H NMR (CDCl$_3$/CD$_3$OD/300 MHz) 7.64 (d, J=8.66 Hz, 2H), 7.14 (d, J=8.66 Hz, 2H), 6.95 (m, 2H), 6.82–6.67 (m, 6H), 6.39 (s, 1H); $^{19}$F NMR (CDCl$_3$/CD$_3$OD/282.2 MHz) –112.00(m). Mass spectrum, MH+=361. Anal. Calc'd for C$_{16}$H$_{13}$N$_4$O$_3$FS: C, 53.33; H, 3.64; N, 15.55; S, 8.90. Found: C, 53.41; H, 3.69; N, 15.52; S, 8.96.

EXAMPLE 98

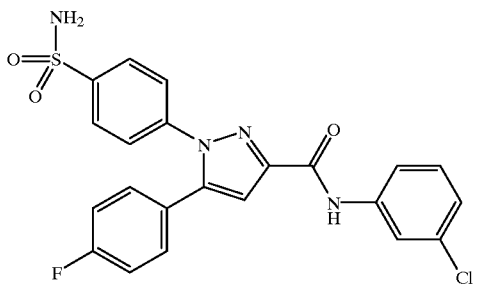

N-(3-Chlorophenyl)-[1-(4-aminosulfonylphenyl)-5-(4-fluorophenyl)-1H-pyrazol-3-yl]carboxamide Step 1. Preparation of methyl 4-[4-fluorophenyl]-2,4-dioxobutanoate.

Dimethyl oxalate (18.80 g, 0.159 mol) and 4'-fluoroacetophenone (20.0 g, 0.145 mol) were charged to a 1000 mL round-bottom flask and diluted with methanol (400 mL). The reaction flask was placed in a sonication bath (Bransonic 1200), and sodium methoxide (25% in methanol, 70 mL) was added over 25 minutes. The reaction was sonicated at 45° C. for 16 hours. The reaction became an insoluble mass during this time. The solid was mechanically broken up, then poured into a hydrochloric acid solution (1N, 500 mL). A magnetic stirrer was added, and the white suspension was stirred vigorously at room temperature for 60 minutes. The suspension was cooled to 0° C. and held for 30 minutes. The solid was filtered, and the filter cake was then washed with cold water (100 mL). Upon drying, methyl 4-[4-fluorophenyl]-2,4-diketobutanoate was obtained (22.91 g, 70.6%) as the enol: $^1$H NMR (CDCl$_3$/300 MHz) 8.03 (ddd, J=8.86 Hz, J=8.66 Hz, J=5.03 Hz, 2H), 7.19 (dd, J=8.86 Hz, J=8.66 Hz, 2H), 7.04 (s, 1H), 3.95(s, 3H). $^{19}$F NMR (CDCl$_3$/282.2 MHz) –103.9(m).

Step 2. Preparation of methyl 4-[1-(4-aminosulfonylphenyl)-5-(4-fluorophenyl)-1H-pyrazol-3-yl] carboxylate.

A 500 mL one-neck round-bottom flask equipped for magnetic stirring was charged with methyl 4-[4-fluorophenyl]-2,4-diketobutanoate from Step 1 (1.00 mg, 44.61 mmol), 4-sulfonamidylphenylhyrazine hydrochloride (10.98 g, 49.07 mmol) and methanol (200 mL). The suspension was heated and held at reflux for three hours, then cooled to room temperature. The suspension was cooled to 0° C., held for 30 minutes, filtered, washed with water (100 mL), and dried to yield 14.4 g (86%) of methyl 4-[1-(4-aminosulfonylphenyl)-5-(4-fluorophenyl)-1H-pyrazol-3-yl] carboxylate as a white solid: $^1$H NMR (CDCl$_3$/300 MHz) 7.85 (d, J=8.66 Hz, 2H), 7.36 (d, J=8.66 Hz, 2H), 7.18 (ddd, J=8.66 Hz, J=8.46 Hz, J=4.85 Hz, 2H), 7.00 (dd, J=8.66 Hz, J=8.46 Hz, 2H), 6.28 (s, 1H), 3.90 (s, 3H). $^{19}$F NMR (CDCl₃/282.2 MHz): -111.4(m). Mass spectrum, MH+= 376. Anal. Calc'd for $C_{17}H_{14}N_3O_4FS$: C, 54.40; H, 3.76; N, 11.19; S, 8.54. Found: C, 54.49; H, 3.70; N, 11.25; S, 8.50.

Step 3. Preparation of [1-(4-aminosulfonylphenyl)-5-(4-fluorophenyl)-1H-pyrazol-3-yl]carboxylic acid.

A 500 mL one-neck round-bottom flask, equipped with provisions for magnetic stirring, was charged with methyl 4-[1-(4-aminosulfonylphenyl)-5-(4-fluorophenyl)-1H-pyrazol-3-yl]carboxylate from Step 2 (10.0 g, 26.64 mmol) and tetrahydrofuran (200 mL). Aqueous sodium hydroxide (2.5N, 27 mL) and water (25 mL) were added, and the suspension was heated to reflux and held for 16 hours. The solids all dissolving during this time. The reaction was cooled to room temperature, and hydrochloric acid solution (1N, 110 mL) was added. The aqueous suspension was extracted with methylene chloride (2×200 mL). The combined organic solution was dried over anhydrous magnesium sulfate, filtered, and concentrated in vacuo to an oil. Trituration with 300 mL of methylene chloride yielded, upon filtration and drying, 9.0 g, (94%) of [1-(4-aminosulfonylphenyl)-5-(4-fluorophenyl)-1H-pyrazol-3-yl]carboxylic acid as a white solid: mp 138–142° C. (dec); ¹H NMR (CD₃OD/300 MHz) 7.93 (d, J=8.66 Hz, 2H), 7.51 (d, J=8.66 Hz, 2H), 7.31 (ddd, J=8.86 Hz, J=8.66 Hz, J=4.83 Hz, 2H), 7.11 (dd, J=8.86 Hz, J=8.66 Hz, 2H), 7.06 (s, 1H). ¹⁹F NMR (CD₃OD/282.2 MHz): -114.01(m).

Step 4. Preparation of N-(3-chlorophenyl)-[1-(4-aminosulfonylphenyl)-5-(4-fluorophenyl)-1H-pyrazol-3-yl]carboxamide A 100 mL one-neck round-bottom flask, equipped with provisions for magnetic stirring, was charged with [1-(4-aminosulfonylphenyl)-5-(4-fluorophenyl)-1H-pyrazol-3-yl]carboxylic acid from Step 3 (0.500 g, 1.38 mmol), 1-hydroxybenzotriazole hydrate (0.206 g, 1.522 mmol), 1-(3-dimethylaminopropyl)-3-ethylcarbodiimide hydrochloride (0.318 g, 1.66 mmol) and N,N-dimethylformamide (30 mL). The solution was stirred at room temperature for forty minutes, then 3-chloroaniline (0.154 mL, 1.453 mmol) was added. The reaction was held at room temperature for sixteen hours, then poured into an aqueous solution of citric acid (5%, 100 mL). The aqueous solution was extracted with ethyl acetate (2×60 mL), and the combined organic solutions were washed with aqueous citric acid (60 mL), saturated sodium bicarbonate solution (2×60 mL) and 50% saturated sodium chloride solution (2×60 mL). The organic solution was dried over anhydrous magnesium sulfate, filtered, and concentrated in vacuo to an oil. Trituration was 20 mL of dichloromethane yielded, upon filtration and drying, 0.439 g (67%) of N-(3-chlorophenyl)-[1-(4-aminosulfonylphenyl)-5-(4-fluorophenyl)-1H-pyrazol-3-yl]carboxamide as a white solid: mp 207–212° C.; ¹H NMR (CDCl₃/CD₃OD/300 MHz) 8.90 (s, 1H), 7.86 (d, J=8.66 Hz, 2H), 7.79 (t, J=2.01 Hz, 1H), 7.46 (dd, J=7.05 Hz, J=2.01 Hz, 1H), 7.33 (d, J=8.86 Hz, 2H), 7.21–7.11 (m, 3H), 7.02–6.94 (m, 4H). ¹⁹F NMR (CDCl₃/CD₃OD/282.2 MHz): -111.38(m). Mass spectrum, MH+=470. Anal. Calc'd for $C_{22}H_{16}N_4O_3ClFS$: C, 56.11; H, 3.42; N, 11.90; Cl, 6.81; S, 7.53. Found: C, 55.95; H, 3.50; N, 11.85; Cl, 6.82; S, 7.50.

The following compounds in Table IV were prepared according to procedures similar to that exemplified in Examples 96–98, with the substitution of the appropriate starting material.

TABLE IV

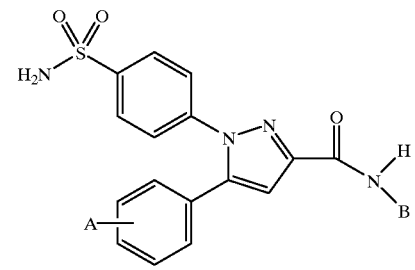

| Ex. | A | B | M.P. ° C. | Analytical |
|---|---|---|---|---|
| 99 | 4-Br | H | 143–145 | MH+ = 421 |
| 100 | 4-F | phenyl- | 233–236 | MH+ = 436 |
| 101 | 4-NO₂ | H | 278–281 | MH+ = 387 |
| 102 | 4-F | 4-CH₃O-phenyl- | 209–211 | MH+ = 466 |
| 103 | 4-F | 4-CH₃-phenyl- | 222–225 | MH+ = 451 |
| 104 | 4-F | cyclohexyl- | 224–227 | MH+ = 442 |
| 105 | 4-F | 3-F-phenyl- | 227 | MH+ = 454 |
| 106 | 4-Cl | 3-F-phenyl- | 174–176 (dec) | MH+ = 471 |
| 107 | H | H | ND | MH+ = 343 |
| 108 | 4-OCH₃, 3-Cl | H | ND | MH+ = 408 |
| 109 | 4-SCH₃ | H | 115 (dec) | HRMS: 389.0743 |
| 110 | 4-OCH₃ | H | 115–140 | Calc. C, 54.83; H, 4.33; N; 15.04 Obs. C, 54.76; H, 4.34; N, 14.98 |
| 111 | 4-CH₃ | H | 139–140 | HRMS H₂O: 356.0939 |
| 112 | 4-OCH₃ | —CH₃ | 209 | MH+ = 387 |
| 113 | 4-Cl | glycine benzyl ester | 136 | MH+ = 525 |
| 114 | 4-Cl | glycine | 124–130 | MH+ = 435 |
| 115 | 4-OCH₃, 3-Br | H | ND | M + Li = 457/459 |
| 116 | 4-OCH₃, 3,5-di-Cl | H | 185 (dec) | HRMS: 440.0113 |

EXAMPLE 117

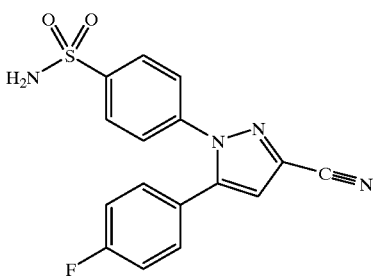

4-[3-Cyano-5-(4-fluorophenyl-1H-pyrazol-1-yl]benzenesulfonamide

A dry 100 ml three-neck flask, equipped with a reflux condenser, thermometer, pressure-equalizing addition funnel and provisions for magnetic stirring was charged with anhydrous DMF (20 mL) and cooled to 0° C. Oxalyl chloride (0.530 mL, 6.105 mmol) was added over twenty seconds, causing a 5° C. exotherm. The white precipitate formed dissolved as the reaction cooled to 0° C. The reaction was held at 0° C. for ten minutes, then a solution of [1-(4-aminosulfonylphenyl)-5-(4-fluorophenyl)-1H-pyrazol-3-yl]carboxamide (Example 97) in anhydrous DMF was added to the vigorously stirring solution over approximately two minutes. After fifteen minutes, pyridine (1.0 mL, 12.21 mmol) was added to quench the reaction. The mixture was poured into dilute hydrochloric acid (1N, 100 mL) and extracted with ethyl acetate (2×75 mL). The combined organic solution was washed with 1N HCl (2×100 mL) and with 50% saturated NaCl (3×100 mL). The organic solution was dried over magnesium sulfate, filtered and concentrated in vacuo to a crude oil. The oil was applied to a column of silica gel and eluted with ethyl acetate and hexane (40% ethyl acetate) to obtain, upon concentration of the appropriate fractions, 0.66 g (69%) of 4-[3-cyano-5-(4-fluorophenyl-1H-pyrazol-1-yl]benzenesulfonamide as a white solid: mp 184–185° C.; $^1$H NMR (CDCl$_3$/300 MHz) 7.94 (d, J=8.86 Hz, 2H), 7.44 (d, J=8.86 Hz, 2H), 7.23–7.07 (m, 4H), 6.87 (s, 1H), 4.88 (brs, 2H); $^{19}$F NMR (CDCl$_3$/282.2 MHz) −109.90(m). Mass spectrum, MH+=343. Anal. Calc'd for C$_{16}$H$_{11}$N$_4$O$_2$FS: C, 56.14; H, 3.24; N, 16.37; S, 9.36. Found: C, 56.19; H, 3.16; N, 16.39; S, 9.41.

The following compounds in Table V were prepared according to procedures similar to that exemplified in Example 117, with the substitution of the appropriate starting material.

TABLE V

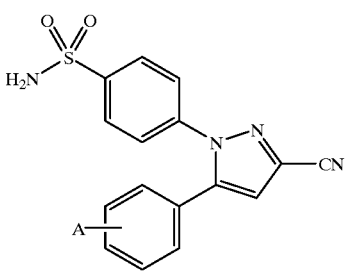

| Ex. | A | M.P. (° C.) | Anal. |
|---|---|---|---|
| 118 | 4-Br | 156–157 | HRMS: 401.9833 |
| 119 | 4-Cl | 142–143 | |
| 120 | 4-OCH$_3$ | ND | HRMS: 354.0774 |
| 121 | 4-CH$_3$ | 90–95 | HRMS: 338.0849 |
| 122 | 4-SCH$_3$ | 192–193 | |
| 123 | 4-OCH$_3$, 3-Cl | 179 | MH+ = 389 |
| 124 | 4-OCH$_3$, 3,5-di-Cl | 121–125 | HRMS: 422.0051 |
| 125 | 4-OCH$_3$, 3-Br | 213 | MH+ = 433 |
| 126 | 4-NO$_2$ | 230–232 | MH+ = 370 |
| 127 | H | ND | MH+ = 325 |

EXAMPLE 128

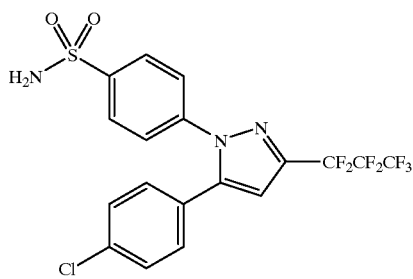

4-[5-(4-Chlorophenyl)-3-(heptafluoropropyl)-1H-pyrazol-1-yl]benzenesulfonamide

Step 1: Preparation of 4,4,5,5,6,6,6-heptafluoro-1-[4-(chloro)phenyl]hexane-1,3-dione.

Ethyl heptafluorobutyrate (5.23 g, 21.6 mmol) was placed in a 100 mL round bottom flask, and dissolved in ether (20 mL). To the stirred solution was added 25% sodium methoxide (4.85 g, 22.4 mmol) followed by 4-chloroacetophenone (3.04 g, 19.7 mmol). The reaction was stirred at room temperature overnight (15.9 hours) and treated with 3N HCl (17 mL). The organic layer was collected, washed with brine, dried over MgSO$_4$, concentrated in vacuo, and recrystallized from iso-octane to give the diketone as a white solid (4.27 g, 62%): mp 27–30° C.; $^1$H NMR (CDCl$_3$) 300 MHz 15.20 (br s, 1H), 7.89 (d, J=8.7 Hz, 2H), 7.51 (d, J=8.7 Hz, 2H), 6.58 (S, 1H); $^{19}$F NMR (CDCl$_3$) 300 MHz: −80.94 (t), −121.01 (t), −127.17 (s); M+H 351.

Step 2: Preparation of 4-[5-(4-chlorophenyl)-3-(heptafluoropropyl)-1H-pyrazol-1-yl]benzenesulfonamide The 4-sulfonamidophenylhydrazine hydrochloride (290 mg, 1.30 mmol) was added to a stirred solution of the diketone from Step 1 (400 mg, 1.14 mmol) in ethanol (5 mL). The reaction was heated to reflux and stirred overnight (23.8 hours). The ethanol was removed in vacuo, and the residue was dissolved in ethyl acetate, washed with water and brine, dried over MgSO$_4$, and concentrated in vacuo to give a white solid which was passed through a column of silica gel with ethyl acetate/hexane (40%) and recrystallized from ethyl acetate/isooctane to give the pyrazole as a white solid (0.24 g, 42%): mp 168–71° C.; $^1$H NMR (CDCl$_3$) 300 MHz 7.90 (d, J=8.7 Hz, 2H), 7.45 (d, J=8.7 Hz, 2H), 7.34 (d, J=8.5 Hz, 2H), 7.19 (d, J=8.5 Hz, 2H), 6.79 (s, 1 H), 5.20 (br s, 2H); $^{19}$F NMR (CDCl$_3$) 300 MHz: –80.48 (t), –111.54 (t), –127.07 (s).

EXAMPLE 129

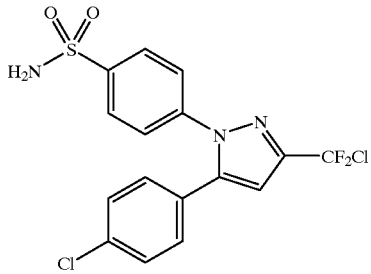

4-[5-(4-Chlorophenyl)-3-(chloro-difluoromethyl)-1H-pyrazol-1-yl]benzenesulfonamide Step 1: Preparation of 4-chloro-4,4-difluoro-1-[4-(chloro)phenyl]-butane-1,3-dione.

Methyl 2-chloro-2,2-difluoroacetate (4.20 g, 29 mmol) was paced in a 100 mL round bottom flask, and dissolved in ether (10 mL). To the stirred solution was added 25% sodium methoxide (6.37 g, 29 mmol) followed by 4'-chloroacetophenone (4.10 g, 26.5 mmol). The reaction was stirred at room temperature overnight (20.4 hours), then poured into a separatory funnel and washed with 3N HCl (15 mL), brine (20 mL), dried over MgSO$_4$, and concentrated in vacuo and recrystallized from iso-octane to give the diketone as a yellow solid (3.78 g, 53%): mp 53–55° C.; $^1$H NMR (CDCl$_3$) 300 MHz 14.80 (br s, 1H), 7.87 (d, J=8.7 Hz, 2H), 7.50 (d, J=8.7 Hz, 2H), 6.49 (S, 1H); $^{19}$F NMR (CDCl$_3$) 300 MHz: –66.03 (s); M+ 267.

Step 2: Preparation of 4-[5-(4-chlorophenyl)-3-(chloro-difluoromethyl)-1H-pyrazol-1-yl]benzenesulfonamide 4-Sulfonamidophenylhydrazine hydrochloride (1.39 g, 6.2 mmol) was added to a stirred solution of the diketone from Step 1 (1.43 g, 5.7 mmol) in ethanol (10 mL). The reaction was heated to reflux and stirred overnight (15.75 hours). The ethanol was removed in vacuo, and the residue was dissolved in ethyl acetate, washed with water and brine, dried over MgSO$_4$, and concentrated in vacuo to give a white solid which was recrystallized from ethyl acetate/isooctane to give the pyrazole as a white solid (0.32 g, 41%): mp 130–33° C.; $^1$H NMR (CDCl$_3$) 300 MHz 7.90 (d, J=8.9 Hz, 2H), 7.47 (d, J=8.7 Hz, 2H), 7.35 (d, J=8.5 Hz, 2H), 7.19 (d, J=8.7 Hz, 2H), 6.76 (s, 1H), 5.13 (br s, 2H); $^{19}$F NMR (CDCl$_3$) 300 MHz: –48.44 (s); M+ 417/419.

EXAMPLE 130

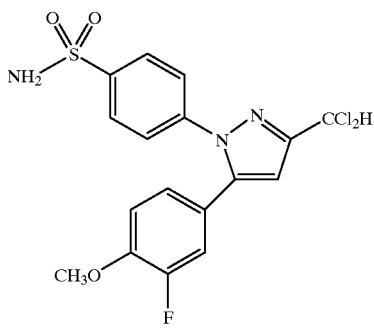

4-[3-(Dichloromethyl)-5-(3-fluoro-4-methoxyphenyl)-1H-pyrazol-1-yl] benzenesulfonamide Step 1. Preparation of 3'-fluoro-4'-methoxyacetophenone.

Aluminum chloride (80.0 g, 0.6 mol) and chloroform (750 mL) were placed in a 2 L three-necked round bottom flask fitted with a mechanical stirred and cooled by means of an ice bath. To the stirred solution was added acetyl chloride (51.0 g, 0.65 mol) dropwise, maintaining the temperature between 5–10° C. The mixture was allowed to stir for 10 minutes. at 5° C. before the dropwise addition at 5–10° C. of 2-fluoroanisole (63.06 g, 0.5 mol). The mixture was stirred at 0–10° C. for 1 hour and poured into ice (1 L). The resultant layers were separated and the aqueous layer was extracted with methylene chloride (2×250 mL). The combined organic layers were washed with water (2×150 mL), dried over magnesium sulfate, and concentrated to 300 mL. Hexanes were added and a white solid (77.2 g, 92%) was crystallized from the mixture: mp 92–94° C.; $^1$H NMR (d$_6$-DMSO) 7.8 (m, 2H), 7.3 (t, J=8.7 Hz, 1H), 3.9 (s, 3H), 2.5 (s, 3H).

Step 2. Preparation of 4,4-dichloro-1-(3-fluoro-4-methoxyphenyl)-butane-1,3-dione.

Methyl dichloroacetate (1.57 g, 11 mmol) was dissolved ether (25 mL). To the stirred solution was added 25% sodium methoxide (2.38 g, 11 mmol) followed by 3'-fluoro-4'-methoxyacetophenone from Step 1 (1.68 g, 10 mmol). After stirring 16 hours 1N HCl (25 mL) was added. The organic layer was collected and washed with water (2×25 mL), dried over magnesium sulfate, filtered, and concentrated. The resulting crude dione was used in the next step without further purification or characterization.

Step 3. Preparation of 4-[3-(dichloromethyl)-5-(3-fluoro-4-methoxyphenyl)-1H-pyrazol-1-yl]benzenesulfonamide.

4,4-Dichloro-1-(3-fluoro-4-methoxyphenyl)-butane-1,3-dione from Step 2 (2.8 g, 10 mmol) was dissolved in ethanol (100 mL). To the stirred mixture was added 4-sulfonamidophenylhydrazine hydrochloride (2.46 g, 11 mmol) and heated to reflux for 16 hours. The mixture was cooled and water was added until crystals slowly appeared. Filtration yielded a light tan solid (2.7 g, 63%): mp 190–193° C.; $^1$H NMR (DMSO-d$_6$) 7.84 (d, J=8.4 Hz, 2H), 7.53 (s, 1H), 7.48 (d, J=8.4Hz, 2H), 7.47 (brs, 2H), 7.3–7.0 (m, 3H), 6.95 (s, 1H), 3.85 (s, 3H). Anal. Calc'd for C$_{17}$H$_{14}$N$_3$SO$_3$FCl$_2$: C, 47.45; H, 3.28; N, 9.76. Found: C, 47.68; H, 3.42; N, 10.04.

EXAMPLE 131

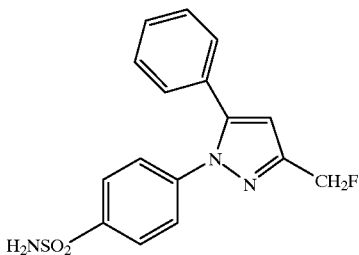

4-[3-Fluoromethyl-5-phenyl-1H-pyrazol-1-yl]
benzenesulfonamide

Step 1: Preparation methyl 4-phenyl-2,4-dioxobutanoate

To a solution of dimethyl oxalate (11.81 g, 100 mmol) in ether (200 mL) is added 24 mL of 25% sodium methoxide in methanol, followed by a solution of acetophenone (12.02 g, 100 mmol) in ether (20 mL) and the mixture stirred overnight at room temperature. The mixture was partitioned between 1N HCl and EtOAc and the organic layer was washed with brine, dried over $MgSO_4$ and concentrated to give 18.4 g of crude butanoate.

Step 2: Preparation of methyl 1-[(4-(aminosulfonyl)phenyl]-5-phenyl-1H-pyrazole 3-carboxylate The ester was prepared from the butanoate in Step 1 using the procedure described in Example 2, Step 2.

Step 3: Preparation 4-[3-hydroxymethyl-5-phenyl-1H-pyrazol-1-yl]benzenesulfonamide To a solution of ester in Step 2 (4.0 g, 10.4 mmol) in 50 mL THF was added $LiAlH_4$ (0.592 g, 15.6 mmol) in portions and the mixture refluxed overnight. The reaction was cooled and quenched with 1N $NaHSO_4$ and extracted with ether (3×). The combined extracts were dried over $MgSO_4$ and concentrated to give 3.5 g crude alcohol. Flash chromatography using 1:1 hexane/EtOAc provided the title compound.

Step 4: Preparation 4-[3-fluoromethyl-5-phenyl-1H-pyrazol-1-yl]benzenesulfonamide To a mixture of the alcohol from Step 3 (212 mg, 0.64 mmol) in dichloromethane (4 mL) was added diethylaminosulfur trifluoride (0.13 mL, 1.0 mmol). The reaction mixture was stirred at room temperature for 3 hours and partitioned between water and dichloromethane. The aqueous solution was extracted with dichloromethane. The organic solution was washed with brine and concentrated. The residue was chromatographed on silica (1:1 hexane:ethyl acetate) to give the desired product (72 mg, 34%): mp 162–163° C.; Anal. calc'd for $C_{16}H_{14}N_3O_2SF$: C, 58.00; H, 4.26; H, 12.68. Found: C, 57.95; H, 4.03; N, 12.58.

The following compounds in Table VI were prepared according to procedures similar to that exemplified in Examples 128–131, with the substitution of the appropriate substituted acetyl and acetate starting materials.

TABLE VI

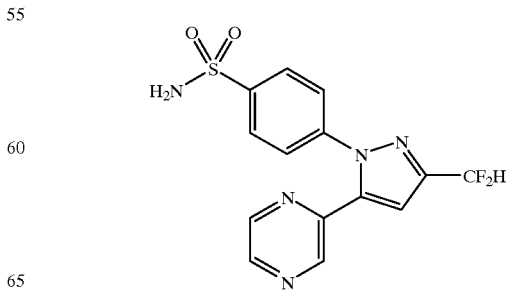

| Ex. | A | $R^2$ | M.P. (° C.) | Anal. |
|---|---|---|---|---|
| 132 | 4-Cl | —$CF_2CF_3$ | 145.5–150 | |
| 133 | 4-Cl | —$CH_2Cl$ | 198–201 | Calc. C, 50.27; H, 3.43; N, 10.99 |
| | | | | Found C, 50.34; H, 3.43; N, 10.96 |
| 134 | 3-F, 4-$OCH_3$ | —$CF_2Cl$ | 120–124 | Calc. C, 47.29; H, 3.04; N, 9.74 |
| | | | | Found C, 47.28; H, 3.37; N, 9.88 |
| 135 | 3-F, 4-$OCH_3$ | —$CBrF_2$ | 120–122 | Calc. C, 42.87; H, 2.75; N, 8.82 |
| | | | | Found C, 42.99; H, 3.81; N, 9.92 |
| 136 | 3-Cl, 4-$OCH_3$ | —$CH_2Cl$ | ND | Calc. C, 49.53; H, 2.84; N, 8.66 |
| | | | | Found C, 50.03; H, 3.81; N, 9.92 |

EXAMPLE 137

4-[5-(2-Pyrazinyl)-3-(difluoromethyl)-1H-pyrazol-1-yl]benzenesulfonamide

Step 1: Preparation of 4,4-difluoro-1-(2-pyrazinyl)-butane-1,3-dione.

Ethyl difluoroacetate (2.23 g, 18 mmol) was placed in a 100 mL round bottom flask and dissolved in ether (10 mL). To the stirred solution was added 25% sodium methoxide (4.68 g, 22 mmol) followed by acetylpyrazine (2.00 g, 16 mmol). After two hours stirring at room temperature, a precipitate formed and THF (10 mL) was added to the reaction. The reaction was stirred an additional 25.9 hours, then treated with 3N HCl (10 mL). The organic layer was collected, washed with brine (20 mL), dried over $MgSO_4$, and concentrated in vacuo and recrystallized from methylene chloride/iso-octane to give the diketone as a brown solid (2.23 g, 68%); mp 103–110° C.; $^1$H NMR ($CDCl_3$) 300 MHz 14.00 (br s, 1H), 9.31 (d, J=1.4 Hz, 1H), 8.76 (d, J=2.4 Hz, 1H), 8.68 (dd, J=1.4 Hz 2.4 Hz, 1H), 7.20 (s, 1H), 6.03 (t, J=54.0 Hz, 1H); $^{19}$F NMR ($CDCl_3$) 300 MHz: −127.16 (d); M+ 200.

Step 2: Preparation of 4-[5-(2-pyrazinyl)-3-(difluoromethyl)-1H-pyrazol-1-yl]benzenesulfonamide 4-Sulfonamidophenylhydrazine hydrochloride (0.37 g, 1.65 mmol) was added to a stirred suspension of the diketone from Step 1 (0.30 g, 1.50 mmol) in ethanol (10 mL). The reaction was heated to reflux and stirred for 5.3 hours. The ethanol was removed in vacuo, and the residue was dissolved in ethyl acetate, washed with water (20 mL), brine (20 mL), dried over $MgSO_4$, and concentrated in vacuo to give a brown solid (0.36 g) which was recrystallized from ethyl acetate/ethanol/isooctane to give the pyrazole as a brown solid (0.20 g, 38%): mp 191–94° C.; $^1$H NMR (acetone $d_6$) 300 MHz 8.94(d, J=1.4 Hz, 1H), 8.62 (d, J=2.4 Hz, 1H), 8.52 (dd, J=1.4 Hz 2.4 Hz, 1H), 7.95 (d, J=8.7 Hz, 2H), 7.61 (d, J=8.7 Hz, 2H), 7.30 (s, 1H), 7.02 (t, J=54.6 Hz, 1H), 6.73 (br s, 2 H); $^{19}$F NMR (acetone $d_6$) 300 MHz: −113.67 (d); M+ 351.

EXAMPLE 138

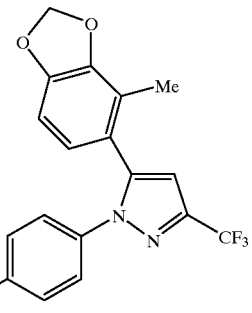

4-[5-(4-methyl-1,3-benzodioxol-5-yl)-3-(trifluoromethyl)-1H-pyrazol-1-yl]benzenesulfonamide Step 1: Preparation of 4-methyl-1,3-benzodioxole 11.6 g Adogen 464 and 7 mL of dibromomethane were refluxed in 50 mL of $H_2O$ for 0.5 hours under argon. 3-Methylcatechol (8.89 g, 71.6 mmol) was added over 2 hours and the mixture refluxed for an additional 1 hour. Distillation of the product from the reaction mixture afforded the title compound as a yellow oil: HRMS m/e 136.0524 (calc'd for $C_8H_8O_2$, 136.0524).

Step 2: Preparation of 5-acetyl-4-methyl-1,3-benzodioxole (A) and 6-acetyl-4-methyl-1,3-benzodioxole (B)

13.8 g of polyphosphoric acid and 5 mL of acetic anhydride were heated to 45° C. under a drying tube of $CaSO_4$ until liquified. The product from Step 1 was added and the reaction was stirred at 45° C. for 4.5 hours. The reaction was cooled to room temperature and quenched with 150 mL of ice water. The aqueous phase was washed with ethyl acetate (4×50 mL). The combined organic extracts were dried over $MgSO_4$ and filtered to give the crude product as a red oil. The oil was chromatographed on silica gel eluting with 10% ethyl acetate/90% hexane to afford two products: A: Anal. calcd for $C_{10}H_{10}O_3$: C, 67.07; H, 5.66. Found: C, 67.41; H, 5.75, and B: MS, M+ 178.

Steps 3 and 4: 4-[5-(4-methyl-1,3-benzodioxol-5-yl)-3-(trifluoromethyl)-1H-pyrazol-1-yl]benzensulfonamide The title compound was prepared from product A using the procedures described in Example 2, Steps 1 and 2: White solid: Anal. calcd for $C_{18}H_{14}N_3O_4SF_3$: C, 50.82; H, 3.22; N, 9.88. Found: C, 50.71; H, 3.34; N, 9.55.

The following compounds in Table VII were prepared according to procedures similar to that exemplified in Examples 137–138, with the substitution of the appropriate starting material.

TABLE VII

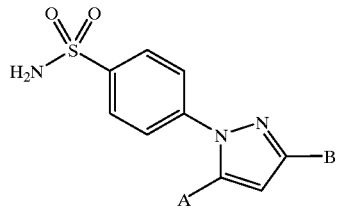

| Ex. | A | B | M.P. (° C.) | Anal. |
|---|---|---|---|---|
| 139 | 5-bromo-2-thienyl | $CF_2H$ | 168–169 | M + Li 440/442 |
| 140 | 2-thienyl | $CF_2H$ | 190–191 | M + Li 367 |
| 141 | 5-chloro-2-thienyl | $CF_2H$ | 168–170 | M + 389/391 |
| 142 | 1-cyclohexenyl | $CF_2H$ | 160–161 | M + 353. |

TABLE VII-continued

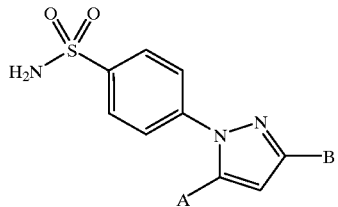

| Ex. | A | B | M.P. (° C.) | Anal. |
|---|---|---|---|---|
| 143 | 1,4-benzodioxan | CF₂H | 115–119 | Calc. C, 53.06; H, 3.71; N, 10.32 |
|  |  |  |  | Obs. C, 52.40; H, 3.98; N, 9.96 |
| 144 | 4-methylcyclohex-3-ene-1-yl | CF₂H | 164–168 | HRMS: 367.1194 |
| 145 | 2-methylcyclopenten-1-yl | CF₂H | 165–166 | HRMS: 353.1033 |
| 146 | 2,5-dimethyl-3-thienyl | CF₂H | 125–127 | Calc. C, 50.12; H, 3.94; N, 10.96 |
|  |  |  |  | Obs. C, 50.21; H, 3.92; N, 11.00 |
| 147 | 2,5-dimethyl-3-furyl | CF₂H | 139–142 | Calc. C, 52.31; H, 4.12; N, 11.44 |
|  |  |  |  | Obs. C, 52.07; H, 4.16; N, 11.37 |
| 148 | 5-methyl-2-furyl | CF₂H | 177–179 | Calc C, 50.99; H, 3.71; N, 11.89 |
|  |  |  |  | Obs. C, 51.08; H, 3.68; N, 11.95 |
| 149 | 4-bromo-4-methylcyclohex-1-yl | CF₂H | 175–178 (dec) | HRMS: 448.0520 |
| 150 | 4-methylcyclohex-1-yl | CF₂H | 190–192 | HRMS: 369.1341 |
| 151 | 4-chloro-4-methylcyclohex-1-yl | CF₂H | 197–199 | HRMS: 403.0958 |
| 152 | 3,4-dibromo-4-methylcyclohex-1-yl | CF₂H | 172–173 |  |
| 153 | 2-methoxycyclohex-1-yl | CF₂H | 177–179 | HRMS: 386.1357 |
| 154 | 2-benzofuryl | CF₂H | 215–217 | Calc C, 55.52; H, 3.37; N, 10.79 |
|  |  |  |  | Obs. C, 55.52; H, 3.32; N, 10.85 |
| 155 | 2,5-dichloro-3-thien-yl | CF₂H | 154–156 | Calc. C, 39.63; H, 2.14; N, 9.90 |
|  |  |  |  | Obs. C, 39.63; H, 2.13; N, 9.89 |
| 156 | 2-benzofuryl | CF₃ | 227–228 | Calc. C, 53.07; H, 2.97; N, 10.31 |
|  |  |  |  | Obs. C, 53.02; H, 2.96; N, 10.39 |
| 157 | 5-chloro-2-thienyl | CF₃ | 161–165 | HRMS: 406.9784 |
| 158 | 5-bromo-2-thienyl | CF₃ | ND | Calc: C, 37.18; H, 2.01; N, 9.29; |
|  |  |  |  | Br, 17.67 |
|  |  |  |  | Found: C, 37.25; H, 1.93; N, 9.45; |
|  |  |  |  | Br, 17.40 |
| 159 | 5-indanyl | CF₃ | 118–120 | Calc: C, 56.01; H, 3.96; N, 10.31 |
|  |  |  |  | Found: C, 56.02; H, 4.06; N, 10.22 |
| 160 | 5-methylthien-2-yl | CF₃ | 188–190 | Calc. C, 46.51; H, 3.12; N, 10.85 |
|  |  |  |  | Found: C, 46.17; H, 3.10; N, 10.75 |
| 161 | 2,3-dihydrobenzofuryl | CF₃ | 152–153 | Calc. C, 52.81; H, 3.45; N, 10.26 |
|  |  |  |  | Found: C, 52.67; H, 3.78; N, 10.13 |
| 162 | 1-cyclohexenyl | CF₃ | 135–138 | HRMS: 371.0918 |
| 163 | 6-tetrahydronaphthyl | CF₃ | 143–145 | Calc. C, 57.00; H, 4.31; N, 9.97 |
|  |  |  |  | Found: C, 56.72; H, 4.27; N, 9.90 |
| 164 | 3-benzothienyl | CF₃ | 164–165 | Calc. C, 51.06; H, 2.86; N, 9.92 |
|  |  |  |  | Obs. C, 50.96; H, 2.73; N, 9.78 |
| 165 | 3,4-dihydrobenzopyranyl | CF₃ | ND | HRMS: 423.0855 |
| 166 | styryl | CF₃ | 166–167 | Calc. C, 54.96; H, 3.59; N, 10.68 |
|  |  |  |  | Obs. C, 54.77; H, 3.59; N, 10.47 |
| 167 | 4-methyl-1,3-benzodioxol-6-yl | CF₃ | ND | Calc. C, 50.82; H, 3.22; N, 9.88 |
|  |  |  |  | Obs. C, 50.64; H, 3.35; N, 9.72 |
| 168 | 3-pyridyl | CF₃ | 202–204 | Calc. C, 48.91; H, 3.01; N, 15.21 |
|  |  |  |  | Obs. C, 48.97; H, 3.16; N, 14.96 |
| 169 | 3,4-dihydrobenzothiopyranyl | CF₃ | ND | Calc. C, 51.95; H, 3.67; N, 9.56 |
|  |  |  |  | Obs. C, 51.98; H, 3.78; N, 9.48 |

EXAMPLE 170

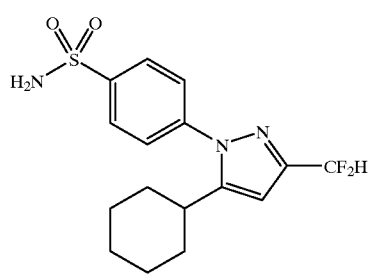

4-[5-(1-Cyclohexyl)-3-(difluoromethyl)-1H-pyrazol-1-yl]benzenesulfonamide

4-[5-(1-Cyclohexenyl)-3-(difluoromethyl)-1H-pyrazol-1-yl]benzenesulfonamide (Example 142) (0.31 g, 0.88 mmol) was dissolved in ethanol (15 mL), 10% palladium on charcoal was added, and the suspension was stirred at room temperature under hydrogen (36 psi) for 18.25 hours. The reaction was filtered through celite, and the ethanol removed in vacuo to give a white solid, which was recrystallized from methylene chloride/isooctane (0.31 g, 99%): mp 199–203° C.; $^1$H NMR (acetone-d$_6$) 300 MHz 8.05 (d, J=8.7 Hz, 2H), 7.60 (d, J=8.5 Hz, 2H), 6.69 (t, J=55.0 Hz 1 H), 6.47 (s, 1H), 5.02 (br s, 2H), 2.67 (m, 1H), 171–1.88(m, 5H), 1.24–1.43 (m, 5H); $^{19}$F NMR (acetone-d$_6$) 300 MHz: −112.86 (d).

EXAMPLE 171

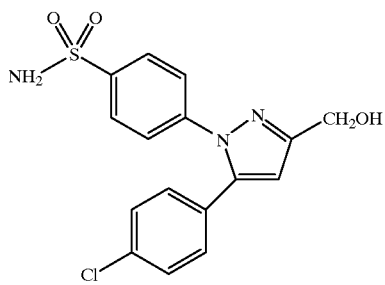

4-[5-(4-Chlorophenyl)-3-hydroxymethyl-1H-pyrazol-1-yl]benzenesulfonamide

4-[4-(Aminosulfonyl)phenyl-5-(4-chlorophenyl)-1H-pyrazole-3-carboxylic acid (Example 83) (3.8 g, 10 mmol) and tetrahydrofuran (100 mL) were stirred at room temperature during the dropwise addition of 1.0 M borane-tetrahydrofuran complex (30 mL, 30 mmol). The mixture was heated to reflux for 16 hours. The solution was cooled and methanol was added dropwise until gas evolution ceased. Ethyl acetate (100 mL) was added and the mixture was washed successively with 1 N hydrochloric acid, brine, sat. aq. sodium bicarbonate solution, and water, dried over magnesium sulfate, filtered an concentrated. The resultant product was recrystallized from ethanol:water to yield 2.6 g (71%) of a white solid: mp 192–194° C.; $^1$H NMR ($d_6$-DMSO/300 MHz) 7.81 (d, J=8.7 Hz, 2H), 7.46 (d, J=8.4 Hz, 2H), 7.42 (brs, 2H), 7.40 (d, J=8.7 Hz, 2H), 7.26 (d, J=8.4 Hz, 2H), 6.63 (s, 1H), 5.35 (t, J=8.0 Hz, 1H), 4.50 (d, J=8.0 Hz, 2H). Anal. Calc'd for $C_{16}H_{14}N_6SO_2Cl$: C, 52.82; H, 3.88; N, 11.55. Found: C, 52.91; H, 3.88; N, 11.50.

EXAMPLE 172

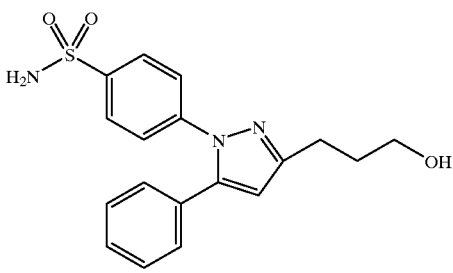

4-[5-Phenyl-3-(3-hydroxypropyl)-1H-pyrazol-1-yl]benzenesulfonamide

A 60% dispersion of sodium hydride in mineral oil (4.0 g, 100 mmol) was twice washed with hexane (100 mL each) and dried under a stream of nitrogen. Ether (300 mL) was added followed by dropwise addition of ethanol (0.25 mL) and γ-butyrolactone (4.0 mL, 52 mmol). The mixture was cooled to 10° C. and acetophenone (5.8 mL, 50 mmol) in ether (40 mL) was added dropwise over 1 hour. The mixture was warmed to 25° C. and stirred overnight. The mixture was cooled to 0° C. and quenched with ethanol (5 mL) followed by 10% aqueous ammonium sulfate (100 mL). The organic solution was separated, dried over $Na_2SO_4$ and concentrated. The residue was chromatographed on silica gel with 1:1 hexane/ethyl acetate to give the desired diketone (3.4 g) as an oil. Pyridine (0.34 mL, 4.2 mmol) and the diketone (700 mg, 3.4 mmol) in methanol (3 mL) were added to a slurry of 4-sulfonamidophenylhydrazine-HCl (750 mg, 3.4 mmol) in methanol (8 mL). The mixture was stirred at 25° C. overnight and concentrated in vacuo. The residue was dissolved in methylene chloride and the solution washed with 1N HCl. The organic solution was separated, dried and concentrated. The residue was chromatographed on silica gel using ethyl acetate to give the desired pyrazole (435 mg) as a solid: Anal. calc'd for $C_{18}H_{19}N_3O_3S$: C, 60.49; H, 5.36; N, 11.75. Found: C, 60.22; H, 5.63; N, 11.54.

EXAMPLE 173

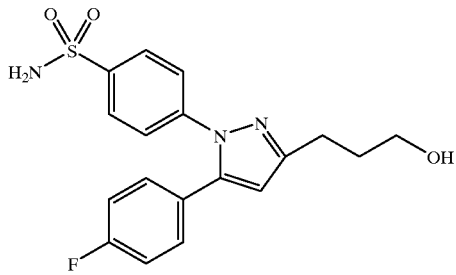

4-[5-(4-Fluorophenyl)-3-(3-hydroxypropyl)-1H-pyrazol-1-yl]benzenesulfonamide Following the procedure of Example 172, but substituting 4-fluoroacetophenone for acetophenone afforded 4-[5-(4-fluorophenyl)-3-(3-hydroxypropyl)-1H-pyrazol-1-yl]benzenesulfonamide. Anal. calc'd for $C_{18}H_{18}N_3O_3SF.0.25$ $H_2O$: C, 56.90; H, 4.91; N, 11.05. Found: C, 56.80; H, 4.67; N, 11.02.

EXAMPLE 174

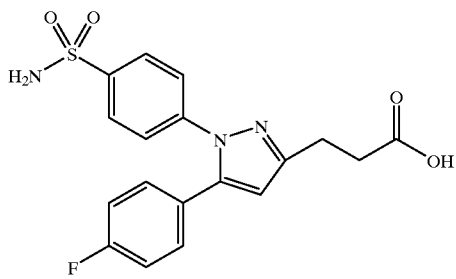

4-[4-(Aminosulfonyl)phenyl]-5-(4-fluorophenyl)-1H-pyrazole]-3-propanoic acid Jones reagent (0.64 mL of a 2.67 M solution) was added dropwise to a solution of 4-[5-(4-fluorophenyl)-3-(3-hydroxypropyl)-1H-pyrazol-1-yl]benzenesulfonamide from Example 173 (295 mg, 0.78 mmol) in acetone (8 mL). The mixture was stirred at 25° C. for 2 hours. The solution was filtered and the filtrate concentrated in vacuo. The residue was dissolved in ethyl acetate and washed with water (3x). The organic solution was dried over $MgSO_4$ and concentrated. The residual oil was crystallized from ether/hexane to give the desired acid (149 mg): mp 180–182° C.; Anal. calc'd for $C_{18}H_{16}N_3O_4SF$: C, 55.52; H, 4.14; N, 10.79. Found: C, 55.47; H, 4.22; N, 10.50.

EXAMPLE 175

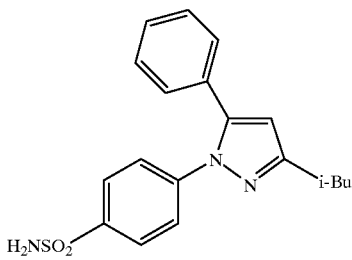

4-(3-Isobutyl-5-phenyl-1H-pyrazol-1-yl)
benzenesulfonamide

Step 1: Preparation of 2,3-epoxy-5-methyl-1-phenyl-3-hexanone

To a solution of 5-methyl-1-phenyl-1-hexen-3-one (2.0 g, 10.6 mmol) in 15 mL EtOH and 5 mL acetone was added a mixture of 30% hydrogen peroxide (2 mL) and 4 N NaOH (1.5 mL) dropwise and the mixture stirred at 25° C. for 1–3 hours. Water (50 mL) was added and the precipitate filtered and dried at 40° C. in vacuo to provide 1.9 g of the epoxide as a white solid: Anal. calc'd for $C_{13}H_{16}O_2.0.1\ H_2O$: C, 75.77; H, 7.92. Found: C, 75.47; H, 7.56.

Step 2: Preparation of 4-(3-isobutyl-5-phenyl-1H-pyrazol-1-yl)benzenesulfonamide The epoxide prepared above in Step 1 (1.26 g, 6.11 mmol) and 4-sulfonamidophenylhydrazine hydrochloride (1.38 g, 6.17 mmol) were stirred in 20 mL EtOH with AcOH (0.5 mL) and the mixture refluxed for 3 hours, cooled and quenched with 50 mL $H_2O$. The aqueous layer was extracted with ethyl acetate (3×50 mL), the combined extracts were dried over $MgSO_4$ and concentrated. Flash chromatography using 70:30 hexane/ethyl acetate provided the title compound (0.41 g, 19%) as a white solid: Calc'd for $C_{19}H_{21}N_3O_2S$: C, 64.20; H, 5.96; N, 11.82. Found: C, 64.31; H, 6.29; N, 11.73.

EXAMPLE 176

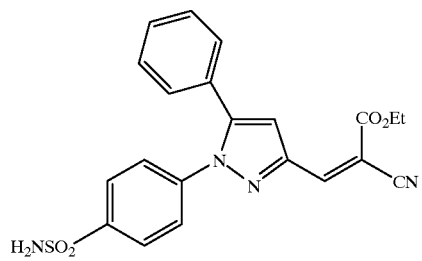

Ethyl 3-[1-[4-(aminosulfonyl)phenyl]-5-phenyl-1H-pyrazol-3-yl]-2-cyano-2-propenoate Step 1: Preparation of 4-[3-formyl-5-phenyl-1H-pyrazol-1-yl]benzenesulfonamide To a solution of the alcohol prepared in Example 131, Step 3 (1.1 g, 3.3 mmol) in ethyl acetate (20 mL) was added $MnO_2$ (5 g, 60 mmol) and the mixture stirred at room temperature overnight. The mixture was filtered through Celite and the solution was concentrated to provide the crude aldehyde.

Step 2: Preparation of ethyl 3-[1-[4-(aminosulfonyl)phenyl]-5-phenyl-1H-pyrazol-3-yl]-2-cyano-2-propenoate To a solution of the aldehyde from Step 1 (1.2 g, 3.6 mmol) in benzene (18 mL) was added ethyl cyanoacetate (0.38 mL, 3.6 mmol), ammonium acetate (50 mg, 0.7 mmol) and glacial acetic acid (0.17 mL, 2.8 mmol). The solution was heated at reflux for 18 hours, cooled, and partitioned between water and ethyl acetate. The organic solution was washed with a saturated aqueous sodium bicarbonate solution, water and brine. The organic solution was dried and concentrated. The residue was chromatographed on silica (40% hexane in ethyl acetate) to give the desired product (1.0 g, 66%): Anal. calc'd for $C_{21}H_{18}N_4O_4S$: C, 59.82; H, 4.30; N, 13.22. Found: C, 59.70; H, 4.29; N, 13.26.

EXAMPLE 177

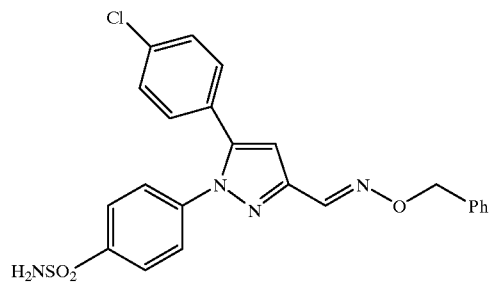

4-[5-(4-Chlorophenyl)-3-[[(phenylmethoxy)imino]methyl]-1H-pyrazol-1-yl]benzenesulfonamide To a suspension of 220 mg (0.58 mmol) 4-[5-(4-chlorophenyl)-3-formyl-1H-pyrazol-1-yl]benzenesulfonamide (prepared as described in Example 176, Step 1) in dichloromethane (3 mL) was added pyridine (0.12 mL, 1.3 mmol) and O-benzylhyroxylamine hydrochloride (110 mg, 0.68 mmol) and the reaction stirred at room temperature for 18 hours. The mixture was partitioned between pH 7 buffer and dichloromethane and the organic layer was washed with water, dried and concentrated. Flash chromatography on silica gel (2:1 hexane/EtOAc) provided the title compound (151 mg, 56%): mp 158–159° C.; Anal. calc'd for $C_{23}H_{19}N_4O_3SCl.0.25\ H_2O$: C, 58.59; H, 4.17; N, 11.88. Found: C, 58.43; H, 4.03; N, 11.85.

The following compounds in Table VIII were prepared according to procedures similar to that exemplified in Examples 171–177, with the substitution of the appropriate starting material.

TABLE VIII

[Structure: pyrazole core with 4-sulfamoylphenyl at N1, aryl (A) at position 5, R² at position 3]

| Ex. | A | R² | M.P. (° C.) | Anal. |
|---|---|---|---|---|
| 178 | H | —CH₂OH | 183–184 | HRMS: 329.0845 |
| 179 | 4-OCH₃ | —CH₂OH | 140–142 | Calc. C, 56.81; H, 4.77; N, 11.69<br>Found: C, 56.92; H, 4.76; N, 11.64 |
| 180 | 3,5-di-Cl, 4-OCH₃ | —CH₂OH | 191–193 | HRMS 427.0199 |
| 181 | 3-Cl, 4-OCH₃ | —CH₂OH | ND | Calc. C, 51.84; H, 4.09; N, 10.67<br>Cl, 9.00; S, 8.14<br>Found: C, 51.77; H, 4.02; N, 10.73;<br>Cl, 9.11; S, 8.03 |
| 182 | 4-CH₃ | —C(CH₃)₂OH | 178–179 | |
| 183 | 4-Cl | —(CH₂)₂CO₂H | 156–159 | |
| 184 | 4-Cl | —CH₂CONH₂ | 198–200 | |
| 185 | H | —CH₃ | ND | Calc. C, 60.46; H, 5.07; N, 13.21<br>Found: C, 60.48; H, 4.95; N, 13.19 |
| 186 | 4-Cl | —CH₂CN | 212–214 | Calc. C, 54.77; H, 3.51 N, 15.03<br>Found: C, 54.94; H, 3.61; N, 14.88 |

EXAMPLE 187

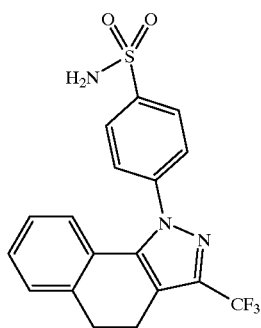

4-[4,5-Dihydro-3-(trifluoromethyl)-1H-benz[g]
indazol-1-yl]benzenesulfonamide

Step 1: Preparation of 2-trifluoroacetyl-1-tetralone.

A 250 mL one necked round bottomed flask equipped with a reflux condenser, nitrogen inlet and provisions for magnetic stirring was charged with ethyl trifluoroacetate (28.4 g, 0.2 mol) and 75 mL of ether. To this solution was added 48 mL of 25% sodium methoxide in methanol (0.21 mol). A solution of 1-tetralone (29.2 g, 0.2 mol) in 50 mL of ether was added over about 5 minutes. The reaction mixture was stirred at room temperature for 14 hours and was diluted with 100 mL of 3N HCl. The phases were separated and the organic layer was washed with 3N HCl, and with brine, dried over anhydrous MgSO₄, filtered and concentrated in vacuo. The residue was taken up in 70 mL of boiling ethanol/water and cooled to room temperature, whereupon crystals of 2-trifluoroacetyl-1-tetralone formed which were isolated by filtration and air dried to give pure compound (32 g, 81%): mp 48–49° C.; ¹H NMR CDCl₃ δ 2.8 (m, 2H), 2.9 (m, 2H), 7.2 (d, j=3.0 Hz, 1H), 7.36 (m, 1H), 7.50 (m, 1H), 7.98 (m, 1H); ¹⁹F NMR CDCl₃ δ −72.0. EI GC-MS M+=242.

Step 2: Preparation of 4-[4,5-dihydro-3-(trifluoromethyl)-1H-benz[g]indazol-1-yl]benzenesulfonamide.

A 100 mL one necked round bottomed flask equipped with reflux condenser, nitrogen inlet and provisions for magnetic stirring was charged with 2-trifluoroacetyl-1-tetralone from Step 1 (1.21 g, 5.0 mmol), 4-sulfonamidophenylhydrazine hydrochloride (1.12 g, 5.0 mmol) and 25 mL of absolute ethanol. The solution was warmed to reflux for 15 hours and concentrated in vacuo. The residue was dissolved in ethyl acetate, washed with water, and with brine, dried over anhydrous MgSO₄, filtered and concentrated in vacuo. The residue was recrystallized from a mixture of ethyl acetate and isooctane to give 1.40 g, 71% of pure product: mp 257–258° C.; ¹H NMR (CDCl₃/CD₃OD, 4:1) δ 2.7 (m, 2H), 2.9 (m, 2H), 6.6 (m, 1H), 6.9 (m, 1H), 7.1 (m, 1H), 7.16 (m, 1H), 7.53 (m, 2H), 7.92 (m, 2H); ¹⁹F NMR (CDCl₃) δ −62.5. FAB-MS M+H=394.

EXAMPLE 188

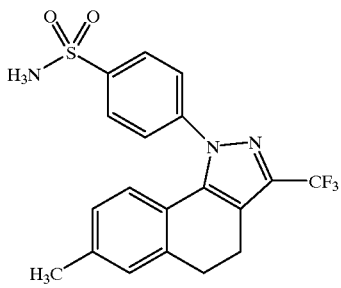

4-[4,5-Dihydro-7-methyl-3-(trifluoromethyl)-1H-
benz[g]indazol-1-yl]benzenesulfonamide Step 1. Preparation of 6-methyl-2-(trifluoroacetyl)tetralone.

Ethyl trifluoroacetate (5.33 g, 37.5 mmol) was dissolved in ether (50 mL) and treated with a sodium methoxide

81 solution (25% in methanol, 9.92 g, 45.9 mmol) followed by 6-methyltetralone (5.94 g, 37.1 mmol). The reaction was stirred at room temperature for 6.1 hours then treated with 3N HCl (20 mL). The organic layer was collected, washed with brine, dried over MgSO$_4$, and concentrated in vacuo to give a brown oil (8.09 g) that was used in the next step without further purification.

Step 2. Preparation of 4-[4,5-dihydro-7-methyl-3-(trifluoromethyl)-1H-benz[g]indazol-1-yl]benzenesulfonamide.

4-Sulfonamidophenylhydrazine hydrochloride (1.80 g, 8.0 mmol) was added to a stirred solution of the diketone from Step 1 (1.86 g, 7.3 mmol) in ethanol (10 mL). The reaction was heated to reflux and stirred for 14.8 hours. The reaction mixture was cooled and filtered. The filtrate was concentrated in vacuo, dissolved in ethyl acetate, washed with water and with brine, dried over MgSO$_4$ and reconcentrated in vacuo to give the pyrazole as a brown solid (1.90 g, 64%):

mp 215–218° C. $^1$H NMR (acetone-d$_6$) 300 MHz 8.10 (d, 2H), 7.80 (d, 2H), 7.24(s, 1H), 6.92 (d, 1H), 6.79 (br s, 2H), 6.88 (d,1H), 3.02 (m, 2H), 2.85 (m, 2H), 2.30 (s, 3H). $^{19}$F NMR (acetone-d$_6$) 282 MHz −62.46 (s). High resolution mass spectrum Calc'd. for C$_{19}$H$_{17}$F$_3$N$_3$O$_2$S: 408.0994. Found: 408.0989.

The following compounds in Table IX were prepared according to procedures similar to that exemplified in Examples 187–188, with the substitution of the appropriate ester.

TABLE IX

| Ex. | R$^2$ | R$^6$ | M.P. (° C.) | Anal. |
|---|---|---|---|---|
| 189 | —CHF$_2$ | 6-OCH$_3$ | 275–277 | HRMS: 405.0961 |
| 190 | —CHF$_2$ | 7-CH$_3$ | 240–241 | HRMS: 390.1122 |
| 191 | —CF$_3$ | 6,8-CH$_3$ | 284–288 | HRMS: 422.1089 |
| 192 | —CF$_3$ | 7-OCH$_3$ | 277–278 | HRMS: 423.0838 |
| 193 | —CF$_3$ | 7,8-OCH$_3$ | 269–275 | HRMS: 453.1011 |
| 194 | —CHF$_2$ | 7-OCH$_3$ | 256–257 | |
| 195 | —CO$_2$CH$_3$ | 7-OCH$_3$ | 274–276 | HRMS: 414.1117 |

82

Example 196

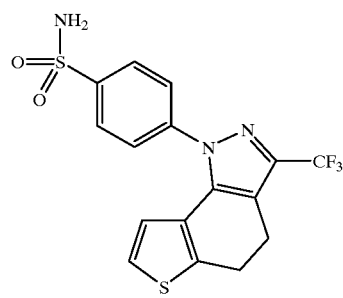

4-[4,5-Dihydro-3-(trifluoromethyl)-1H thieno[3,2-g]indazol-1-yl]benzenesulfonamide Step 1. Preparation of 4-keto-4,5,6,7-tetrahydrothianaphthene.

4-(2-Thienyl)butyric acid (28.42 g, 167 mmol) was placed in a round bottom flask with acetic anhydride (30 mL) and phosphoric acid (0.6 mL), and heated to reflux for 3.2 hours. The reaction mixture was poured into 100 mL of water, extracted with ethyl acetate, washed with brine, dried over MgSO$_4$, and concentrated in vacuo to give a brown oil (22.60 g) which was vacuum distilled (1 mm Hg, 107–115° C.) to give a white solid (13.08 g, 51%): mp 34–40° C.); $^1$H NMR (CDCl$_3$) 300 MHz 7.29 (d, J=5.2 Hz, 1H), 6.99 (d, J=5.2 Hz, 1H), 2.95 (t, J=6.0 Hz, 2H), 2.47 (m, 2H), 2.13 (m, 2H). M+H=153.

Step 2. Preparation of 4-keto-4,5,6,7-tetrahydro-5-(trifluoroacetyl)thianaphthene.

Ethyl trifluoroacetate (11.81 g, 83.1 mmol) was dissolved in ether (50 mL) and treated with a sodium methoxide solution (25% in methanol, 18.35 g, 84.9 mmol) followed by 4-keto-4,5,6,7-tetrahydrothianaphthene from Step 1 (12.57 g, 82.6 mmol) dissolved in ether (25 mL). The reaction was stirred for 69.4 hours at room temperature, then treated with 3N HCl (40 mL). The organic layer was collected, washed with brine, dried over MgSO$_4$, and concentrated in vacuo to give a brown solid which was recrystallized from ether/hexane to give the diketone (10.77 g, 52%) as brown needles; mp 54–64° C.; $^1$H NMR (CDCl$_3$) 300 MHz 15.80 (s, 1H), 7.41 (d, J=5.2 Hz, 1H), 7.17 (d, J=5.2 Hz, 1H), 3.04 (m, 2H), 2.91 (m, 2H); $^{19}$F NMR (CDCl$_3$) 282 MHz −70.37 (s). M+H=249.

Step 3. Preparation of 4-[4,5-dihydro-3-(trifluoromethyl)-1H thieno[3,2-g]indazol-1-yl]benzenesulfonamide 4-Sulfonamidophenylhydrazine hydrochloride (2.36 g, 10.6 mmol) was added to a stirred solution of the diketone from Step 2 (2.24 g, 9.0 mmol) in ethanol (20 mL). The reaction was heated to reflux and stirred 14.7 hours. The reaction mixture was filtered and washed with ethanol and with water to give the desired pyrazole as a white solid (2.69 g, 75%): mp 288–290° C.; $^1$H NMR (acetone-d$_6$) 300 MHz 8.12 (d, J=8.7 Hz, 2H), 7.83 (d, J=8.7 Hz, 2H), 7.27 (d, J=5.2 Hz, 1H), 6.81 (br s, 2H), 6.59 (s, J=5.4 Hz, 1H), 3.18 (m, 2H), 3.01 (m, 2H); $^{19}$F NMR (acetone d$_6$) 282 MHz −62.46 (s). High resolution mass spectrum Calc'd. for C$_{16}$H$_{12}$F$_3$N$_3$O$_2$S$_2$: 399.0323. Found: 399.0280.

Example 197

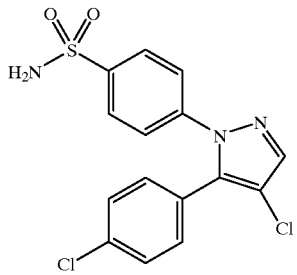

4-[5-(4-Chlorophenyl)-4-chloro-1H-pyrazol-1-yl]benzenesulfonamide

Step 1. Preparation of 3-[4-(chloro)phenyl]-propane-1,3-dione.

Ethyl formate (8.15 g, 0.11 mol) and 4'-chloroacetophenone (15.4 g, 0.1 mol) were stirred in ether (150 mL) at room temperature. Sodium methoxide (25%) (23.77 g, 0.11 mol) was added dropwise. The mixture was stirred at room temperature for 16 hours and was then treated with 150 mL of 1N hydrochloric acid. The phases were separated and the ethereal solution washed with brine, dried over magnesium sulfate, filtered and concentrated in vacuo to afford 18.3 g of a yellow oil. The resulting crude mixture was used directly in the next step without purification.

Step 2. Preparation of 4-[5-(4-chlorophenyl)-1H-pyrazol-1-yl-]benzenesulfonamide.

3-[4-(Chloro)phenyl]-propane-1,3-dione from Step 1 (18.3 g, 0.1 mol) and 4-sulfonamidophenylhydrazine hydrochloride (22.4 g, 0.1 mol) were dissolved in 150 mL of absolute ethanol and heated to reflux for 16 hours. The solution was cooled to room temperature, diluted with 100 mL of water and let stand, whereupon crystals of pyrazole formed that were isolated by filtration to provide 8.4 g (25%) of a white solid: mp 185–187° C.; $^1$H NMR (CDCl$_3$/300 MHz) 7.89 (d, J=8.7 Hz, 2H), 7.76 (d, J=1.8 Hz, 1H), 7.43 (d, J=8.7 Hz, 2H), 7.34 (d, J=8.7 Hz, 2H), 7.17 (d, J=8.7 Hz, 2H), 6.53 (d, J=1.8 Hz, 1H), 4.93 (brs, 2H). Anal. Calc'd for C$_{15}$H$_{12}$N$_3$SO$_2$Cl: C, 53.97; H, 3.62; N, 12.59. Found: C, 54.08; H, 3.57; N, 12.64.

Step 3. Preparation of 4-[5-(4-chlorophenyl)-4-chloro-1H-pyrazol-1-yl]benzenesulfonamide.

4-[5-(4-Chlorophenyl)-1H-pyrazol-1-yl]benzenesulfonamide from Step 2 (3.0 g, 9 mmol) was dissolved in 50 mL of acetic acid, and 9 mL of 1M chlorine in acetic acid was added dropwise. The mixture was stirred for 16 hours when sat. aq. sodium bicarbonate solution was slowly added until the mixture was neutral to pH paper. The mixture was extracted with ethyl acetate (3×50 mL), combined and washed with sat. aq. sodium bicarbonate and with brine, dried over magnesium sulfate, filtered, and concentrated. The resultant product was recrystallized from isopropanol to yield 2.6 g (78%) of a white solid: mp 168–171° C. (dec); $^1$H NMR (DMSO-D$_6$/300 MHz) 8.08 (s, 1H), 7.83 (d, J=8.7 Hz, 2H), 7.55 (d, J=8.7 Hz, 2H), 7.46 (brs, 2H), 7.44 (d, J=8.7 Hz, 2H), 7.35 (d, J=8.7 Hz, 2H). Anal. Calc'd for C$_{15}$H$_{11}$N$_3$SO$_2$Cl$_2$: C, 48.93; H, 3.01; N, 11.41. Found: C, 49.01; H, 2.97; N, 11.41.

Example 198

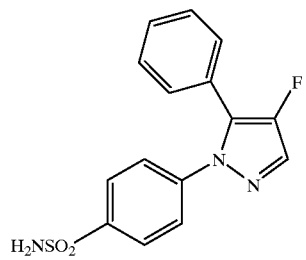

4-(4-Fluoro-5-phenyl-1H-pyrazol-1-yl)benzenesulfonamide

Step 1: Preparation of 2-fluoroacetophenone

To a solution of 2-hydroxyacetophenone (2.5 g, 18.4 mmol) in 100 mL CH$_2$Cl$_2$ at −78° C., was added triflic anhydride (10 g, 35.4 mmol) followed by 2,6-lutidine (4.1 mL, 35.4 mmol) and the mixture stirred at −78° C. for 50 minutes. The mixture was poured into CH$_2$Cl$_2$ and water and the CH$_2$Cl$_2$ layer separated, washed with brine, dried over Na$_2$SO$_4$ and concentrated to a peach solid. To a solution of the crude triflate in 100 mL THF was added 35 mL of 1N tetrabutylammonium fluoride in THF. The mixture was refluxed for 15 minutes, cooled and poured into ether and water. The ether layer was separated, washed with brine, dried over Na$_2$SO$_4$ and concentrated. Flash chromatography on silica gel using 20:1 hexane/EtOAc furnished the α-fluoroketone (0.852 g, 33.5%).

Step 2: Preparation of 4-(4-fluoro-5-phenyl-1H-pyrazol-1-yl)benzenesulfonamide

A solution of 2-fluoroacetophenone (200 mg, 1.45 mmol) in 2 mL dimethylformamide-dimethylacetal was refluxed for 18 hours. The mixture was cooled and concentrated to give the crude enaminoketone. Without further purification, the enaminoketone was treated with 4-sulfonamidophenyl hydrazine hydrochloride (0.34 g, 1.52 mmol) in 10 mL EtOH at reflux for 17 hours. The mixture was cooled, filtered and the filtrate concentrated to a yellow gum. Flash chromatography using a gradient of 5:1 to 2:1 hexane/EtOAc provided 0.11 g of a yellow solid: Recrystallization from ether/hexane gave the product as a pale yellow solid, mp 194–194.5° C.; Anal. calc'd for C$_{15}$H$_{12}$N$_3$O$_2$SF.0.2 H$_2$O: C, 56.14; H, 3.89; N, 13.09. Found: C, 55.99; H, 3.65; N, 12.92.

Example 199

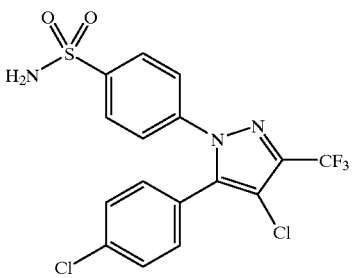

4-[5-(4-Chlorophenyl)-3-(trifluoromethyl)-4-chloro-1H-pyrazol-1-yl]benzenesulfonamide A 100 mL three-necked round-bottomed flask equipped with reflux condenser, gas dispersion tube and provisions for magnetic stirring was charged with 4-[5-(4-chlorophenyl)-3-trifluoromethyl-1H-pyrazol-1-yl]benzenesulfonamide (Example 1) (500 mg, 1.2 mmol) and 50 mL of glacial acetic acid. The solution was stirred at room temperature and treated with a stream of chlorine gas for a period of 15 minutes. The solution was then stirred at room temperature for 1.25 hours and then diluted with 100 mL of water. The solution was then extracted three times with ether and the combined ethereal phase washed with brine, dried over MgSO$_4$, filtered, and concentrated in vacuo to give a white solid that was recrystallized from ether/petroleum ether to provide 390 mg (75%) of 4-[5-(4-chlorophenyl)-4-chloro-3-trifluoromethyl-1H-pyrazol-1-yl]benzenesulfonamide: mp 180–182° C.; $^1$H NMR (CDCl$_3$/300 MHz) 7.97 (d, J=6.6 Hz, 2H), 7.49 (d, J=6.3 Hz, 2H), 7.45 (d, J=6.3 Hz, 2H), 7.25 (d, J=6.6 Hz, 2H), 5.78 (brs, 2H).

Example 200

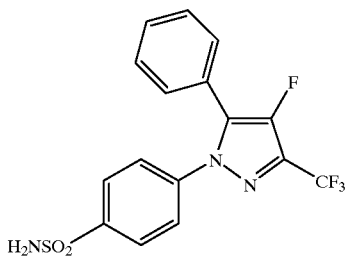

4-[4-Fluoro-5-phenyl-3-(trifluoromethyl)-1H-pyrazol-1-yl]benzenesulfonamide

Step 1: Preparation of 4,4,4-trifluoro-1-phenyl-butane-1,3-dione

To a solution of 2-fluoroacetophenone from Step 1 of Example 198 (0.48 g, 3.4 mmol) in 25 mL THF at −78° C., was added 1N lithium bis(trimethylsilyl)amide (4 mL) and the mixture stirred at −78° C. for 45 minutes. 1-(Trifluoroacetyl)imidazole (0.65 mL, 5.7 mmol) was added and the mixture stirred at −78° C. for 30 minutes and at 0° C. for 30 minutes. The mixture was quenched with 0.5 N HCl, poured into ether and water, and the ether layer separated, washed with brine, dried over Na$_2$SO$_4$ and concentrated. Flash chromatography on silica gel using a gradient of 10:1 to 4:1 hexane/EtOAc furnished the 1,3-diketone (0.34 g, 43%).

Step 2: Preparation of 4-[4-fluoro-5-phenyl-3-trifluoromethyl-1H-pyrazol-1-yl]benzenesulfonamide The diketone from Step 1 (0.34 g, 1.45 mmol) was treated with 4-sulfonamidophenyl hydrazine hydrochloride (0.35 g, 1.56 mmol) in 15 mL EtOH at reflux for 15 hours. The mixture was cooled, filtered and the filtrate concentrated to a yellow gum. Flash chromatography using 3:1 hexane/EtOAc provided 0.28 g of a yellow solid. Recrystallization from CH$_2$Cl$_2$/hexane gave the product as a pale yellow solid: Anal. calc'd for C$_{16}$H$_{11}$N$_3$O$_2$SF$_4$: C, 49.87; H, 2.88; N, 10.90. Found: C, 49.79; H, 2.88; N, 10.81

Example 201

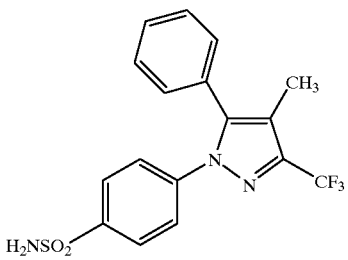

4-[4-Methyl-5-phenyl-3-(trifluoromethyl)-1H-pyrazol-1-yl]benzenesulfonamide

Step 1: Preparation of 2-methyl-1-phenyl-4,4,4-trifluorobutane-1,3-dione

To a solution of propiophenone (965 mg, 7.2 mmol) in THF (20 mL) at −78° C. was added sodium bis (trimethylsilyl)amide (7.9 mL of a 1M solution in THF). The solution was kept at −78° C. for 0.5 hour and then warmed to −20° C. over 1 hour. The solution was cooled to −78° C. and 1-(trifluoroacetyl)imidazole (1.5 g, 9.1 mmol) in THF (4 mL) was added via cannula. The solution was warmed to room temperature and stirred overnight. The mixture was partitioned between 1N HCl and ether. The organic solution was dried (Na$_2$SO$_4$) and concentrated to give the crude diketone (1.9 g).

Step 2: Preparation of 4-[4-methyl-5-phenyl-3-(trifluoromethyl)-1H-pyrazol-1-yl]benzenesulfonamide The diketone from Step 1 was dissolved in absolute ethanol (25 mL) and 4-sulfonamidophenylhydrazine hydrochloride (2.0 g, 9.0 mmol) was added. The mixture was heated at reflux for 19 hours. Volatiles were removed in vacuo and the residue dissolved in ethyl acetate. The organic solution was washed with water and brine, dried and concentrated. The residue was chromatographed on silica (2:1 hexane/ethyl acetate) to give the title pyrazole (1.52 g, 49%): mp 145–146° C.; Calc'd for C$_{17}$H$_{14}$N$_3$O$_2$SF$_3$: C, 53.54; H, 3.70; N, 11.01. Found: C, 53.41; H, 3.66; N, 10.92.

Example 202

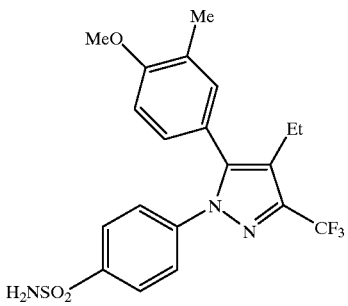

4-[4-Ethyl-5-(3-methyl-4-methoxyphenyl)-3-(trifluoromethyl)-1H-pyrazol-1-yl]benzenesulfonamide Step 1: Preparation of 4-methoxy-3-methylbutyrophenone:

To a suspension of aluminum chloride (10.3 g, 77.2 mmol) in dichloromethane (40 mL) at 0° C. was added dropwise a solution of 2-methylanisole (5.0 mL, 35.3 mmol) and butyric anhydride (5.8 mL, 35.3 mmol). The reaction solution was kept at 0° C. for 2 hours and then warmed to room temperature and stirred overnight. The reaction solution was poured into conc. HCl (9 mL) and ice water (80 mL). The reaction was extracted with dichloromethane and the organic layer was washed with 2N NaOH and brine, dried and concentrated. The residue was chromatographed on silica (9:1 hexane:ethyl acetate) to give the desired product (5.2 g, 77%).

Steps 2 and 3: Preparation of 4-[4-ethyl-5-(3-methyl-4-methoxyphenyl)-3-(trifluoromethyl)-1H-pyrazol-1-yl]benzenesulfonamide:

The title compound was prepared from the butyrophenone in Step 1 using the procedure described in Example 201, Steps 1 and 2: mp 135–136° C.; Calc'd for $C_{20}H_{20}N_3O_3SF_3$: C, 54.66; H, 4.59; N, 9.56. Found: C, 54.11; H, 4.38; N, 9.43.

Example 203

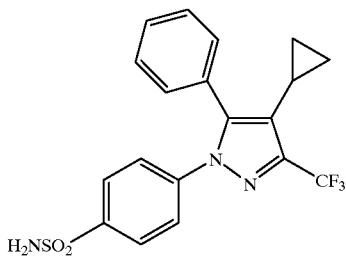

4-[4-Cyclopropyl-5-phenyl-3-(trifluoromethyl)-1H-pyrazol-1-yl]benzenesulfonamide Step 1: Preparation of 2-cyclopropylacetophenone:

To a suspension of sodium cyanide (1.8 g, 37.0 mmol) in dimethyl sulfoxide (20 mL) at 60° C. was added dropwise (bromomethyl)cyclopropane (5.0 g, 37.0 mmol). The addition was done at such a rate to keep the temperature of the reaction of 60° C. After the addition was completed, the reaction mixture was heated at 80° C. for 15 minutes. The mixture was cooled and partitioned between ether and water. The organic solution was washed with 1N HCl and water, dried and concentrated. The residue was dissolved in ether (5 mL) and added to a solution of phenyl magnesium bromide (25 mL of a 3M solution in ether) in ether (20 mL) and benzene (25 mL). The reaction mixture was stirred at room temperature for 20 hours, then poured into a 1N HCl solution and stirred for 1.5 hours. The organic solution was separated and the aqueous solution extracted with dichloromethane. The organic solution was dried and concentrated. The residue was chromatographed on silica (9:1 hexane:ethyl acetate) to give the desired product (2.0 g, 34%).

Steps 2 and 3: Preparation of 4-[4-cyclopropyl-5-phenyl-3-(trifluoromethyl)-1H-pyrazol-1-yl]benzenesulfonamide:

The title compound was prepared from the acetophenone in Step 1 using the procedure described in Example 201), Steps 1 and 2: mp 173–174° C.; Calc'd for $C_{19}H_{16}N_3O_2SF_3$: C, 56.01; H, 3.96; N, 10.31. Found: C, 55.85; H, 3.78; N, 10.19.

Example 204

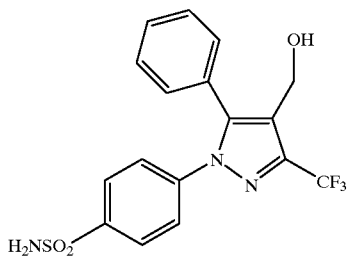

4-[4-hydroxymethyl-5-phenyl-3-(trifluoromethyl)-1H-pyrazol-1-yl]benzenesulfonamide Step 1: Preparation of 4-[4-bromomethyl-5-phenyl-3-(trifluoromethyl)-1H-pyrazol-1-yl]benzenesulfonamide:

To a solution of 4-[4-methyl-5-phenyl-3-(trifluoromethyl)-1H-pyrazol-1-yl]benzenesulfonamide prepared in Example 201 (500 mg, 1.3 mmol) in carbon tetrachloride (9 mL) and benzene (4 mL) was added N-bromosuccinimide (285 mg, 1.6 mmol). The mixture was irradiated with a sunlamp for 3.5 hours. The reaction mixture was partitioned between dichloromethane and water and the organic solution was dried and concentrated to give the desired product, 412 mg (69%).

Step 2: Preparation of 4-[4-formyl-5-phenyl-3-(trifluoromethyl)-1H-pyrazol-1-yl]benzenesulfonamide:

To a solution of the compound prepared in Step 1 (362 mg, 0.79 mmol) in dimethyl sulfoxide (7 mL) was added collidine (0.14 mL, 1.0 mmol). The solution was heated at 120° C. for 3 hours and then kept at overnight at room temperature. The reaction solution was partitioned between ethyl acetate and water and the organic solution was washed with water, dried and concentrated. The residue was chromatographed (1:1 hexane:ethyl acetate) to give the desired product (205 mg, 66%).

Step 3: Preparation of 4-[4-hydroxymethyl-5-phenyl-3-(trifluoromethyl)-1H-pyrazol-1-yl]benzenesulfonamide:

To a solution of the aldehyde prepared in Step 2 (165 mg, 0.41 mmol) in methanol (3.5 mL) at 0° C. was added sodium borohydride (16 mg, 0.41 mmol). The reaction solution was kept at 0° C. for 2.5 hours. The reaction was quenched with the addition of an aqueous 1M $KHSO_4$ solution (3 mL). The mixture was extracted with dichloromethane and the organic solution dried and concentrated. The residue was chromatographed on silica (1:1 hexane:ethyl acetate) to give the desired product (36 mg, 46%): m.p. 179–180° C.; $^1$H NMR d 7.91 (m, 2H), 7.53–7.40 (m, 5H), 6.75 (s, 2H), 4.53 (d, 2h, J=5.0 Hz), 4.30 (t, 1H, J=5.0 Hz).

Example 205

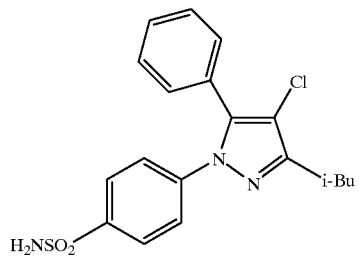

4-(4-Chloro-3-isobutyl-5-phenyl-1H-pyrazol-1-yl)benzenesulfonamide

To a solution of the pyrazole prepared in Example 175 (0.15 g, 0.42 mmol) in $CH_2Cl_2$ (10 mL) was added an excess of sulfuryl chloride slowly at room temperature. The mixture was stirred at room temperature for 2 hours, quenched with water and the aqueous layer extracted three time with methylene chloride. The combined organic layers were dried over $MgSO_4$ and concentrated to give an oil which was purified by flash chromatography on silica gel using 70:30 hexane/ethyl acetate as eluent to give the desired compound: HRMS m/z 389.0970 (calc'd for $C_{19}H_{20}ClN_3SO_2$, 389.0965).

The following compounds in Table X were prepared according to procedures similar to that exemplified in Examples 197–205, with the substitution of the appropriate starting material.

TABLE X

| Ex. | $R^3$ | $R^2$ | A | MP (° C.) | Analytical |
|---|---|---|---|---|---|
| 206 | Cl | H | 4-F | 175–178 | Calc C, 51.22; H, 3.15; N, 11.94 |
| | | | | | Obs. C, 51.43; H, 3.10; N, 11.82 |
| 207 | Br | H | 4-Cl | 209–210 | Calc. C, 43.66; H, 2.69; N, 10.18 |
| | | | | | Obs. C, 43.74; H, 2.70; N, 10.23 |
| 208 | Cl | H | H | 172–174 | Calc. C, 53.98; H, 3.62; N, 12.59 |
| | | | | | Cl, 10.62; S, 9.60 |
| | | | | | Obs. C, 54.17; H, 3.64, N, 12.45 |
| | | | | | Cl, 10.46; S, 9.42 |
| 209 | Cl | H | 3,5-di-Cl, 4-$OCH_3$ | 211–212 | Calc. C, 44.41; H, 2.80; N, 9.71 |
| | | | | | Obs. C, 44.72; H, 3.04, N, 9.72 |
| 210 | Br | H | 4-$CH_3$ | ND | HRMS: 391.0003 |
| 211 | Cl | H | 4-$CH_3$ | 160–163 | Calc. C, 55.25; H, 4.06; N, 12.08 |
| | | | | | Obs. C, 55.06; H, 4.03, N, 12.02 |
| 212 | Cl | H | 3-Cl, 4-$OCH_3$ | ND | Calc. C, 48.25; H, 3.29; N, 10.55 |
| | | | | | Cl, 17.80; S, 8.05 |
| | | | | | Obs. C, 48.10; H, 3.31, N, 10.52 |
| | | | | | Cl, 17.70; S, 7.98 |
| 213 | Cl | H | 4-$OCH_3$ | 155–156 | Calc. C, 52.82; H, 3.88; N, 11.55 |
| | | | | | Obs. C, 52.18; H, 3.93, N, 11.41 |
| 214 | Br | H | 4-$OCH_3$ | 130–132 | |
| 215 | CN | H | 4-$OCH_3$ | 216–219 | HRMS: 355.0860 |
| 216 | Cl | H | 3,5-di-F, 4-$OCH_3$ | 198–199 | Calc. C, 48.07; H, 3.03; N, 10.51 |
| | | | | | Obs. C, 48.45; H, 3.55, N, 10.10 |
| 217 | $SO_2CH_3$ | H | Cl | 182–185 | Calc. C, 46.66; H, 3.43; N, 10.20 |
| | | | | | Obs. C, 46.57; H, 3.49, N, 10.39 |
| 218 | $C_2H_5$ | $CF_3$ | H | 177–178 | Calc. C, 54.68; H, 4.08; N, 10.62 |
| | | | | | Obs. C, 54.61; H, 4.10; N, 10.54 |
| 219 | $CH_3$ | $CF_3$ | 4-$OCH_3$ | 158–159 | Calc. C, 52.55; H, 3.92; N, 10.21 |
| | | | | | Obs. C, 52.27; H, 4.00; N, 10.16 |
| 220 | $CH_3$ | $CF_3$ | 4-Cl | 154–155 | Calc. C, 49.10; H, 3.15; N, 10.10 |
| | | | | | Obs. C, 49.05; H, 3.02; N, 9.96 |
| 221 | $CH_3$ | $CF_3$ | 4-F | 103–104 | Calc. C, 51.13; H, 3.28; N, 10.52 |
| | | | | | Obs. C, 51.09; H, 3.26; N, 10.34 |
| 222 | $C_2H_5$ | $CF_3$ | 4-Cl | ND | Calc. C, 50.30; H, 3.52; N, 9.77 |
| | | | | | Obs. C, 50.40; H, 3.51; N, 9.72 |
| 223 | $CH_3$ | $CF_3$ | 4-$CH_3$ | 144–145 | Calc. C, 54.68; H, 4.08; N, 10.62 |
| | | | | | Obs. C, 54.38; H, 3.87; N, 10.31 |
| 224 | $C_2H_5$ | $CF_3$ | 4-$CH_3$ | 142–143 | Calc. C, 55.74; H, 4.43; N, 10.26 |
| | | | | | Obs. C, 55.60; H, 4.37; N, 10.17 |
| 225 | $C_2H_5$ | $CF_3$ | 4-$OCH_3$ | 160–161 | Calc. C, 53.64; H, 4.26; N, 9.87 |
| | | | | | Obs. C, 53.55; H, 4.23; N, 9.65 |
| 226 | $C_2H_5$ | $CF_3$ | 3-F, 4-$OCH_3$ | 156–157 | Calc. C, 51.46; H, 3.86; N, 9.47 |
| | | | | | Obs. C, 51.27; H, 3.75; N, 9.33 |
| 227 | Br | $CHF_2$ | 4-Cl | 224–226 | Calc. C, 41.53; H, 2.40; N, 9.08 |
| | | | | | Obs. C, 41.50; H, 2.38; N, 9.00 |
| 228 | Cl | $CHF_2$ | 3,5-di-Cl, 4-$OCH_3$ | 92–102 (dec) | Calc C, 42.30; H, 2.51; N, 8.70 |
| | | | | | Obs. C, 42.50; H, 2.67; N, 8.56 |
| 229 | Cl | $CHF_2$ | H | 174–176 | Calc. C, 50.07; H, 3.15; N, 10.95 |
| | | | | | Obs. C, 50.07; H, 3.18, N, 10.98 |
| 230 | Br | $CHF_2$ | H | 184–186 | Calc C, 44.87; H, 2.82; N, 9.81 |
| | | | | | Obs. C, 44.98; H, 2.81; N, 9.64 |

TABLE X-continued

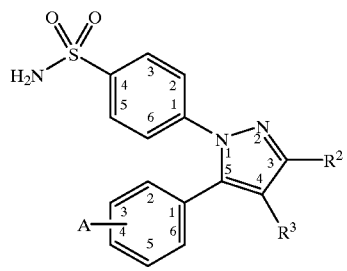

| Ex. | $R^3$ | $R^2$ | A | MP (° C.) | Analytical |
|---|---|---|---|---|---|
| 231 | Cl | CHF$_2$ | 4-OCH$_3$ | 171–172 | HRMS: 413.0351 |
| 232 | Cl | CN | H | 174–177 (sub) | Calc. C, 53.56; H, 3.09; N, 15.61; Cl, 9.98; S, 8.94 |
| | | | | | Obs. C, 53.81; H, 3.18; N, 15.43; Cl, 9.78; S, 8.91 |
| 233 | Cl | CN | 4-Cl | ND | Calc. C, 48.87; H, 2.56; N, 14.25; Cl, 18.03; S, 8.15 |
| | | | | | Obs. C, 48.99; H, 2.55; N, 14.30; Cl, 17.96; S, 8.08 |
| 234 | Cl | CN | 4-F | ND | Calc. C, 51.00; H, 2.68; N, 14.87; Cl, 9.41; S, 8.51 |
| | | | | | Obs. C, 51.19; H, 2.73; N, 14.98; Cl, 9.22; S, 8.56 |
| 235 | Br | CN | 4-F | ND | Calc. C, 45.62; H, 2.39; N, 13.30; Br, 18.97; S, 7.61 |
| | | | | | Obs. C, 45.51; H, 2.36; N, 13.21; Br, 19.09; S, 7.51 |
| 236 | Br | CN | H | ND | Calc. C, 47.66; H, 2.75; N, 13.89; Br, 19.81; S, 7.95 |
| | | | | | Obs. C, 47.62; H, 2.77; N, 13.77; Br, 19.74; S, 8.04 |
| 237 | Br | CO$_2$C$_2$H$_5$ | 4-Cl | ND | HRMS: 482.9707 |
| 238 | Cl | CO$_2$CH$_3$ | H | ND | HRMS: 342.0495 |
| 239 | Cl | CO$_2$CH$_3$ | 4-Cl | ND | HRMS: 426.0128 |
| 240 | Cl | CO$_2$C$_2$H$_5$ | 4-Cl | ND | HRMS: 440.0207 |
| 241 | Cl | CO$_2$CH$_3$ | 4-F | ND | HRMS: 410.0391 |
| 242 | Br | CO$_2$CH$_3$ | 4-F | ND | HRMS: 453.9880 |
| 243 | Cl | CO$_2$CH$_3$ | 4-OCH$_3$, 3-Cl | ND | Calc. C, 47.38; H, 3.31; N, 9.21; Cl, 15.54; S, 7.03 |
| | | | | | Obs. C, 47.10; H, 3.26; N, 9.01; Cl, 15.74; S, 6.92 |
| 244 | Cl | CO$_2$CH$_3$ | 4-OCH$_3$, 3,5-di-Cl | 198–199 | Calc. C, 44.06; H, 2.88; N, 8.56. |
| | | | | | Obs. C, 43.59; H, 2.77; N, 8.44 |
| 245 | Cl | CO$_2$CH$_3$ | 4-OCH$_3$, 3-Br | ND | Calc. C, 43.18, H, 3.02; N, 8.39; S, 6.40 |
| | | | | | Obs. C, 43.25; H, 2.97; N, 8.40; S, 6.59 |
| 246 | Cl | CONH$_2$ | H | ND | HRMS: 377.0539 |
| 247 | Cl | CONH$_2$ | 4-Cl | ND | HRMS: 411.0115 |
| 248 | Cl | CONH$_2$ | 4-F | ND | HRMS: 395.0397 |
| 249 | Br | CONH$_2$ | 4-F | ND | Calc. C, 43.75, H, 2.75; N, 12.75; Br, 18.19; S, 7.30 |
| | | | | | Obs. C, 43.65; H, 2.78; N, 12.66; Br, 18.13; S, 7.21 |
| 250 | Br | CONH$_2$ | H | ND | HRMS: 419.9920 |
| 251 | Cl | CO$_2$H | H | ND | HRMS 377.0249 |
| 252 | Cl | CO$_2$H | 4-Cl | ND | Calc. C, 46.62, H, 2.69; N, 10.19; Cl, 17.20; S, 7.78 |
| | | | | | Obs. C, 46.59, H, 2.68; N, 10.21; Cl, 17.25; S, 7.73 |
| 253 | Cl | CO$_2$H | 4-OCH$_3$, 3,5-di-Cl | 220 (dec) | Calc. C, 42.83; H, 2.54; N, 8.81 |
| | | | | | Obs. C, 43.65; H, 2.52; N, 8.78 |
| 254 | Cl | CH$_3$ | H | ND | Calc. C, 55.25; H, 4.06; N, 12.08 |
| | | | | | Obs. C, 55.24; H, 4.26; N, 12.17 |
| 255 | Cl | CH$_2$OH | H | 195–197 | HRMS: 363.0431 |
| 256 | Cl | CH$_2$OH | 4-Cl | 203–204 | Calc. C, 48.25; H, 3.29; N, 10.55 |
| | | | | | Obs. C, 48.36; H, 3.27; N, 10.50 |
| 257 | Cl | (CH$_2$)$_2$CO$_2$H | 4-Cl | 212–214 | Calc. C, 49.10; H, 3.43; N, 9.54 |
| | | | | | Obs. C, 49.23; H, 3.45; N, 9.49 |
| 258 | OCH$_3$ | CF$_3$ | H | 137–138 | Calc. C, 51.38; H, 3.55; N, 10.57 |
| | | | | | Obs. C, 51.40; H, 3.47; N, 10.47 |

Example 259

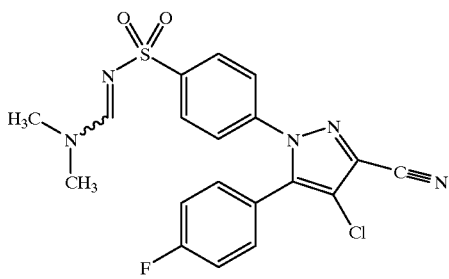

4-[4-Chloro-3-cyano-5-[4-(fluoro)phenyl])-1H-pyrazol-1-yl]-N-[(dimethylamino)methylene]benzenesulfonamide Increasing the polarity of the eluant used in the purification in Example 234 to 60% ethyl acetate, upon concentration of the appropriate fractions, yielded 4-[4-chloro-3-cyano-5-[4-(fluoro)phenyl])-1H-pyrazol-1-yl]-N-[(dimethylamino)methylene]benzenesulfonamide (0.485 g, 15%): High Resolution Mass Spectrum (MLi+) calc'd: 438.0779. Found: 438.0714. Elemental analysis calc'd for $C_{19}H_{15}N_5O_2FClS$: C, 52.84: H, 3.50: N, 16.22; Cl, 8.21; S, 7.42. Found: C, 52.76; H, 3.52; N, 16.12; Cl, 8.11; S, 7.35.

Example 260

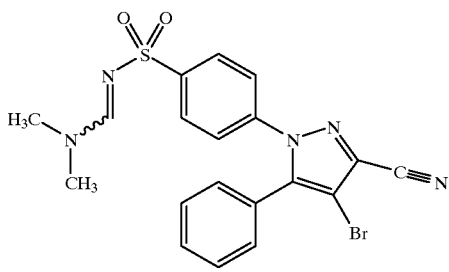

4-[4-Bromo-3-cyano-5-phenyl-1H-pyrazol-1-yl]-N-[(dimethylamino)methylene]benzenesulfonamide Similarly, 4-[4-bromo-3-cyano-5-phenyl-1H-pyrazol-1-yl]-N-[(dimethylamino)methylene]benzenesulfonamide was isolated from the purification of Example 235 (0.153 g, 28%): High Resolution Mass Spectrum (M+) calc'd: 457.0208. Found: 457.0157. Elemental analysis calc'for $C_{19}H_{16}N_5O_2BrS$: C, 49.79: H, 3.52: N, 15.28; Br, 17.43; S, 6.99. Found: C, 49.85; H, 3.56; N, 15.10; Br, 17.52; S, 6.87.

Example 261

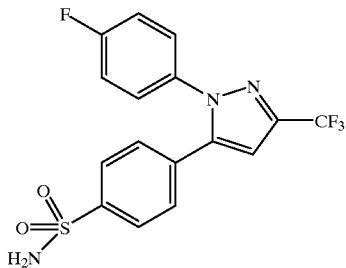

4-[1-(4-Fluorophenyl)-3-(trifluoromethyl)-1H-pyrazol-5-yl]benzenesulfonamide

Step 1: Preparation of N,N-bis(4-methoxybenzyl)-4-(aminosulfonyl)acetophenone.

To a solution of 4-(aminosulfonyl)acetophenone (2.0 g, 9.0 mmol) in dimethylsulfoxide (25 mL) was added sodium hydride (450 mg, 19.0 mmol). The reaction mixture was stirred for 45 minutes and then 4-methoxybenzyl bromide (3.5 g, 19.0 mmol) in dimethylsulfoxide (5 mL) was added via cannula. The mixture was stirred at room temperature for 24 hours and partitioned between ethyl acetate and pH 7 buffer. The aqueous solution was extracted with ethyl acetate. The organic solution was dried (MgSO₄) and concentrated. The residue was chromatographed on silica (2:1 hexane:ethyl acetate) to give the desired product (815 mg, 21%).

Step 2: Preparation of N,N-bis(4-methoxybenzyl)-4-[1-(4-fluorophenyl)-3-trifluoromethyl-1H-pyrazol-5-yl]benzenesulfonamide To a 25% sodium methoxide solution in methanol (0.2 mL) was added ethyl trifluoroacetate (75 mg, 0.53 mmol) and the protected acetophenone from Step 1 (235 mg, 0.53 mmol). THF (0.5 mL) was added and the reaction mixture was heated at reflux for 2 hours and then stirred at room temperature overnight. The mixture was partitioned between ether and 1N HCl solution. The organic solution was dried and concentrated to give the crude diketone (279 mg), which was diluted with absolute ethanol (2.5 mL). To this slurry was added pyridine (49 mg, 0.62 mmol) and 4-fluorophenylhydrazine hydrochloride (80 mg, 0.50 mmol). The mixture was stirred at room temperature for 24 hours and concentrated in vacuo. The residue was dissolved in methylene chloride and washed with 1N HCl. The organic solution was dried and concentrated. The residue was chromatographed on silica (3:1 hexane:ethyl acetate) to give the protected pyrazole (159 mg, 51%).

Step 3: Preparation of 4-[1-(4-fluorophenyl)-3-trifluoromethyl-1H-pyrazol-5-yl]benzenesulfonamide To a solution of the protected pyrazole (50 mg, 0.08 mmol) in acetonitrile (1 mL) and water (0.3 mL) was added ceric ammonium nitrate (360 mg, 0.65 mmol). The reaction solution was kept at room temperature for 16 hours. The solution was poured into water (15 mL) and extracted with ethyl acetate (2×25 mL). The combined extracts were dried (MgSO₄) and concentrated. The residue was chromatographed on silica (2:1 hexane:ethyl acetate) to give the desired product (13 mg, 42%): $^1$H NMR (CD₃OD) 7.88 (d, 2H), 7.46 (d, 2H), 7.39 (dd, 2H), 7.21 (t, 2H), 7.06 (s, 1H).

Example 262

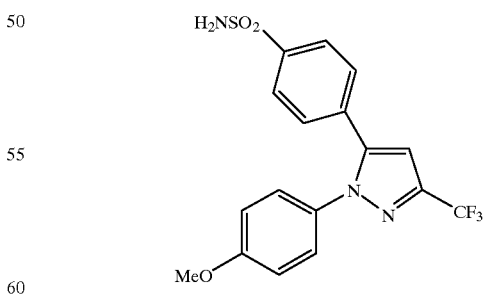

4-[1-(4-methoxyphenyl)-3-(trifluoromethyl)-1H-pyrazol-5-yl]benzenesulfonamide

The title compound was prepared using the procedure described in Example 261: HRMS m/z 397.0702 (calc'd for $C_{17}H_{14}N_3O_3SF_3$, 397.0708).

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.,* 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDS,* in Non-steroidal Anti-Inflammatory Drugs, (J. Lombardino, ed. 1985)). The % inhibition shows the % decrease from control paw volume determined in this procedure and the data for selected compounds in this invention are summarized in Table I.

Rat Carrageenan-induced Analgesia Test

The analgesia test using rat carrageenan was performed with materials, reagents and procedures essentially as described by Hargreaves, et al., (*Pain,* 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table XI.

TABLE XI

| Examples | RAT PAW EDEMA<br>% Inhibition<br>@ 10 mg/kg body weight | ANALGESIA<br>% Inhibition<br>@ 30 mg/kg body weight |
|---|---|---|
| 1 | 44 | 94 |
| 2 | 35 | 38 |
| 58 | 36 | 65 |
| 59 | 25 | 41 |
| 60 | 49 | 39 |
| 82 | 22* | |
| 86 | 42* | |
| 98 | 2* | |
| 117 | 32 | |
| 129 | 47* | |
| 170 | 18* | |
| 171 | 14 | 37 |
| 188 | 32* | |
| 197 | 45* | 27 |
| 199 | 35 | |

*Assay performed at 30 mg/kg body weight

Evaluation of COX I and COX II activity in vitro

The compounds of this invention exhibited inhibition in vitro of COX II. The COX II inhibition activity of the compounds of this invention illustrated in the Examples was determined by the following methods.

A. Preparation of recombinant cox baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D. R. O'Reilly et al (*Baculovirus Expression Vectors: A Laboratory Manual* (1992)). Recombinant baculoviruses were isolated by transfecting 4 µg of baculovirus transfer vector DNA into SF9 insect cells (2×10e8) along with 200 ng of linearized baculovirus plasmid DNA by the calcium phosphate method. See M. D. Summers and G. E. Smith, *A Manual of Methods for Baculovirus Vectors and Insect Cell Culture Procedures,* Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors (0.5×10$^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX I and COX II activity:

COX activity was assayed as $PGE_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The $PGE_2$ formed was measured by standard ELISA technology (Cayman Chemical). Results are shown in Table XII.

TABLE XII

| Example | Human COX II<br>$ID_{50}$ µM | Human COX I<br>$ID_{50}$ µM |
|---|---|---|
| 1 | <.1 | 18 |
| 2 | <.1 | 15.0 |
| 3 | <.1 | >100 |
| 4 | .6 | 37.5 |
| 5 | <.1 | 6.3 |
| 6 | .2 | 78.7 |
| 7 | 14 | >100 |
| 8 | 37.7 | >100 |
| 9 | .1 | 55.2 |
| 10 | 2.7 | >100 |
| 12 | 20 | >100 |
| 55 | 22 | 77.9 |
| 56 | <.1 | 11.7 |
| 57 | 47.9 | >100 |
| 58 | <.1 | 5.7 |
| 59 | <.1 | 26.8 |
| 60 | <.1 | .8 |
| 82 | <.1 | 1.1 |
| 84 | <.1 | 65.5 |
| 85 | 73.6 | >100 |
| 86 | .5 | >100 |

TABLE XII-continued

| Example | Human COX II ID$_{50}$ µM | Human COX I ID$_{50}$ µM |
|---|---|---|
| 96 | 6.5 | >100 |
| 97 | 96 | >100 |
| 98 | <.1 | 1.7 |
| 117 | .3 | >100 |
| 128 | 1.1 | >100 |
| 129 | <.1 | 13.5 |
| 130 | 3.6 | 12.5 |
| 131 | .2 | >100 |
| 138 | .6 | <.1 |
| 170 | .1 | >100 |
| 171 | .8 | >100 |
| 172 | 4.2 | >100 |
| 173 | 4.7 | >100 |
| 174 | 3.5 | 100 |
| 175 | 66.9 | >100 |
| 176 | .3 | >100 |
| 187 | 1.1 | 13.6 |
| 188 | .2 | 19.8 |
| 196 | .6 | 4.1 |
| 197 | <.1 | 3.4 |
| 198 | 4.2 | 56.5 |
| 199 | <.1 | <.1 |
| 200 | <.1 | .5 |
| 201 | <.1 | 2.2 |
| 202 | <.1 | 91 |
| 203 | 27 | >100 |
| 204 | 6.7 | >100 |
| 205 | <.1 | 2.1 |
| 259 | 1.1 | >100 |
| 260 | 1.1 | >100 |
| 261 | <.1 | <.1 |
| 262 | <.1 | <.1 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A method of treating an inflammation-associated skin-related condition in a subject, said method comprising administering to the subject having said condition, a therapeutically-effective amount of a compound selected from compounds, and their pharmaceutically acceptable salts, of the group consisting of 4-[5-(4-chlorophenyl)-3-(trifluoromethyl)-1H-pyrazol-1-yl]benzenesulfonamide;

4-[5-(4-bromophenyl)-3-(trifluoromethyl)-1H-pyrazol-1-yl]benzenesulfonamide;

4-[5-(3-chlorophenyl)-3-(trifluoromethyl)-1H-pyrazol-1-yl]benzenesulfonamide;

4-[5-(4-methylphenyl)-3-(trifluoromethyl)-1H-pyrazol-1-yl]benzenesulfonamide;

4-[5-(2-chlorophenyl)-3-(trifluoromethyl)-1H-pyrazol-1-yl]benzenesulfonamide;

4-[5-(2-fluorophenyl)-3-(trifluoromethyl)-1H-pyrazol-1-yl]benzenesulfonamide;

4-[5-(4-trifluoromethylphenyl)-3-(trifluoromethyl)-1H-pyrazol-1-yl]benzenesulfonamide;

4-[5-(4-fluorophenyl)-3-(trifluoromethyl)-1H-pyrazol-1-yl]benzenesulfonamide;

4-[5-phenyl-3-(trifluoromethyl)-1H-pyrazol-1-yl]benzenesulfonamide;

4-[5-(4-methoxyphenyl)-3-(trifluoromethyl)-1H-pyrazol-1-yl]benzenesulfonamide;

4-[5-(4-trifluoromethoxyphenyl)-3-(trifluoromethyl)-1H-pyrazol-1-yl]benzenesulfonamide;

4-[5-(2-methylphenyl)-3-(trifluoromethyl)-1H-pyrazol-1-yl]benzenesulfonamide;

4-[5-(4-nitrophenyl)-3-(trifluoromethyl)-1H-pyrazol-1-yl]benzenesulfonamide;

4-[5-(4-aminophenyl)-3-(trifluoromethyl)-1H-pyrazol-1-yl]benzenesulfonamide;

4-[5-(4-chlorophenyl)-3-(difluoromethyl)-1H-pyrazol-1-yl]benzenesulfonamide;

4-[5-(4-[methylthio]phenyl)-3-(difluoromethyl)-1H-pyrazol-1-yl]benzenesulfonamide;

4-[5-(2,4-[difluoro]phenyl)-3-(trifluoromethyl)-1H-pyrazol-1-yl]benzenesulfonamide;

4-[5-(2,6-[difluoro]phenyl)-3-(trifluoromethyl)-1H-pyrazol-1-yl]benzenesulfonamide;

-[5-(4-chlorophenyl)-3-(heptafluoropropyl)-1H-pyrazol-1-yl]benzenesulfonamide;

4-[5-(4-chlorophenyl)-3-(chloro-difluoromethyl)-1H-pyrazol-1-yl]benzenesulfonamide;

4-[5-(4-chlorophenyl)-3-(pentafluoroethyl)-1H-pyrazol-1-yl]benzenesulfonamide;

4-[5-(4-biphenyl)-3-(difluoromethyl)-1H-pyrazol-1-yl]benzenesulfonamide;

4-[5-(4-(morpholino)phenyl)-3-(difluoromethyl)-1H-pyrazol-1-yl]benzenesulfonamide;

4-[5-(1-cyclohexenyl)-3-(difluoromethyl)-1H-pyrazol-1-yl]benzenesulfonamide;

4-[5-(1-cyclohexyl)-3-(difluoromethyl)-1H-pyrazol-1-yl]benzenesulfonamide;

4-[5-(4-[trifluoromethyl]phenyl)-3-(difluoromethyl)-1H-pyrazol-1-yl]benzenesulfonamide;

4-[5-(3,4-dichlorophenyl)-3-(trifluoromethyl)-1H-pyrazol-1-yl]benzenesulfonamide; and 4-[5-(2,4-dichlorophenyl)-3-(trifluoromethyl)-1H-pyrazol-1-yl]benzenesulfonamide.

2. The method of claim 1 where the compound is 4-[5-(4-methylphenyl)-3-(trifluoromethyl)-1H-pyrazol-1-yl]benzenesulfonamide, or a pharmaceutically-acceptable salt thereof.

3. The method of claim 1 where the compound is 4-[5-(4-chlorophenyl)-3-(difluoromethyl)-1H-pyrazol-1-yl]benzenesulfonamide, or a pharmaceutically-acceptable salt thereof.

4. The method of claim 1 where the compound is 4-[5-(4-chlorophenyl)-3-(trifluoromethyl)-1H-pyrazol-1-yl]benzenesulfonamide, or a pharmaceutically-acceptable salt thereof.

5. The method of claim 1 wherein the condition is selected from psoriasis, eczema, burns and dermatitis.

6. The method of claim 1 wherein the condition is a burn.

7. The method of claim 1 wherein the condition is dermatitis.

8. The method of claim 1 wherein the condition is psoriasis.

* * * * *